US011077068B2

(12) United States Patent
Myers et al.

(10) Patent No.: US 11,077,068 B2
(45) Date of Patent: **\*Aug. 3, 2021**

(54) UNIFORM FILMS FOR RAPID-DISSOLVE DOSAGE FORM INCORPORATING ANTI-TACKING COMPOSITIONS

(71) Applicant: Aquestive Therapeutics, Inc., Warren, NJ (US)

(72) Inventors: Garry L. Myers, Kingsport, TN (US); Pradeep Sanghvi, North Brunswick, NJ (US); Andrew Philip Verrall, Indianapolis, IN (US); Vimala Francis, Fremont, CA (US); Laura Brooks, Sheboygan, WI (US)

(73) Assignee: Aquestive Therapeutics, Inc., Warren, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/717,041

(22) Filed: Dec. 17, 2019

(65) Prior Publication Data

US 2020/0315985 A1    Oct. 8, 2020

Related U.S. Application Data

(63) Continuation of application No. 16/505,244, filed on Jul. 8, 2019, now abandoned, which is a continuation
(Continued)

(51) Int. Cl.
*A61K 47/38* (2006.01)
*A61K 9/70* (2006.01)
(Continued)

(52) U.S. Cl.
CPC ............ *A61K 9/7007* (2013.01); *A23L 33/10* (2016.08); *A23L 33/105* (2016.08); *A23L 33/15* (2016.08);
(Continued)

(58) Field of Classification Search
CPC .................................................... A61K 9/0056
See application file for complete search history.

(56) References Cited

U.S. PATENT DOCUMENTS 26,401 A     12/1859  Brashear et al.
307,537 A    11/1884  Foulks
(Continued)

FOREIGN PATENT DOCUMENTS

AU      741362 B2     11/2001
CA     2274910 C       7/2005
(Continued)

OTHER PUBLICATIONS

Transaction History for Ex Parte Reexamination Control No. 90/012,098, current as of Jun. 18, 2019.
(Continued)

*Primary Examiner* — Benjamin J Packard
(74) *Attorney, Agent, or Firm* — Hoffmann & Baron, LLP

(57) ABSTRACT

The present invention relates to water-soluble films incorporating anti-tacking agents and methods of their preparation. Anti-tacking agents may improve the flow characteristics of the compositions and thereby reduce the problem of film adhering to a user's mouth or to other units of film. In particular, the present invention relates to edible water-soluble delivery systems in the form of a film composition including a water-soluble polymer, an active component selected from cosmetic agents, pharmaceutical agents, vitamins, bioactive agents and combinations thereof and at least one anti-tacking agent.

20 Claims, 3 Drawing Sheets

Related U.S. Application Data of application No. 15/818,997, filed on Nov. 21, 2017, now abandoned, which is a continuation of application No. 15/438,406, filed on Feb. 21, 2017, now Pat. No. 9,855,221, which is a continuation of application No. 15/398,398, filed on Jan. 4, 2017, now abandoned, which is a continuation of application No. 15/144,191, filed on May 2, 2016, now abandoned, which is a continuation of application No. 14/844,810, filed on Sep. 3, 2015, now abandoned, which is a continuation of application No. 14/284,019, filed on May 21, 2014, now abandoned, which is a continuation of application No. 11/517,982, filed on Sep. 8, 2006, now Pat. No. 8,765,167, which is a continuation-in-part of application No. 10/074,272, filed on Feb. 14, 2002, now Pat. No. 7,425,292.

(60) Provisional application No. 60/715,528, filed on Sep. 9, 2005, provisional application No. 60/328,868, filed on Oct. 12, 2001.

(51) Int. Cl.

| | | |
|---|---|---|
| *A61K 47/12* | (2006.01) | |
| *A61K 47/34* | (2017.01) | |
| *A61K 31/355* | (2006.01) | |
| *A23L 33/16* | (2016.01) | |
| *A23L 33/15* | (2016.01) | |
| *A23L 33/105* | (2016.01) | |
| *A23L 33/10* | (2016.01) | |
| *A23P 30/10* | (2016.01) | |
| *A23P 20/20* | (2016.01) | |
| *A61K 47/22* | (2006.01) | |
| *A61K 9/00* | (2006.01) | |
| *A61K 31/485* | (2006.01) | |
| *A61K 47/02* | (2006.01) | |
| *A61K 47/14* | (2017.01) | |
| *A61K 47/36* | (2006.01) | |

(52) U.S. Cl.
CPC ............... *A23L 33/16* (2016.08); *A23P 20/20* (2016.08); *A23P 30/10* (2016.08); *A61K 9/006* (2013.01); *A61K 9/0056* (2013.01); *A61K 31/355* (2013.01); *A61K 31/485* (2013.01); *A61K 47/02* (2013.01); *A61K 47/12* (2013.01); *A61K 47/14* (2013.01); *A61K 47/22* (2013.01); *A61K 47/34* (2013.01); *A61K 47/36* (2013.01); *A61K 47/38* (2013.01); *A23V 2002/00* (2013.01)

(56) References Cited

U.S. PATENT DOCUMENTS

| | | |
|---|---|---|
| 476,085 A | 5/1892 | Smith |
| 492,417 A | 2/1893 | McAlister |
| 503,070 A | 8/1893 | Broadwell et al. |
| 596,302 A | 12/1897 | McMahon |
| 688,446 A | 10/1901 | Stempel, Jr. |
| 1,110,546 A | 9/1914 | Hewitt |
| 1,827,354 A | 10/1931 | Cooper |
| 2,142,537 A | 1/1939 | Tiaxa |
| 2,277,038 A | 3/1942 | Curtis |
| 2,352,691 A | 7/1944 | Curtis |
| 2,376,656 A | 5/1945 | Leonia |
| 2,501,544 A | 3/1950 | Shrontz |
| 2,612,165 A | 9/1952 | Szukerski |
| 2,980,554 A | 4/1961 | Gentile et al. |
| 3,007,848 A | 11/1961 | Stroop |
| 3,044,338 A | 7/1962 | Horton et al. |
| 3,131,068 A | 4/1964 | Grief |
| 3,142,217 A | 7/1964 | Busse |
| 3,189,174 A | 6/1965 | Cormack |
| 3,237,596 A | 3/1966 | Grass, Jr. et al. |
| 3,242,959 A | 3/1966 | Glass |
| 3,249,109 A | 5/1966 | Maeth et al. |
| 3,324,754 A | 6/1967 | Peavy |
| 3,370,497 A | 2/1968 | Busse |
| 3,419,137 A | 12/1968 | Walck, III |
| 3,444,858 A | 5/1969 | Russell |
| 3,451,539 A | 6/1969 | Wysocki |
| 3,536,809 A | 10/1970 | Applezwig |
| 3,539,605 A | 11/1970 | Oberhofer |
| 3,551,556 A | 12/1970 | Kliment et al. |
| 3,598,122 A | 8/1971 | Zaffaroni |
| 3,610,248 A | 10/1971 | Davidson |
| 3,625,351 A | 12/1971 | Eisenberg |
| 3,632,740 A | 1/1972 | Robinson et al. |
| 3,640,741 A | 2/1972 | Etes |
| 3,641,237 A | 2/1972 | Gould et al. |
| 3,650,461 A | 3/1972 | Hutcheson |
| 3,677,866 A | 7/1972 | Pickett et al. |
| 3,731,683 A | 5/1973 | Zaffaroni |
| 3,753,732 A | 8/1973 | Boroshok |
| 3,755,558 A | 8/1973 | Scribner |
| 3,768,725 A | 10/1973 | Pilaro |
| 3,795,527 A | 3/1974 | Stone et al. |
| 3,797,494 A | 3/1974 | Zaffroni |
| 3,809,220 A | 5/1974 | Arcudi |
| 3,814,095 A | 6/1974 | Lubens |
| 3,825,014 A | 7/1974 | Wroten |
| 3,835,995 A | 9/1974 | Haines |
| 3,840,657 A | 10/1974 | Norfleet |
| 3,892,905 A | 7/1975 | Albert |
| 3,911,099 A | 10/1975 | DeFoney et al. |
| 3,933,245 A | 1/1976 | Mullen |
| 3,972,995 A | 8/1976 | Tsuk et al. |
| 3,979,839 A | 9/1976 | Blanie |
| 3,996,934 A | 12/1976 | Zaffaroni |
| 3,998,215 A | 12/1976 | Anderson et al. |
| 4,015,023 A | 3/1977 | Lamberti et al. |
| 4,022,924 A | 5/1977 | Mitchell et al. |
| 4,029,757 A | 6/1977 | Mlodozeniec et al. |
| 4,029,758 A | 6/1977 | Mlodozeniec et al. |
| 4,031,200 A | 6/1977 | Reif |
| 4,049,848 A | 9/1977 | Goodale et al. |
| 4,053,046 A | 10/1977 | Roark |
| 4,067,116 A | 1/1978 | Bryner et al. |
| 4,105,116 A | 8/1978 | Jones et al. |
| 4,123,592 A | 10/1978 | Rainer et al. |
| 4,126,503 A | 11/1978 | Gardner |
| 4,128,445 A | 12/1978 | Sturzenegger et al. |
| 4,136,145 A | 1/1979 | Fuchs et al. |
| 4,136,162 A | 1/1979 | Fuchs et al. |
| 4,139,627 A | 2/1979 | Lane et al. |
| 4,202,966 A | 5/1980 | Misaki et al. |
| 4,226,848 A | 10/1980 | Nagai et al. |
| 4,249,531 A | 2/1981 | Heller et al. |
| 4,251,400 A | 2/1981 | Columbus |
| 4,251,561 A | 2/1981 | Gajewski |
| 4,284,194 A | 8/1981 | Flatau |
| 4,284,534 A | 8/1981 | Ehrlich |
| 4,292,299 A | 9/1981 | Suzuki et al. |
| 4,294,820 A | 10/1981 | Keith et al. |
| 4,302,465 A | 11/1981 | Ekenstam et al. |
| 4,307,075 A | 12/1981 | Martin |
| 4,307,117 A | 12/1981 | Leshik |
| 4,325,855 A | 4/1982 | Dickmann et al. |
| 4,341,563 A | 7/1982 | Kurihara et al. |
| 4,365,423 A | 12/1982 | Arter et al. |
| 4,373,036 A | 2/1983 | Chang et al. |
| 4,390,450 A | 6/1983 | Gibson et al. |
| 4,406,708 A | 9/1983 | Hesselgren |
| 4,432,975 A | 2/1984 | Libby |
| 4,438,258 A | 3/1984 | Graham |
| 4,451,260 A | 5/1984 | Mitra |
| 4,460,532 A | 7/1984 | Cornell |
| 4,460,562 A | 7/1984 | Keith et al. |
| 4,466,973 A | 8/1984 | Rennie |
| 4,478,658 A | 10/1984 | Wittwer |

(56) References Cited

U.S. PATENT DOCUMENTS

| | | |
|---|---|---|
| 4,483,846 A | 11/1984 | Koide et al. |
| 4,503,070 A | 3/1985 | Eby, III |
| 4,511,592 A | 4/1985 | Percel et al. |
| 4,515,162 A | 5/1985 | Yamamoto et al. |
| 4,517,173 A | 5/1985 | Kizawa et al. |
| 4,529,301 A | 7/1985 | Rountree |
| 4,529,601 A | 7/1985 | Broberg et al. |
| 4,529,748 A | 7/1985 | Wienecke |
| 4,562,020 A | 12/1985 | Hijiya et al. |
| 4,568,535 A | 2/1986 | Loesche |
| 4,569,837 A | 2/1986 | Suzuki et al. |
| 4,572,832 A | 2/1986 | Kigasawa et al. |
| 4,582,835 A | 4/1986 | Lewis et al. |
| 4,585,452 A | 4/1986 | Sablotsky |
| 4,588,592 A | 5/1986 | Elias |
| 4,593,053 A | 6/1986 | Jevne et al. |
| 4,598,089 A | 7/1986 | Hadvary et al. |
| 4,608,249 A | 8/1986 | Otsuka et al. |
| 4,613,497 A | 9/1986 | Chavkin |
| 4,615,697 A | 10/1986 | Robinson |
| 4,619,701 A | 10/1986 | Angrick et al. |
| 4,621,482 A | 11/1986 | Crevasse et al. |
| 4,623,394 A | 11/1986 | Nakamura et al. |
| 4,631,837 A | 12/1986 | Magoon |
| 4,639,367 A | 1/1987 | Mackles |
| 4,648,509 A | 3/1987 | Alves |
| 4,659,714 A | 4/1987 | Watt-Smith |
| 4,661,359 A | 4/1987 | Seaborne et al. |
| 4,675,009 A | 6/1987 | Hymes et al. |
| 4,695,465 A | 9/1987 | Kigasawa et al. |
| 4,704,119 A | 11/1987 | Shaw et al. |
| 4,705,174 A | 11/1987 | Goglio |
| 4,712,460 A | 12/1987 | Allen et al. |
| 4,713,239 A | 12/1987 | Babaian et al. |
| 4,713,243 A | 12/1987 | Schiraldi et al. |
| 4,713,251 A | 12/1987 | Seighman |
| 4,716,802 A | 1/1988 | O'Connor et al. |
| 4,722,761 A | 2/1988 | Cartmell et al. |
| 4,727,064 A | 2/1988 | Pitha |
| 4,740,365 A | 4/1988 | Yukimatsu et al. |
| 4,748,022 A | 5/1988 | Busciglio |
| 4,752,465 A | 6/1988 | Mackles |
| 4,762,230 A | 8/1988 | Croce |
| 4,764,378 A | 8/1988 | Keith et al. |
| 4,765,983 A | 8/1988 | Takayanagi et al. |
| 4,772,470 A | 9/1988 | Inoue et al. |
| 4,777,046 A | 10/1988 | Iwakura et al. |
| 4,780,309 A | 10/1988 | Geria et al. |
| 4,781,294 A | 11/1988 | Croce |
| 4,787,517 A | 11/1988 | Martin |
| 4,789,667 A | 12/1988 | Makino et al. |
| 4,802,924 A | 2/1989 | Woznicki et al. |
| 4,828,841 A | 5/1989 | Porter et al. |
| 4,849,246 A | 7/1989 | Schmidt |
| 4,851,394 A | 7/1989 | Kubodera |
| 4,860,754 A | 8/1989 | Sharik et al. |
| 4,861,632 A | 8/1989 | Caggiano |
| RE33,093 E | 10/1989 | Schiraldi et al. |
| 4,872,270 A | 10/1989 | Fronheiser et al. |
| 4,876,092 A | 10/1989 | Mizobuchi et al. |
| 4,876,970 A | 10/1989 | Bolduc |
| 4,880,416 A | 11/1989 | Horiuchi et al. |
| 4,888,354 A | 12/1989 | Chang et al. |
| 4,894,232 A | 1/1990 | Reul et al. |
| 4,900,552 A | 2/1990 | Sanvordeker et al. |
| 4,900,554 A | 2/1990 | Yangibashi et al. |
| 4,900,556 A | 2/1990 | Wheatley et al. |
| 4,910,247 A | 3/1990 | Haldar et al. |
| 4,915,950 A | 4/1990 | Miranda et al. |
| 4,925,670 A | 5/1990 | Schmidt |
| 4,927,634 A | 5/1990 | Sorrentino et al. |
| 4,927,636 A | 5/1990 | Hijiya et al. |
| 4,929,447 A | 5/1990 | Yang |
| 4,937,078 A | 6/1990 | Mezei et al. |
| 4,940,587 A | 7/1990 | Jenkins et al. |
| 4,948,580 A | 8/1990 | Browning |
| 4,958,580 A | 9/1990 | Asaba et al. |
| 4,978,531 A | 12/1990 | Yamazaki et al. |
| 4,980,169 A | 12/1990 | Oppenheimer et al. |
| 4,981,693 A | 1/1991 | Higashi et al. |
| 4,981,875 A | 1/1991 | Leusner et al. |
| 4,993,586 A | 2/1991 | Taulbee et al. |
| 5,023,082 A | 6/1991 | Friedman et al. |
| 5,023,271 A | 6/1991 | Vigne et al. |
| 5,024,701 A | 6/1991 | Desmarais |
| 5,025,692 A | 6/1991 | Reynolds |
| 5,028,632 A | 7/1991 | Fuisz |
| 5,044,241 A | 9/1991 | Labrecque |
| 5,044,761 A | 9/1991 | Yuhki et al. |
| 5,045,445 A | 9/1991 | Schultz |
| 5,047,244 A | 9/1991 | Sanvordeker et al. |
| 5,049,322 A | 9/1991 | Devissaguet et al. |
| 5,056,584 A | 10/1991 | Seaton |
| 5,064,717 A | 11/1991 | Suzuki et al. |
| 5,072,842 A | 12/1991 | White |
| 5,078,734 A | 1/1992 | Noble |
| 5,089,307 A | 2/1992 | Ninomiya et al. |
| 5,100,591 A | 3/1992 | Leclef et al. |
| 5,107,734 A | 4/1992 | Armbruster |
| 5,116,140 A | 5/1992 | Hirashima |
| 5,118,508 A | 6/1992 | Kikuchi et al. |
| 5,126,160 A | 6/1992 | Giddey et al. |
| 5,137,729 A | 8/1992 | Kuroya et al. |
| 5,158,825 A | 10/1992 | Altwirth |
| 5,166,233 A | 11/1992 | Kuroya et al. |
| 5,176,705 A | 1/1993 | Noble |
| 5,184,771 A | 2/1993 | Jud et al. |
| 5,186,938 A | 2/1993 | Sablotsky et al. |
| 5,188,838 A | 2/1993 | Deleuil et al. |
| 5,196,436 A | 3/1993 | Smith |
| 5,229,164 A | 7/1993 | Pins et al. |
| 5,230,441 A | 7/1993 | Kaufman et al. |
| 5,234,957 A | 8/1993 | Mantelle |
| 5,264,024 A | 11/1993 | Bosvot et al. |
| 5,271,940 A | 12/1993 | Cleary et al. |
| 5,272,191 A | 12/1993 | Ibrahim et al. |
| 5,273,758 A | 12/1993 | Royce |
| 5,293,699 A | 3/1994 | Faust et al. |
| 5,316,717 A | 5/1994 | Koepff et al. |
| 5,325,968 A | 7/1994 | Sowden |
| 5,328,942 A | 7/1994 | Akhtar et al. |
| 5,344,676 A | 9/1994 | Kim et al. |
| 5,346,701 A | 9/1994 | Heiber et al. |
| 5,354,551 A | 10/1994 | Schmidt |
| 5,360,629 A | 11/1994 | Milbourn et al. |
| 5,369,131 A | 11/1994 | Poli et al. |
| 5,375,930 A | 12/1994 | Tani |
| 5,380,529 A | 1/1995 | Heusser et al. |
| 5,393,528 A | 2/1995 | Staab |
| 5,405,637 A | 4/1995 | Martinez et al. |
| 5,407,278 A | 4/1995 | Beer |
| 5,411,945 A | 5/1995 | Ozaki et al. |
| 5,413,792 A | 5/1995 | Ninomiya et al. |
| 5,422,127 A | 6/1995 | Dube et al. |
| 5,423,423 A | 6/1995 | Sato et al. |
| 5,433,960 A | 7/1995 | Meyers |
| 5,451,419 A | 9/1995 | Schwab et al. |
| 5,455,043 A | 10/1995 | Fischel-Ghodsian |
| 5,458,884 A | 10/1995 | Britton et al. |
| 5,462,749 A | 10/1995 | Rencher |
| 5,472,704 A | 12/1995 | Santus et al. |
| 5,479,408 A | 12/1995 | Will |
| 5,489,436 A | 2/1996 | Hoy et al. |
| 5,506,046 A | 4/1996 | Andersen et al. |
| 5,506,049 A | 4/1996 | Swei et al. |
| 5,518,902 A | 5/1996 | Ozaki et al. |
| 5,529,782 A | 6/1996 | Staab |
| 5,530,861 A | 6/1996 | Diamant et al. |
| 5,550,178 A | 8/1996 | Desai et al. |
| 5,551,033 A | 8/1996 | Foster et al. |
| 5,552,152 A | 9/1996 | Shen |
| 5,553,835 A | 9/1996 | Dresie et al. |
| 5,560,538 A | 10/1996 | Sato et al. |
| 5,567,237 A | 10/1996 | Kapp-Schwoerer et al. |

(56) References Cited

U.S. PATENT DOCUMENTS

| | | |
|---|---|---|
| 5,567,431 A | 10/1996 | Vert et al. |
| 5,573,783 A | 11/1996 | Desieno et al. |
| 5,582,342 A | 12/1996 | Jud |
| 5,587,175 A | 12/1996 | Viegas et al. |
| 5,588,009 A | 12/1996 | Will |
| 5,589,357 A | 12/1996 | Martinez et al. |
| 5,593,697 A | 1/1997 | Barr et al. |
| 5,595,980 A | 1/1997 | Brode et al. |
| 5,601,605 A | 2/1997 | Crowe et al. |
| 5,605,696 A | 2/1997 | Eury et al. |
| 5,605,698 A | 2/1997 | Ueno |
| 5,613,779 A | 3/1997 | Niwa |
| 5,614,212 A | 3/1997 | D'Angelo et al. |
| 5,620,757 A | 4/1997 | Ninomiya et al. |
| 5,629,003 A * | 5/1997 | Horstmann ............ A23G 3/343 424/401 |
| 5,629,021 A | 5/1997 | Wright |
| 5,633,006 A | 5/1997 | Catania et al. |
| 5,641,093 A | 6/1997 | Dolin et al. |
| 5,641,536 A | 6/1997 | Lech et al. |
| D380,836 S | 7/1997 | Fitzpatrick et al. |
| 5,647,431 A | 7/1997 | Takeshita et al. |
| 5,653,993 A | 8/1997 | Ghanta et al. |
| 5,656,296 A | 8/1997 | Khan et al. |
| 5,656,297 A | 8/1997 | Bernstein et al. |
| 5,670,168 A | 9/1997 | Baichwal et al. |
| 5,679,145 A | 10/1997 | Andersen et al. |
| 5,681,873 A | 10/1997 | Norton et al. |
| 5,689,550 A | 11/1997 | Garson et al. |
| 5,698,181 A | 12/1997 | Luo |
| 5,698,217 A | 12/1997 | Wilking |
| 5,700,478 A | 12/1997 | Biegajski et al. |
| 5,700,479 A | 12/1997 | Lundgren |
| 5,725,648 A | 3/1998 | Brown et al. |
| 5,733,575 A | 3/1998 | Mehra et al. |
| 5,738,211 A | 4/1998 | Ichino et al. |
| 5,742,905 A | 4/1998 | Pepe et al. |
| 5,750,145 A | 5/1998 | Patell |
| 5,750,157 A | 5/1998 | Grosswald et al. |
| 5,750,585 A | 5/1998 | Park et al. |
| 5,759,599 A | 6/1998 | Wampler et al. |
| 5,761,525 A | 6/1998 | Williams |
| 5,764,639 A | 6/1998 | Staples et al. |
| 5,764,899 A | 6/1998 | Eggleston et al. |
| 5,765,004 A | 6/1998 | Foster et al. |
| 5,766,332 A | 6/1998 | Graves et al. |
| 5,766,525 A | 6/1998 | Andersen et al. |
| 5,766,620 A | 6/1998 | Heiber et al. |
| 5,766,839 A | 6/1998 | Johnson et al. |
| 5,771,353 A | 6/1998 | Eggleston et al. |
| 5,785,180 A | 7/1998 | Dressel et al. |
| 5,792,494 A | 8/1998 | Kanca et al. |
| 5,800,832 A | 9/1998 | Tapolsky et al. |
| 5,806,284 A | 9/1998 | Gifford |
| 5,815,398 A | 9/1998 | Dighe et al. |
| 5,822,526 A | 10/1998 | Waskiewicz |
| 5,830,437 A | 11/1998 | Ascione et al. |
| 5,830,884 A | 11/1998 | Kasica et al. |
| 5,846,557 A | 12/1998 | Eisenstadt et al. |
| 5,847,023 A | 12/1998 | Viegas et al. |
| 5,862,915 A | 1/1999 | Plezia et al. |
| 5,864,684 A | 1/1999 | Nielsen |
| 5,881,476 A | 3/1999 | Strobush et al. |
| 5,891,461 A | 4/1999 | Jona et al. |
| 5,891,845 A | 4/1999 | Myers |
| 5,894,930 A | 4/1999 | Faughey et al. |
| 5,900,247 A | 5/1999 | Rault et al. |
| 5,906,742 A | 5/1999 | Wang et al. |
| 5,930,914 A | 8/1999 | Johansson et al. |
| 5,937,161 A | 8/1999 | Mulligan et al. |
| 5,941,393 A | 8/1999 | Wilfong, Jr. |
| 5,945,651 A | 8/1999 | Chorosinski et al. |
| 5,948,430 A | 9/1999 | Zerbe et al. |
| 5,955,097 A | 9/1999 | Tapolsky et al. |
| 5,965,154 A | 10/1999 | Haralambopoulos |
| 5,980,554 A | 11/1999 | Lenker et al. |
| 5,992,742 A | 11/1999 | Sullivan et al. |
| 5,995,597 A | 11/1999 | Woltz et al. |
| 6,004,996 A | 12/1999 | Shah et al. |
| 6,024,975 A | 2/2000 | D'Angelo et al. |
| 6,030,616 A | 2/2000 | Waters et al. |
| 6,031,895 A | 2/2000 | Cohn et al. |
| 6,036,016 A | 3/2000 | Arnold |
| 6,047,484 A | 4/2000 | Bolland et al. |
| 6,051,253 A | 4/2000 | Zettler et al. |
| 6,054,119 A | 4/2000 | Hurme et al. |
| 6,064,990 A | 5/2000 | Goldsmith |
| 6,072,100 A | 6/2000 | Mooney et al. |
| 6,074,097 A | 6/2000 | Hayashi et al. |
| 6,077,558 A | 6/2000 | Euber |
| 6,090,401 A | 7/2000 | Gowan, Jr. et al. |
| 6,099,871 A | 8/2000 | Martinez |
| 6,103,266 A | 8/2000 | Tapolsky et al. |
| 6,106,930 A | 8/2000 | Ludwig |
| 6,143,276 A | 11/2000 | Unger |
| 6,148,708 A | 11/2000 | Pfeiffer |
| 6,152,007 A | 11/2000 | Sato |
| 6,153,210 A | 11/2000 | Roberts et al. |
| 6,153,220 A | 11/2000 | Cumming et al. |
| 6,159,498 A | 12/2000 | Tapolsky et al. |
| 6,161,129 A | 12/2000 | Rochkind |
| 6,177,066 B1 | 1/2001 | Pataut et al. |
| 6,177,092 B1 | 1/2001 | Lentini et al. |
| 6,177,096 B1 | 1/2001 | Zerbe et al. |
| 6,183,808 B1 | 2/2001 | Grillo et al. |
| 6,197,329 B1 | 3/2001 | Hermelin et al. |
| 6,203,566 B1 | 3/2001 | Alanen et al. |
| 6,219,694 B1 | 4/2001 | Lazaridis et al. |
| 6,221,402 B1 | 4/2001 | Itoh et al. |
| 6,227,359 B1 | 5/2001 | Truluck |
| 6,230,894 B1 | 5/2001 | Danville |
| 6,231,957 B1 | 5/2001 | Zerbe et al. |
| 6,238,700 B1 | 5/2001 | Dohner et al. |
| 6,264,981 B1 | 7/2001 | Zhang et al. |
| 6,267,808 B1 | 7/2001 | Grillo et al. |
| 6,268,048 B1 | 7/2001 | Topolkaraev et al. |
| 6,284,264 B1 | 9/2001 | Zerbe et al. |
| 6,287,595 B1 | 9/2001 | Loewy et al. |
| 6,294,206 B1 | 9/2001 | Barrett-Reis et al. |
| 6,311,627 B1 | 11/2001 | Draper et al. |
| 6,338,407 B2 | 1/2002 | Danville |
| 6,344,088 B1 | 2/2002 | Kamikihara et al. |
| 6,374,715 B1 | 4/2002 | Takatsuka |
| 6,375,963 B1 | 4/2002 | Repka et al. |
| 6,391,294 B1 | 5/2002 | Dettmar et al. |
| 6,394,306 B1 | 5/2002 | Pawlo et al. |
| 6,395,299 B1 | 5/2002 | Babich et al. |
| 6,413,792 B1 | 7/2002 | Sauer et al. |
| 6,419,903 B1 | 7/2002 | Xu et al. |
| 6,419,906 B1 | 7/2002 | Xu et al. |
| 6,428,825 B2 | 8/2002 | Sharma et al. |
| 6,432,460 B1 | 8/2002 | Zietlow et al. |
| 6,436,464 B1 | 8/2002 | Euber |
| 6,454,788 B1 | 9/2002 | Ashton |
| 6,467,621 B1 | 10/2002 | Ishida |
| 6,468,516 B1 | 10/2002 | Geria et al. |
| 6,472,003 B2 | 10/2002 | Barrett-Reis et al. |
| 6,482,517 B1 | 11/2002 | Anderson |
| 6,488,963 B1 | 12/2002 | McGinity et al. |
| 6,495,599 B2 | 12/2002 | Auestad et al. |
| 6,503,532 B1 | 1/2003 | Murty et al. |
| 6,509,072 B2 | 1/2003 | Bening et al. |
| 6,534,090 B2 | 3/2003 | Puthli et al. |
| 6,534,092 B2 | 3/2003 | Wright et al. |
| 6,552,024 B1 | 4/2003 | Chen et al. |
| 6,562,375 B1 | 5/2003 | Sako et al. |
| 6,575,999 B1 | 6/2003 | Rohrig |
| 6,589,576 B2 | 7/2003 | Borschel et al. |
| 6,592,887 B2 | 7/2003 | Zerbe et al. |
| 6,596,298 B2 | 7/2003 | Leung et al. |
| 6,596,302 B2 | 7/2003 | O'Connor et al. |
| 6,599,542 B1 | 7/2003 | Abdel-Malik et al. |
| 6,610,338 B2 | 8/2003 | Tang |
| 6,620,440 B1 | 9/2003 | Hsia et al. |

(56) References Cited

U.S. PATENT DOCUMENTS

| | | |
|---|---|---|
| 6,655,112 B1 | 12/2003 | Cremer et al. |
| 6,656,493 B2 | 12/2003 | Dzija et al. |
| 6,660,292 B2 | 12/2003 | Zerbe et al. |
| 6,667,060 B1 | 12/2003 | Vandecruys et al. |
| 6,668,839 B2 | 12/2003 | Williams |
| 6,708,826 B1 | 3/2004 | Ginsberg et al. |
| 6,709,671 B2 | 3/2004 | Zerbe et al. |
| 6,720,006 B2 | 4/2004 | Hanke et al. |
| 6,726,054 B2 | 4/2004 | Fagen et al. |
| 6,730,319 B2 | 5/2004 | Maeder et al. |
| 6,752,824 B2 | 6/2004 | Yancy |
| 6,776,157 B2 | 8/2004 | Williams et al. |
| 6,797,283 B1 | 9/2004 | Edgren et al. |
| 6,800,329 B2 | 10/2004 | Horstmann et al. |
| 6,824,829 B2 | 11/2004 | Berry et al. |
| 6,865,860 B2 | 3/2005 | Arakawa et al. |
| 6,905,016 B2 | 6/2005 | Kanios et al. |
| 6,913,766 B1 | 7/2005 | Krumme et al. |
| 6,929,399 B2 | 8/2005 | Nokura |
| 6,929,400 B2 | 8/2005 | Razeti et al. |
| 7,005,142 B2 | 2/2006 | Leon et al. |
| 7,040,503 B2 | 5/2006 | Leichter et al. |
| 7,067,116 B1 | 6/2006 | Bess et al. |
| 7,093,736 B2 | 8/2006 | Maietta et al. |
| 7,115,507 B2 | 10/2006 | Kawase |
| 7,179,788 B2 | 2/2007 | DeFelippis et al. |
| 7,241,411 B2 | 7/2007 | Berry et al. |
| 7,357,891 B2 | 4/2008 | Yang et al. |
| 7,390,503 B1 | 6/2008 | Ahmed et al. |
| 7,425,292 B2 | 9/2008 | Yang et al. |
| 7,428,859 B2 | 9/2008 | Fujita et al. |
| 7,484,640 B2 | 2/2009 | von Falkenhausen et al. |
| 7,531,191 B2 | 5/2009 | Zion et al. |
| 7,579,019 B2 | 8/2009 | Tapolsky et al. |
| 7,591,801 B2 | 9/2009 | Brauker et al. |
| 7,665,896 B1 | 2/2010 | Higgs |
| 7,666,337 B2 | 2/2010 | Yang et al. |
| 7,694,617 B2 | 4/2010 | Habra et al. |
| 7,824,588 B2 | 11/2010 | Yang et al. |
| 7,910,031 B2 | 3/2011 | Yang et al. |
| 8,017,150 B2 | 9/2011 | Yang et al. |
| 8,051,983 B2 | 11/2011 | Simon et al. |
| 8,147,866 B2 | 4/2012 | Finn et al. |
| 2001/0006677 A1 | 7/2001 | McGinity et al. |
| 2001/0022964 A1 | 9/2001 | Leung et al. |
| 2001/0046511 A1 | 11/2001 | Zerbe et al. |
| 2002/0006677 A1 | 1/2002 | Egermeier et al. |
| 2002/0012689 A1 | 1/2002 | Stillman |
| 2002/0045582 A1 | 4/2002 | Margolin et al. |
| 2002/0098198 A1 | 7/2002 | Watts et al. |
| 2002/0104774 A1 | 8/2002 | Hammond |
| 2002/0127254 A1 | 9/2002 | Fotinos et al. |
| 2002/0131990 A1 | 9/2002 | Barkalow et al. |
| 2002/0147201 A1 | 10/2002 | Chen et al. |
| 2002/0170567 A1 | 11/2002 | Rizzotto et al. |
| 2002/0177380 A1 | 11/2002 | Forman et al. |
| 2003/0035841 A1 | 2/2003 | Dzija et al. |
| 2003/0044511 A1 | 3/2003 | Zerbe et al. |
| 2003/0054039 A1 | 3/2003 | Zyck et al. |
| 2003/0068378 A1 | 4/2003 | Chen et al. |
| 2003/0069263 A1 | 4/2003 | Breder et al. |
| 2003/0072865 A1 | 4/2003 | Bindels et al. |
| 2003/0077315 A1 | 4/2003 | Lee et al. |
| 2003/0107149 A1 | 6/2003 | Yang et al. |
| 2003/0118649 A1 | 6/2003 | Gao et al. |
| 2003/0121932 A1 | 7/2003 | Wajda |
| 2003/0124176 A1 | 7/2003 | Hsu et al. |
| 2003/0140760 A1 | 7/2003 | Bory |
| 2003/0147956 A1 | 8/2003 | Shefer et al. |
| 2003/0161926 A1 | 8/2003 | Kemp et al. |
| 2003/0183643 A1 | 10/2003 | Fagen et al. |
| 2003/0224044 A1 | 12/2003 | Weibel |
| 2004/0013731 A1 | 1/2004 | Chen et al. |
| 2004/0024003 A1 | 2/2004 | Asmussen et al. |
| 2004/0044367 A1 | 3/2004 | Yancy |
| 2004/0058457 A1 | 3/2004 | Huang et al. |
| 2004/0091677 A1 | 5/2004 | Topolkaraev |
| 2004/0096569 A1 | 5/2004 | Barkalow et al. |
| 2004/0102867 A1 | 5/2004 | Palanisamy et al. |
| 2004/0111275 A1 | 6/2004 | Kroll et al. |
| 2004/0120991 A1 | 6/2004 | Gardner et al. |
| 2004/0136924 A1 | 7/2004 | Boyd et al. |
| 2004/0137458 A1 | 7/2004 | Archambault et al. |
| 2004/0156901 A1 | 8/2004 | Thakur et al. |
| 2004/0191302 A1 | 9/2004 | Davidson |
| 2004/0209057 A1 | 10/2004 | Enlow et al. |
| 2004/0219109 A1 | 11/2004 | Hatch |
| 2004/0241242 A1 | 12/2004 | Fuisz et al. |
| 2005/0003048 A1 | 1/2005 | Pearce et al. |
| 2005/0011776 A1 | 1/2005 | Nagel |
| 2005/0019588 A1 | 1/2005 | Berry et al. |
| 2005/0035133 A1 | 2/2005 | Gerulski et al. |
| 2005/0037055 A1 | 2/2005 | Yang et al. |
| 2005/0048102 A1 | 3/2005 | Tapolsky et al. |
| 2005/0055123 A1 | 3/2005 | Franz |
| 2005/0089548 A1 | 4/2005 | Virgalitto et al. |
| 2005/0095272 A1 | 5/2005 | Augello |
| 2005/0115862 A1 | 6/2005 | Maietta |
| 2005/0118217 A1 | 6/2005 | Barnhart et al. |
| 2005/0118271 A1 | 6/2005 | Schliecker et al. |
| 2005/0136115 A1 | 6/2005 | Kulkarni et al. |
| 2005/0147658 A1 | 7/2005 | Tapolsky et al. |
| 2005/0163714 A1 | 7/2005 | Sukhishvili et al. |
| 2005/0170138 A1 | 8/2005 | Berry |
| 2005/0191349 A1 | 9/2005 | Boehm et al. |
| 2005/0192309 A1 | 9/2005 | Palermo et al. |
| 2005/0214251 A1 | 9/2005 | Pohl et al. |
| 2005/0222781 A1 | 10/2005 | Yue et al. |
| 2005/0232977 A1 | 10/2005 | Khan et al. |
| 2005/0239845 A1 | 10/2005 | Proehl et al. |
| 2006/0023976 A1 | 2/2006 | Alvater et al. |
| 2006/0039958 A1 | 2/2006 | Fuisz et al. |
| 2006/0071057 A1 | 4/2006 | Aschenbrenner et al. |
| 2006/0073190 A1 | 4/2006 | Carroll et al. |
| 2006/0083786 A1 | 4/2006 | Chaudhari et al. |
| 2006/0093679 A1 | 5/2006 | Mayer et al. |
| 2006/0104910 A1 | 5/2006 | Lerner |
| 2006/0147493 A1 | 7/2006 | Yang et al. |
| 2006/0163269 A1 | 7/2006 | Anderson et al. |
| 2006/0180604 A1 | 8/2006 | Ginsberg et al. |
| 2006/0182796 A1 | 8/2006 | Wu et al. |
| 2006/0189772 A1 | 8/2006 | Scheibel et al. |
| 2006/0198790 A1 | 9/2006 | Dugger, III et al. |
| 2006/0198885 A1 | 9/2006 | Dharmadhikari et al. |
| 2006/0210610 A1 | 9/2006 | Davidson et al. |
| 2006/0213348 A1 | 9/2006 | Loibl |
| 2006/0215941 A1 | 9/2006 | Golbert |
| 2006/0246141 A1 | 11/2006 | Liversidge et al. |
| 2006/0264448 A1 | 11/2006 | Pryde |
| 2006/0281775 A1 | 12/2006 | Kelly, II et al. |
| 2006/0286108 A1 | 12/2006 | Bell |
| 2007/0027213 A1 | 2/2007 | Oberegger et al. |
| 2007/0045148 A1 | 3/2007 | Saclier et al. |
| 2007/0069416 A1 | 3/2007 | Yang et al. |
| 2007/0087036 A1 | 4/2007 | Durschlag et al. |
| 2007/0098746 A1 | 5/2007 | Nichols et al. |
| 2007/0122455 A1 | 5/2007 | Myers et al. |
| 2007/0138049 A1 | 6/2007 | Bitner |
| 2007/0148097 A1 | 6/2007 | Finn et al. |
| 2007/0170196 A1 | 7/2007 | Libohova et al. |
| 2007/0205127 A1 | 9/2007 | Barndt et al. |
| 2007/0231368 A1 | 10/2007 | Wang et al. |
| 2007/0267433 A1 | 11/2007 | Fuisz et al. |
| 2007/0281003 A1 | 12/2007 | Fuisz et al. |
| 2008/0044454 A1 | 2/2008 | Yang et al. |
| 2008/0073235 A1 | 3/2008 | Harada et al. |
| 2008/0075825 A1 | 3/2008 | Fuisz et al. |
| 2008/0081071 A1 | 4/2008 | Sanghvi et al. |
| 2008/0105582 A1 | 5/2008 | Ludwig et al. |
| 2008/0233174 A1 | 9/2008 | Myers et al. |
| 2008/0242558 A1 | 10/2008 | Belcher et al. |
| 2008/0242736 A1 | 10/2008 | Fuisz |
| 2008/0254105 A1 | 10/2008 | Tapolsky et al. |
| 2008/0260805 A1 | 10/2008 | Yang et al. |

(56) References Cited

U.S. PATENT DOCUMENTS

| | | |
|---|---|---|
| 2008/0260809 A1 | 10/2008 | Yang et al. |
| 2008/0268116 A1 | 10/2008 | Kring |
| 2008/0290106 A1 | 11/2008 | van der Klaauw et al. |
| 2008/0299197 A1 | 12/2008 | Toneguzzo et al. |
| 2008/0300173 A1 | 12/2008 | DeFrees |
| 2008/0308449 A1 | 12/2008 | Intini |
| 2009/0004254 A1 | 1/2009 | Maibach |
| 2009/0009332 A1 | 1/2009 | Nunez et al. |
| 2009/0014491 A1 | 1/2009 | Fuisz et al. |
| 2009/0029074 A1 | 1/2009 | Sasine et al. |
| 2009/0074333 A1 | 3/2009 | Griebel et al. |
| 2009/0104270 A1 | 4/2009 | Myers et al. |
| 2009/0146336 A1 | 6/2009 | Masi |
| 2009/0181075 A1 | 7/2009 | Gordon et al. |
| 2009/0192075 A1 | 7/2009 | Steiner |
| 2009/0196907 A1 | 8/2009 | Bunick et al. |
| 2009/0297614 A1 | 12/2009 | Rademacher et al. |
| 2010/0015128 A1 | 1/2010 | Lee et al. |
| 2010/0087470 A1 | 4/2010 | Oksche et al. |
| 2010/0092545 A1 | 4/2010 | Yang et al. |
| 2010/0178254 A1 | 7/2010 | Hariharan et al. |
| 2010/0221309 A1 | 9/2010 | Myers et al. |
| 2010/0297232 A1 | 11/2010 | Myers et al. |
| 2011/0189259 A1 | 8/2011 | Vasisht et al. |
| 2011/0262522 A1 | 10/2011 | Finn et al. |

FOREIGN PATENT DOCUMENTS

| | | |
|---|---|---|
| CA | 2317491 C | 6/2008 |
| CH | 639619 A5 | 11/1983 |
| CN | 1118254 A | 3/1996 |
| DE | 2746414 A1 | 4/1979 |
| DE | 2449865 B2 | 6/1981 |
| DE | 2432925 C3 | 11/1985 |
| DE | 3630603 C2 | 6/1989 |
| DE | 19646392 A1 | 5/1998 |
| DE | 202004003781 U1 | 5/2004 |
| EP | 0014253 A2 | 8/1980 |
| EP | 0021178 B1 | 1/1981 |
| EP | 0090560 A2 | 10/1983 |
| EP | 0095892 A1 | 12/1983 |
| EP | 0065370 B1 | 1/1985 |
| EP | 0248548 B1 | 5/1987 |
| EP | 0232877 A2 | 8/1987 |
| EP | 0241178 | 10/1987 |
| EP | 0285568 A2 | 3/1988 |
| EP | 0274431 A2 | 7/1988 |
| EP | 0219762 B1 | 12/1990 |
| EP | 0259749 B1 | 8/1991 |
| EP | 0200508 B1 | 10/1991 |
| EP | 0241178 B1 | 1/1992 |
| EP | 0514691 A2 | 4/1992 |
| EP | 0273069 B1 | 10/1992 |
| EP | 0250187 B1 | 9/1993 |
| EP | 0452446 B1 | 12/1993 |
| EP | 0598606 A1 | 5/1994 |
| EP | 0381194 B1 | 8/1994 |
| EP | 0440462 B1 | 12/1994 |
| EP | 0636364 A1 | 1/1995 |
| EP | 0450141 B1 | 5/1995 |
| EP | 0460588 B1 | 8/1995 |
| EP | 0514691 B1 | 1/1996 |
| EP | 0598606 B1 | 6/1999 |
| EP | 1143940 | 7/2000 |
| EP | 1110546 A1 | 6/2001 |
| EP | 1177788 A2 | 2/2002 |
| EP | 1219291 A1 | 3/2002 |
| EP | 1243523 A1 | 9/2002 |
| EP | 0949925 B1 | 1/2004 |
| EP | 1504765 A1 | 2/2005 |
| EP | 1267829 B1 | 5/2006 |
| EP | 1674078 A2 | 6/2006 |
| EP | 1852041 A2 | 11/2007 |
| EP | 1897543 A1 | 3/2008 |
| EP | 1591106 B1 | 7/2009 |
| EP | 2105389 A1 | 9/2009 |
| EP | 2253224 A1 | 11/2010 |
| EP | 2305310 A1 | 4/2011 |
| FR | 2716098 A1 | 8/1995 |
| GB | 1061557 | 3/1967 |
| GB | 1154317 | 6/1969 |
| GB | 1510999 | 5/1978 |
| GB | 2166651 A | 5/1986 |
| GB | 2447016 A | 9/2009 |
| JP | 56100714 A | 8/1981 |
| JP | 62126950 A | 6/1987 |
| JP | 2265444 A | 10/1990 |
| JP | 473268 A | 3/1992 |
| JP | 5147140 A | 6/1993 |
| JP | 7322812 A | 12/1995 |
| JP | 11255247 A | 9/1999 |
| JP | 2000159658 A | 6/2000 |
| JP | 2001048196 A | 2/2001 |
| JP | 2001225851 A | 8/2001 |
| JP | 2001279100 A | 10/2001 |
| JP | 2003312688 A | 11/2003 |
| JP | 2004222663 A | 8/2004 |
| JP | 2006143335 A | 6/2006 |
| JP | 2008011194 A | 1/2008 |
| WO | 1988007103 | 9/1988 |
| WO | 9105540 A1 | 5/1991 |
| WO | 1992012704 | 8/1992 |
| WO | 9215289 A1 | 9/1992 |
| WO | 9505416 A2 | 2/1995 |
| WO | 9518046 A1 | 7/1995 |
| WO | 1995023596 | 9/1995 |
| WO | 9530601 A1 | 11/1995 |
| WO | 9615903 A1 | 5/1996 |
| WO | 9625150 A1 | 8/1996 |
| WO | 1996025638 | 8/1996 |
| WO | 9731621 A1 | 9/1997 |
| WO | 9732573 A1 | 9/1997 |
| WO | 1997044016 | 11/1997 |
| WO | 9810993 A1 | 3/1998 |
| WO | 9817251 A1 | 4/1998 |
| WO | 1998014179 | 4/1998 |
| WO | 9935051 A1 | 7/1999 |
| WO | 9955312 A2 | 11/1999 |
| WO | 200002536 | 1/2000 |
| WO | 2000002955 | 1/2000 |
| WO | 0018365 A2 | 4/2000 |
| WO | 2000/027618 A1 | 5/2000 |
| WO | 0024647 A1 | 5/2000 |
| WO | 0042992 A2 | 7/2000 |
| WO | 2000057858 | 10/2000 |
| WO | 2001003917 A2 | 1/2001 |
| WO | 0130288 A1 | 5/2001 |
| WO | 2001034121 | 5/2001 |
| WO | 0143728 A1 | 6/2001 |
| WO | 0156904 A1 | 8/2001 |
| WO | 0168452 A1 | 9/2001 |
| WO | 0170194 A1 | 9/2001 |
| WO | 0170197 A2 | 9/2001 |
| WO | 0191721 A2 | 12/2001 |
| WO | 0205789 A2 | 1/2002 |
| WO | 0207711 A1 | 1/2002 |
| WO | 2002005820 A1 | 1/2002 |
| WO | 2006017462 A2 | 2/2002 |
| WO | 0243657 A2 | 6/2002 |
| WO | 2002/064148 A2 | 8/2002 |
| WO | 02062315 A1 | 8/2002 |
| WO | 02074238 A2 | 9/2002 |
| WO | 02091965 A1 | 11/2002 |
| WO | 03011259 A1 | 2/2003 |
| WO | 03015749 A1 | 2/2003 |
| WO | 03030881 A1 | 4/2003 |
| WO | 03030882 A1 | 4/2003 |
| WO | 03030883 A1 | 4/2003 |
| WO | 03043659 A1 | 5/2003 |
| WO | 2003/101357 A1 | 12/2003 |
| WO | 2004009445 A2 | 1/2004 |
| WO | 2004035407 A1 | 4/2004 |
| WO | 2004043165 A1 | 5/2004 |
| WO | 2004045305 A2 | 6/2004 |

(56) References Cited

FOREIGN PATENT DOCUMENTS

| | | |
|---|---|---|
| WO | 2004045537 A2 | 6/2004 |
| WO | 2004052335 A1 | 6/2004 |
| WO | 2004060298 A2 | 7/2004 |
| WO | 2004087084 A1 | 10/2004 |
| WO | 2004113193 A1 | 12/2004 |
| WO | 2005020933 A2 | 3/2005 |
| WO | 2005035776 A2 | 4/2005 |
| WO | 2005039499 A2 | 5/2005 |
| WO | 2005074867 A1 | 8/2005 |
| WO | 2005102287 A2 | 11/2005 |
| WO | 2005102863 A1 | 11/2005 |
| WO | 2005123074 A1 | 12/2005 |
| WO | 2006004480 A1 | 1/2006 |
| WO | 2006031209 A1 | 3/2006 |
| WO | 2006037979 A2 | 4/2006 |
| WO | 2006039264 A1 | 4/2006 |
| WO | 2006037425 A1 | 8/2006 |
| WO | 2006085210 A1 | 8/2006 |
| WO | 2006133948 A2 | 12/2006 |
| WO | 2007015105 A2 | 2/2007 |
| WO | 2007067494 A1 | 6/2007 |
| WO | 2007070632 A2 | 6/2007 |
| WO | 2008011194 A2 | 1/2008 |
| WO | 2008025791 A1 | 3/2008 |
| WO | 2008036299 A2 | 3/2008 |
| WO | 2008040534 A2 | 4/2008 |
| WO | 2009044118 A2 | 4/2009 |
| WO | 2009052421 A1 | 4/2009 |
| WO | 2009027625 A2 | 5/2009 |
| WO | 2009105540 A1 | 8/2009 |

OTHER PUBLICATIONS

Index of Documents for Inter Partes Review Case No. IPR2013-00316, current as of Jun. 18, 2019.
Transaction History for Ex Parte Reexamination Control No. 90/012,097, current as of Jun. 18, 2019.
Index of Documents for Inter Partes Review Case No. IPR2013-00315, current as of Jun. 18, 2019.
Transaction History for Ex Parte Reexamination Control No. 95/002,171, current as of Jun. 18, 2019.
Transaction History for Ex Parte Reexamination Control No. 95/001,753, current as of Jun. 18, 2019.
Transaction History for Ex Parte Reexamination Control No. 95/002,170, current as of Jun. 18, 2019.
Index of Documents for Inter Partes Review Case No. IPR2014-00794, current as of Jun. 18, 2019.
Index of Documents for Inter Partes Review Case No. IPR2015-00165, current as of Jun. 18, 2019.
Index of Documents for Inter Partes Review Case No. IPR2015-00167, current as of Jun. 18, 2019.
Index of Documents for Inter Partes Review Case No. IPR2015-00168, current as of Jun. 18, 2019.
Index of Documents for Inter Partes Review Case No. IPR2015-00169, current as of Jun. 18, 2019.
Index of Documents for Inter Partes Review Case No. IPR2016-00281, current as of Jun. 18, 2019.
Index of Documents for Inter Partes Review Case No. IPR2016-00282, current as of Jun. 18, 2019.
Index of Documents for Inter Partes Review Case No. IPR2016-01111, current as of Jun. 18, 2019.
Index of Documents for Inter Partes Review Case No. IPR2016-01112, current as of Jun. 18, 2019.
Index of Documents for Inter Partes Review Case No. IPR2017-00200, current as of Jun. 18, 2019.
Index of Documents for Inter Partes Review Case No. IPR2017-01557, current as of Jun. 18, 2019.
Index of Documents for Inter Partes Review Case No. IPR2017-01582, current as of Jun. 18, 2019.
Index of Documents for Inter Partes Review Case No. IPR2017-01949, current as of Jun. 18, 2019.
Verdampfung, Kristallisation, Trocknung (Gnielinski, V. et al., (Eds.)), pp. 161-181 (Vieweg & Sohn Verlagsgsellschaft mbH 1993). (partial English translation included.).
Giunchedi, P. and Conte, U., "Spray-drying as a preparation method of microparticulate drug delivery systems : an overview," S.T.P. Pharma. Sciences 6(4):276-290 (1995).
Guo, J.H. and Zerbe, H., "Water Soluble Film for Oral Administration," The 24th International Symposium on Controlled Release of Bioactive Materials, pp. 227-229 (Paper No. 5001-5003) (1997).
The Theory and Practice of Industrial Pharmacy (3rd Ed.) (Lachman, L et al. (eds.)), pp. 47-48, 51, 57, 64, 123-127, 346-369, 453-454, 461, 470, 479, 484, 491-492, 654-655 (1986).
Physical Pharmacy (4th Ed.) (Martin, A. et al. (eds.)), pp. 423, 430-434, 453, 461, 484, 557-558, 560, 565-567 (1993).
Bioadhesive Drug Delivery Systems (Lenaerts, V. and Gurny, R. (eds.)), Ch. 6, pp. 106-136 (1990).
Introductory Polymer Chemistry (Misra, G.S. (ed.)), Ch. 6, pp. 98-118 (1993).
Nishaoka, Y. et al., "Laser Diffraction Estimation of Particle Size Distribution of Slightly Water-Soluble Drugs Coexisting with Additives: Application to Solid Dosage Forms," Chem. Pharm. Bull. 40(6):1563-1568 (1992).
Perumal, V.A. and Govender, T., "Investigating a New Approach to Film Casting for Enhanced Drug Content Uniformity in Polymeric Films," Drug Development and Industrial Pharmacy, 34:1034-1047 (2008).
Remington's Pharmaceutical Sciences (17th Ed.) (Gennaro, A.R. (ed.)), Ch. 37, pp. 713-740 (1985).
Shu, X.Z., et al., "Novel pH-sensitive citrate cross-linked chitosan film drug controlled release," Int. J. Pharmaceutics 212:19-28 (2001).
Webster's Third New International Dictionary, "evenly", 1963, G & C Merriam Company, p. 787.
U.S. Pat. No. 7,357,891, 90/012,098, Ex Parte Reexamination.
U.S. Pat. No. 7,357,891, IPR2013-00316, Inter Partes Review.
U.S. Pat. No. 7,425,292, 90/012,097, Ex Parte Reexamination.
U.S. Pat. No. 7,425,292, IPR2013-00315, Inter Partes Review.
U.S. Pat. No. 7,666,337, 95/002,171, Ex Parte Reexamination.
U.S. Pat. No. 7,824,588, 95/001,753, Ex Parte Reexamination.
U.S. Pat. No. 7,897,080, 95/002,170, Ex Parte Reexamination.
U.S. Pat. No. 8,017,150, IPR2016-00282, Inter Partes Review.
U.S. Pat. No. 8,603,514, IPR2016-00281, Inter Partes Review.
U.S. Pat. No. 8,652,378, IPR2014-00794, Inter Partes Review.
U.S. Pat. No. 8,765,167, IPR2015-00165, Inter Partes Review.
U.S. Pat. No. 8,765,167, IPR2015-00167, Inter Partes Review.
U.S. Pat. No. 8,765,167, IPR2015-00168, Inter Partes Review.
U.S. Pat. No. 8,765,167, IPR2015-00169, Inter Partes Review.
U.S. Pat. No. 8,603,514, IPR2016-01111, Inter Partes Review.
U.S. Pat. No. 8,017,150, IPR2016-01112, Inter Partes Review.
U.S. Pat. No. 8,603,514, IPR2017-00200, Inter Partes Review.
U.S. Pat. No. 8,603,514, IPR2017-01557, Inter Partes Review.
U.S. Pat. No. 8,603,514, IPR2017-01582, Inter Partes Review.
U.S. Pat. No. 8,900,497, IPR2017-01949, Inter Partes Review.
U.S. Appl. No. 10/074,272, filed Feb. 14, 2002.
U.S. Appl. No. 10/768,809, filed Jan. 30, 2004.
U.S. Appl. No. 10/856,176, filed May 28, 2004.
U.S. Appl. No. 11/092,217, filed Mar. 29, 2005.
U.S. Appl. No. 11/237,525, filed Sep. 28, 2005.
U.S. Appl. No. 11/473,356, filed Jun. 22, 2006.
U.S. Appl. No. 11/517,982, filed Sep. 8, 2006.
U.S. Appl. No. 11/526,996, filed Sep. 26, 2006.
U.S. Appl. No. 11/634,280, filed Dec. 5, 2006.
U.S. Appl. No. 11/639,013, filed Dec. 14, 2006.
U.S. Appl. No. 11/674,223, filed Feb. 13, 2007.
U.S. Appl. No. 11/775,484, filed Jul. 10, 2007.
U.S. Appl. No. 12/102,071, filed Apr. 14, 2008.
U.S. Appl. No. 12/128,950, filed May 29, 2008.
U.S. Appl. No. 12/107,389, filed Apr. 22, 2008.
U.S. Appl. No. 12/171,692, filed Jul. 11, 2008.
U.S. Appl. No. 12/411,505, filed Mar. 26, 2009.
U.S. Appl. No. 12/411,835, filed Mar. 26, 2009.
U.S. Appl. No. 12/575,261, filed Oct. 7, 2009.
U.S. Appl. No. 12/614,928, filed Nov. 9, 2009.

(56) References Cited

OTHER PUBLICATIONS

U.S. Appl. No. 12/779,316, filed May 13, 2010.
U.S. Appl. No. 13/035,328, filed Feb. 25, 2011.
U.S. Appl. No. 13/052,655, filed Mar. 21, 2011.
U.S. Appl. No. 13/342,614, filed Feb. 12, 2012.
U.S. Appl. No. 13/096,996, filed Apr. 28, 2011.
U.S. Appl. No. 13/853,237, filed Mar. 29, 2013.
U.S. Appl. No. 13/853,223, filed Mar. 29, 2013.
U.S. Appl. No. 13/853,253, filed Mar. 29, 2013.
U.S. Appl. No. 13/853,276, filed Mar. 29, 2013.
U.S. Appl. No. 13/853,290, filed Mar. 29, 2013.
U.S. Appl. No. 13/890,542, filed May 9, 2013.
U.S. Appl. No. 13/974,376, filed Aug. 23, 2013.
U.S. Appl. No. 13/974,389, filed Aug. 23, 2013.
U.S. Appl. No. 13/974,401, filed Aug. 23, 2013.
U.S. Appl. No. 13/974,413, filed Aug. 23, 2013.
U.S. Appl. No. 14/032,588, filed Sep. 20, 2013.
U.S. Appl. No. 14/195,362, filed Mar. 3, 2014.
U.S. Appl. No. 14/284,019, filed May 21, 2014.
U.S. Appl. No. 14/492,874, filed Sep. 22, 2014.
U.S. Appl. No. 14/572,173, filed Dec. 16, 2014.
U.S. Appl. No. 14/599,803, filed Jan. 19, 2015.
U.S. Appl. No. 14/844,810, filed Sep. 3, 2015.
U.S. Appl. No. 14/945,181, filed Nov. 18, 2015.
U.S. Appl. No. 14/980,836, filed Dec. 28, 2015.
U.S. Appl. No. 15/058,056, filed Mar. 1, 2016.
U.S. Appl. No. 15/144,191, filed May 2, 2016.
U.S. Appl. No. 15/398,398, filed Jan. 4, 2017.
U.S. Appl. No. 15/342,448, filed Nov. 3, 2016.
U.S. Appl. No. 15/438,406, filed Feb. 21, 2017.
U.S. Appl. No. 15/438,458, filed Feb. 21, 2017.
U.S. Appl. No. 15/634,776, filed Jun. 27, 2017.
U.S. Appl. No. 15/672,228, filed Aug. 8, 2017.
U.S. Appl. No. 15/818,997, filed Nov. 21, 2017.
U.S. Appl. No. 15/865,755, filed Jan. 9, 2018.
U.S. Appl. No. 15/936,241, filed Mar. 26, 2018.
U.S. Appl. No. 15/971,226, filed May 4, 2018.
U.S. Appl. No. 16/163,029, filed Oct. 17, 2018.
U.S. Appl. No. 16/251,664, filed Jan. 18, 2019.
PCT/US02/32542, Oct. 11, 2002.
PCT/US02/32575, Oct. 11, 2002.
PCT/US02/32594, Oct. 11, 2002.
PCT/US04/17076, May 28, 2004.
PCT/US07/79357, Sep. 25, 2007.
PCT/US11/36244, May 12, 2011.
"Cellulose" Kirk-Othmer Concise Encyclopeida of Chemical Technology; Abridged version of the 24 Volume, NY, Wiley; 227-228 (1978-1984).
"Excipients, Croscarmellose Sodium", Pformulate Excipients, http://www.pformulate.com/croscarmellose.htm (Sep. 29, 2002).
ATRIDOX(R) (Doxycycline Hyclate) Product Label.
Barton, S. et al "Citric Buffer Calculation", Version 1.1, Nov. 19, 2000.
Birkhauser, "Cell Encapsulation Technology and Therapeutics" (Jan. 5, 2009).
Bodmeier, Roland, "Evaluation of Drug-Containing Polymer Films Prepared from Aqueous Latexes", Pharmaceutical Research, vol. 6, No. 8 (1989).
Cholewinski et al., Pharmaceutica Acta Helvetiae, 71:405-419, 1996.
Croscarmellose sodium http://ww.nbent.com/crosscarmellose.htm (Mar. 29, 2005).
Delsym Product Label (Feb. 13, 2007).
Di Donato et al., J. Biol. Chem, 268(7): 4745-4751, 1993.
Eiamtrakarn et al., "Gastrointestinal Mucoadhesive Path System (GI-MAPS) for oral administration of G-CSF, a model protein", Bipmaterials 23: 145-152 (2002).
Endo and Ueda, FABAD J. PHARM. SCI., 29:27-38, 2004.
Engel, June V PhD, "The Benefits of Eating Fibre" http://www.diabetes.ca/common/PrintVersion.asp?ID=45493 May 11, 2005.
Flick, E., Water-Soluble Resins—An Industrial Guide, 1991 (2nd Ed.) William Andrew Publishing/Noyes, pp. 389-392.
Goldberg et al., "Biotechnology and Food Ingredients", Springer: 352 (1991).
Hadvary et al., "Inhibition of pancreatic lipase in vitro by the covalent inhibitor tetrahydrolistatin", Biochem J.; 256: 357-361 (1988).
Ko et al., "Behavior of etrahydrolipstatin in biological model membranes and emulsions", J. of Lipid Research; 38:1544-1552 (1997).
Kuhtreiber. In Cell Encapsulation and Therapeutics . Copyright 1999.
Lazaridou et al.; Thermophysical properties of chitosan, chitosanstarch and chitosan-pullulan films near the glass transition; Elsevier Science Ltd.; 2002; pp. 179-190.
Leathers, Appl. Microbiol. Biotechnol., 62: 468-473, 2003.
Le Person, S. Le et al., "Near infrared drying of pharmaceutical thin films: experimental analysis of internal mass transport," Chemical Engineering and Processing; (1998) pp. 257-263, 37.
Mahmood et al., "A limited sampling method for the estimation of AUC and Cmax of cabamazepine and carbamazepine epoxide foliowing a single and multiple dose of a sustained-release product", BR J Clin Pharmacol; 45:241-246 (1998).
Mix. http://www.askoxford.com/concise_oed/mixx?view=uk. Accessed Dec. 23, 2004.
Nicorete Packaging (Aug. 29, 2006).
Oriski, S.C., "Johnson debuts cutter for new Saran film" Packaging World Oct. 1, 2004, http://www.packworld.com/view-18051.
Peh Kok Khiang et al., "Polymeric Films as Vehicle for Buccal Delivery: Swelling, Mechanical, and Bioadhesive Properties," J Pharm Pharmaceut Sci (1999) pp. 53-61, 2:2.
Polyethylenglykoke, Fachgebit Chemie, Unterthema Makromolekulare Chemie, XP-002298105 (Sep. 20, 2004).
Repka et al., "Bioadhesive properties of hydroxypropylcellulose topical films produced by hot-melt extrusion," Journal of Controlled Release, 70: 341-351 (2001).
Repka et al., "Influence of Vitamin E TPGS on the properties of hydrophilic films produced by hot-melt extrusion," Int. J. Pharmaceutics, 202: 63-70 (2000).
Senel, S., et al., "Chitosan films and hydrogels of chlorhexidine gluconate for oral mucosal delivery", Int. J. Pharmaceutics, 193: pp. 197-203 (2000).
Stella, V., et al., "Gliadin Films. I: Preparation and in vitro evaluation as a carrier for controlled drug release", Int., J. Pharmaceutics, 121: pp. 117-121 (1995).
Sudafed & Sudafed PE, http://www.sudafed.com/products/pe_quickstrips.html (Aug. 17, 2007).
Well—Definition of from The American Heritage College Dictionary, 3rd Ed., p. 1531 (1993).
Bauer, K.H. et al., "Pharmazeutische Technologie", pp. 208-209 (1997).
Pinnamanemi, S. et al., "Formulation approaches for orally administered poorly soluble drugs", Pharmazie 57(5): 291-300(2002).
Chaumeil, J.C., "Micronization: A Method of Improving the Bioavailability of Poorly Soluble Drugs", Methods and Findings in Experimental and Clinical Pharmacology 20(3): 211-215 (1998).
Voigt, R. et al., "Pharmaseutische Technology fur Studium und Berf", pp. 179-180 (1995).
Nanda, A. et al., "An update on taste masking technologies for oral pharmaceuticals", Indian J Pharma Sci 64(1): 10-17 (2002).
Bornschein, M. et al., "Micro- und Nanopartikeln als Arzneliestofftragersysteme unter besonderer Berucksichtigung der Herstellungsmethoden", Die Pharmazie 44(9): 585-593 (1989).
Cohen E. et al., "Modern Coating and Drying Technology", pp. 268-277 (1992).
"Adsorption at Solid Surfaces," Encyclopedia of Pharmaceutical Technology (Swarbrick (ed.)), pp. 73 (1988).
Photograph of Tetracycline HCL (https://de.wikipedia.org/wiki/Tetracycline#/media/File:Tetracycline-HCL_substance_photo.jpg).
Textbook of Polymer Science (2nd Ed.) pp. 1-22 (Wiley 1971).
Thimmashetty, J. et al, "Preparation and Evaluation of Buccal Dosage Forms of Insulin."

(56) References Cited

OTHER PUBLICATIONS

Thimmashetty, J. et al, "Design and In Vivo Evaluation of Carvedilol Buccal Mucoadhesive Patches," Pak. J. Pharm. Sci. 21(3):241-248 (2008).
Elemente des Apparatebause, (Titz, H. (ed.)), pp. 546-669 (Springer-Verlag 1992). (includes partial English translation.).
The United States Pharmacopeia (20th Rev.), pp. 3-4, 12, 16, 955-957, 1023, 1030-1031, 1412, 1451 (USP 1980).
Varanda, F. et al., "Solubility of Antibiotics in Different Solvents. 1. Hydrochloride Forms of Tetracycline, Moxifloxacin, and Ciprofloxacin," Ind. Eng. Chem. Res. 45:6368-6374 (2006).
Phramazeutische Technologie fur Studium und Beruf (Voigt, R. (ed.)), p. 65 (Ullstein Mosby 1995).
Polymer Molecular Weights (Slade, P.E. (ed.), p. 1-8 (Marcel Dekker, Inc. 1975).
Metallic Pigments in Polymers, p. 132 (Rapra Technology Limited 1999).
White, J.G., "In Situ Determination of Delavirdine Mesylate Particle Size in Solid Oral Dosage Forms," Pharmaecutical Research 16(4):545-548 (1999).
Yamamura, K. et al., "Oral Mucosal Adhesive Film Containing Local Anesthetics: In Vitro and Clinical Evaluation," J. Biomed. Mater Res. (Appl. Biomater.) 43:313-317 (1998).
Pharmazeutische Technologie: Insustrielle Herstellung und Entwicklung von Arzneimitteln (Zimmermann, I. (ed.)), p. 246 (Springer-Verlag 1998).
Modern coating technology systems for paper, film and foil (Shepherd, F. (ed.)), p. 5 (Emap Maclaren Ltd. 1995).
Blank, Z. et al., "Structural studies of organic gels by SEM", J. Material Science 9:1815-1822 (1974).
CAS Presents, "Common Chemistry", http://www.commonchemistry.org.ChemicalDetail.aspx?ref=25322-68-3&terms=polyeth . . . Oct. 28, 2009.
Huus et al., "Thermal Dissociation and Unfolding of Insulin", Biochemistry, 44: 11171-11177 (2005).
Steiner et al., "Organic Derivatives of Alginic Acid", Industrial and Engineering Chemistry; 43(9): 2073-2077 (1951).
Al-Ghananeem et al., "Effect of pH on Sublingual Absorption of Oxycodone Hydrochloride", AAPS PharmSciTech; Article 23, 7(1) (2006) (http://www.aapspharmscitec.org).
Bhumkar et al., "Chitosan Reduced Gold Nanoparticles as Novel Carriers for Transmucosal Delivery of Insulin", Pharmaceutical Research; 24(8): 1415-1426 (2007).
Bowen P., "Particle Size Distribution Measurement from Millimeters to Nanometers and from Rods to Platelets", Journal of Dispersion Science and Technology; 23(5): 631-662 (2002).
Trademark Reg. No. 2,944,841—registered Apr. 26, 2005 to Reynolds Metal Co for "EZ SLIDE".
Hariharan et al., "Thin Film Technology, Orally Dissolving Film Strips (ODFS): The Final Evolution of Orally Dissolving Dosage Forms," Drug Delivery Technology; 9(2): 24-29 (2009).
Joshi et al., "Gold Nanoparticles as Carrier for Efficient Transmucosal Insulin Delivery", Langmuir; 22: 300-305 (2006).
Ojeda et al., "Preparation of multifunctional glyconanoparticles as a platform for potential carbohydrate-based anticancer vaccines", Carbohydrate Research; 342: 448-459 (2007).
U.S. Department of Health and Human Services Food and Drug Administration Center for Drug Evaluation and Research (CDER) "Guidance for Industry—Incorporation of Physical-Chemical Identifiers into Solid Oral Dosage Form Drug Products for Anticounterfeiting" Silver Spring, MD; 1-8 (Jul. 9, 2009).
Boo, Woong Jae, "Characterization of Thin Film Properties of Melamine Based Dendrimer Nanoparticles", Thesis for Texas A&M University, Dec. 2003.
"Suboxone Subligualtabletten" in: Verlag Rote Liste Service GmbH: "Rote Liste 2008" 2008, Verlag Rote Liste Service GmbH, Frankfurt/Main, XP00264986, p. 39018, the whole document.
Pharmazeutische Technologie (4th Ed.), (Bauer, K.H. et al. (eds.)), pp. 94-94, 286-287 (Georg Thieme Verlag Stuttgart1993).

Brittian, H.G., "What Is the 'Correct' Method to Use for Particle-Size Determination?," Pharmaceutical Technology 96-98 (Jul. 2001).
"More Solutions to Sticky Problems: A Guide to Getting More From Your Brookfield Viscometer," Brookfield Engineering Laboratories, Inc. (1985).
DeGrande, G., et al., "Specialized Oral Mucosal Drug Delivery Systems: Patches," Drugs and the Pharmaceutical Sciences (Swarbrick, J. (ed.)), Ch. 12, pp. 285-317 (1995).
Polymer Science and Technology (Obewele, R.O. (ed.)), pp. 1-23 (2000).
Etzler, F.M. and Sanderson, "Partilce Size Analysis: a Comparative Study of Various Methods," Part. Part. Syst. Charact. 12: 127-224 (1995).
Roddy, R.E., "A Controlled Trial of Nonoxynol 9 Film to Reduce Male-to-Female Transmission of Sexually Transmitted Diseases," New England J. Med. 339(8):504-510 (1998).
Remington's Pharmaceutical Sciences (18th Ed.) (Gennaro, A.R. (ed.)), Ch. 19, pp. 296-298 (1990).
Etzler, F.M., "Particle Size Analysis: a Comparison of Methods," Polymeric Materials: Science & Engineering 87:335-336 (2002).
Patel, V.F. et al., "Advances in oral transmucosal drug delivery," J. Controlled Release 153:106-116 (2011).
"Adsorption," Kirk-Othmer Encyclopedia of Chemical Technology (4th Ed.) pp. 493-494 (Wiley 1991).
"Matrix," Webster's Third New International Dictionary of the English Language Unabridged (Gove, P.B. (ed.)) (G. & C. Merriam Company 1968).
Plastic Films (Osborn, K.R. and Jankins, W.A. (eds.), p. 89 (1992).
Martinez, M.N. and Amidon, G.L., "A Mechanistic Approach to Understanding the Factors Affecting Drug Absorption: A Review of Fundamentals," J. Clin. Pharmacol. 42:620-643 (2002).
Amidon, G.L. et al., "A Theoretical Basis for a Biopharmaceutical Drug Classification: The Correlation of In Vitro Drug Product Dissolution and in Vivo Bioavailability," Pharm. Res. 12(3):413-420 (1995).
Anders, R. and Merkle, H.P., "Evaluation of laminated mucoadhesive patches for buccal drug delivery," Int. J. Pharmaceutics 49: 231-240 (1989).
Pharmaceutical Dosage Forms and Drug Delivery Systems (7th Ed.) (Ansel, H.C. et al. (eds.)), p. 66 (1999).
Apicella, A. et al., "poly(ethylene oxide) (PEO) and different molecular weight PEO blends monolithic devices for drug release," Biomaterials 14(2):83-90 (1993).
Pharmazeutische Technologie (5th Ed.) (Bauer, K.H. et al. (eds.)), pp. 208-209 (Stuttgart Jena Lubeck Ulm 1997).
Bowser, T.J. and Wilhelm, L.R., "Modeling Simultaneous Shrinkage and Heat and Mass Transfer of a Thin. Nonporous Film During Drying," J. Food Sci. 60(4):753-757 (1995).
Theory of pharmaceutical systems: vol. II (Carstensen, J.T. (ed.)), pp. 4-9 (1973).
Cassidy, J. P. et al., "Controlled buccal delivery of buprenorphine," J. Controlled Release 25:21-29 (1993).
EUDRAGIT E 100, EUDRAGIT E PO, and EUDRAGIT E 12,5, Technical Information, Evonik Inductries AG, (2012).
EUDRAGIT L 100 and EUDRAGIT S 100, Technical Information, Evonik Inductries AG, (2012).
Europaisches Arzneibuch (3rd Ed.), pp. 142-143 (Deutscher Apotheker Verlag 1997).
European Pharmacopeia (3rd Ed.), p. 134 (1997).
Frankman, O. et al., "clinical Evaluation of C-Film, a Vaginal Contraceptive," J. Int. Med. Res. 3:292-296 (1975).
Friend, D.R., "Polyacrylate resin microcapsules for taste masking of antibiotics," J. Microencapsulation 9(4):469-480 (1992).
Fuller, C.S. et al., "Interactions in poly(ethylene oxide)-hydroxylpropyl methylcellulose blends," Polymer 42:9583-9592 (2001).
Save, T. et al., "Comparative Study of Buccoadhesive Formulations and Sublingual Capsules of Nifedipine," J. Pharm. Pharmacol. 46:192-195 (1994).
Save, T. and Vankitachalam, P., "Studies on Solid Dispersions of Nifedipine," Drug Development and Industrial Pharmacy 18(15):1663-1679 (1992).

(56) References Cited

OTHER PUBLICATIONS

Roy, G.M., "Taste Macking in Oral Pharmaceuticals," Pharmaceutical Technology, pp. 84-99 (Apr. 1994).
Guo, J.H. and Cookock, K.M., "Bioadhesive Polymer Buccal Patches for Buprenorphine Controlled Delivery: Solubility Consideration," Drug Development and Industrial Pharmacy 21(7): 2013-2019 (1995).
Mixing in the Process Industries (2nd Ed.) Hamby, N. et al. (eds.)), pp. 3, 115 (Butterworth Heinemann 1997).
Himics, R, and Pineiro, R., "The Importance of Particle Size in Liquid Coatings," Products Finishing 63(2):00329940 (1998).
Handbook of Pharmaceutical Excipients (Rowe, R. et al. (eds.)), pp. 326, 513, 522 (2009).
Ilango, R. et al., "In-Vitro Studies on Buccal strips of Glibenclamide using Chitosan," Indian J. Pharm. Sci. 59(5):232-235 (1997).
Ishikawa, T. et al., "Preparation and Evaluation of Tablets Rapidly Disintegrating in Saliva Containing Bitter-Taste-Masked Granules by the Compression Method," Chem. Pharm. Bull. 47(10):1451-1454 (1999).
Kaya, S. and Kaya, A., "Microwave drying effects on properties of whey protein isolate edible films," J. Food Engineenng, 43: 91-96 (2000).

\* cited by examiner

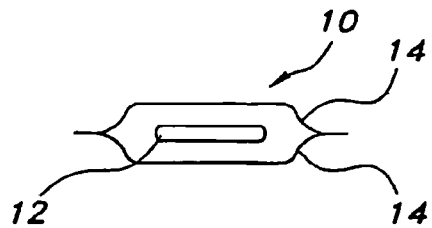
FIG. 1
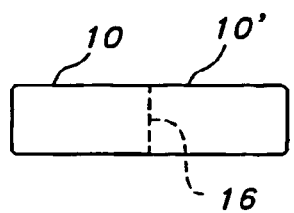
FIG. 2
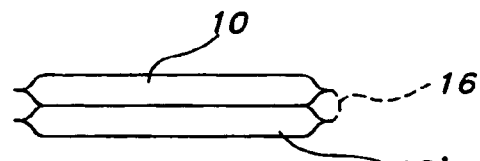
FIG. 3
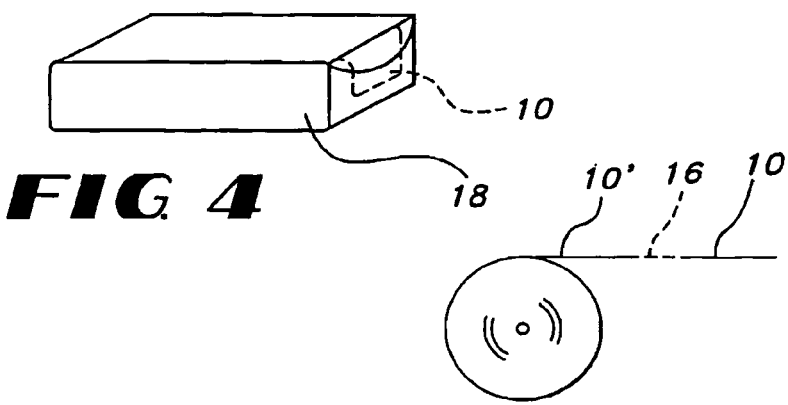
FIG. 4
FIG. 5

UNIFORM FILMS FOR RAPID-DISSOLVE DOSAGE FORM INCORPORATING ANTI-TACKING COMPOSITIONS

CROSS-REFERENCE TO RELATED APPLICATIONS

The present application is a continuation of U.S. application Ser. No. 16/505,244, filed Jul. 8, 2019, which is a continuation of U.S. application Ser. No. 15/818,997, filed Nov. 21, 2017, which is a continuation of U.S. application Ser. No. 15/438,406, filed Feb. 21, 2017, issued as U.S. Pat. No. 9,855,221, which is a continuation of U.S. application Ser. No. 15/398,398, filed Jan. 4, 2017, which is a continuation of U.S. application Ser. No. 15/144,191, filed May 2, 2016, which is a continuation of U.S. application Ser. No. 14/844,810, filed Sep. 3, 2015, which is a continuation of U.S. application Ser. No. 14/284,019, filed May 21, 2014, which is a continuation of U.S. application Ser. No. 11/517,982, filed Sep. 8, 2006, issued as U.S. Pat. No. 8,765,167, which claims the benefit of U.S. Provisional Application No. 60/715,528, filed Sep. 9, 2005, and is a continuation-in-part of U.S. application Ser. No. 10/074,272, filed Feb. 14, 2002, issued as U.S. Pat. No. 7,425,292, which claims the benefit of U.S. Provisional Application No. 60/328,868, filed Oct. 12, 2001, the contents of all of which are incorporated herein by reference in entirety.

FIELD OF THE INVENTION

The present invention relates to rapidly dissolving films incorporating anti-tacking agents and methods of their preparation. The films also may contain an active ingredient that is evenly distributed throughout the film.

BACKGROUND OF THE RELATED TECHNOLOGY

Active ingredients, such as drugs or pharmaceuticals, may be prepared in a tablet form to allow for accurate and consistent dosing. However, this form of preparing and dispensing medications has many disadvantages including that a large proportion of adjuvants that must be added to obtain a size able to be handled, that a larger medication form requires additional storage space, and that dispensing includes counting the tablets which has a tendency for inaccuracy. In addition, many persons, estimated to be as much as 28% of the population, have difficulty swallowing tablets. While tablets may be broken into smaller pieces or even crushed as a means of overcoming swallowing difficulties, this is not a suitable solution for many tablet or pill forms. For example, crushing or destroying the tablet or pill form to facilitate ingestion, alone or in admixture with food, may also destroy the controlled release properties.

As an alternative to tablets and pills, films may be used to carry active ingredients such as drugs, pharmaceuticals, and the like. However, historically films and the process of making drug delivery systems therefrom have suffered from a number of unfavorable characteristics that have not allowed them to be used in practice.

Films that incorporate a pharmaceutically active ingredient are disclosed in expired U.S. Pat. No. 4,136,145 to Fuchs, et al. ("Fuchs"). These films may be formed into a sheet, dried and then cut into individual doses. The Fuchs disclosure alleges the fabrication of a uniform film, which includes the combination of water-soluble polymers, surfactants, flavors, sweeteners, plasticizers and drugs. These allegedly flexible films are disclosed as being useful for oral, topical or enteral use. Examples of specific uses disclosed by Fuchs include application of the films to mucosal membrane areas of the body, including the mouth, rectal, vaginal, nasal and ear areas.

Examination of films made in accordance with the process disclosed in Fuchs, however, reveals that such films suffer from the aggregation or conglomeration of particles, i.e., self-aggregation, making them inherently non-uniform. This result can be attributed to Fuchs' process parameters, which although not disclosed likely include the use of relatively long drying times, thereby facilitating intermolecular attractive forces, convection forces, air flow and the like to form such agglomeration.

The formation of agglomerates randomly distributes the film components and any active present as well. When large dosages are involved, a small change in the dimensions of the film would lead to a large difference in the amount of active per film. If such films were to include low dosages of active, it is possible that portions of the film may be substantially devoid of any active. Since sheets of film are usually cut into unit doses, certain doses may therefore be devoid of or contain an insufficient amount of active for the recommended treatment. Failure to achieve a high degree of accuracy with respect to the amount of active ingredient in the cut film can be harmful to the patient. For this reason, dosage forms formed by processes such as Fuchs, would not likely meet the stringent standards of governmental or regulatory agencies, such as the U.S. Federal Drug Administration ("FDA"), relating to the variation of active in dosage forms. Currently, as required by various world regulatory authorities, dosage forms may not vary more than 10% in the amount of active present. When applied to dosage units based on films, this virtually mandates that uniformity in the film be present.

The problems of self-aggregation leading to non-uniformity of a film were addressed in U.S. Pat. No. 4,849,246 to Schmidt ("Schmidt"). Schmidt specifically pointed out that the methods disclosed by Fuchs did not provide a uniform film and recognized that that the creation of a non-uniform film necessarily prevents accurate dosing, which as discussed above is especially important in the pharmaceutical area. Schmidt abandoned the idea that a mono-layer film, such as described by Fuchs, may provide an accurate dosage form and instead attempted to solve this problem by forming a multi-layered film. Moreover, his process is a multi-step process that adds expense and complexity and is not practical for commercial use.

Other U.S. patents directly addressed the problems of particle self-aggregation and non-uniformity inherent in conventional film forming techniques. In one attempt to overcome non-uniformity, U.S. Pat. No. 5,629,003 to Horstmann et al. and U.S. Pat. No. 5,948,430 to Zerbe et al. incorporated additional ingredients, i.e. gel formers and polyhydric alcohols respectively, to increase the viscosity of the film prior to drying in an effort to reduce aggregation of the components in the film. These methods have the disadvantage of requiring additional components, which translates to additional cost and manufacturing steps. Furthermore, both methods employ the use the conventional time-consuming drying methods such as a high-temperature air-bath using a drying oven, drying tunnel, vacuum drier, or other such drying equipment. The long length of drying time aids in promoting the aggregation of the active and other adjuvant, notwithstanding the use of viscosity modifiers. Such processes also run the risk of exposing the active, i.e., a drug, or vitamin C, or other components to prolonged exposure to moisture and elevated temperatures, which may render it ineffective or even harmful.

In addition to the concerns associated with degradation of an active during extended exposure to moisture, the conventional drying methods themselves are unable to provide uniform films. The length of heat exposure during conventional processing, often referred to as the "heat history", and the manner in which such heat is applied, have a direct effect on the formation and morphology of the resultant film product. Uniformity is particularly difficult to achieve via conventional drying methods where a relatively thicker film, which is well-suited for the incorporation of a drug active, is desired. Thicker uniform films are more difficult to achieve because the surfaces of the film and the inner portions of the film do not experience the same external conditions simultaneously during drying. Thus, observation of relatively thick films made from such conventional processing shows a non-uniform structure caused by convection and intermolecular forces and requires greater than 10% moisture to remain flexible. The amount of free moisture can often interfere over time with the drug leading to potency issues and therefore inconsistency in the final product.

Conventional drying methods generally include the use of forced hot air using a drying oven, drying tunnel, and the like. The difficulty in achieving a uniform film is directly related to the rheological properties and the process of water evaporation in the film-forming composition. When the surface of an aqueous polymer solution is contacted with a high temperature air current, such as a film-forming composition passing through a hot air oven, the surface water is immediately evaporated forming a polymer film or skin on the surface. This seals the remainder of the aqueous film-forming composition beneath the surface, forming a barrier through which the remaining water must force itself as it is evaporated in order to achieve a dried film. As the temperature outside the film continues to increase, water vapor pressure builds up under the surface of the film, stretching the surface of the film, and ultimately ripping the film surface open allowing the water vapor to escape. As soon as the water vapor has escaped, the polymer film surface reforms, and this process is repeated, until the film is completely dried. The result of the repeated destruction and reformation of the film surface is observed as a "ripple effect" which produces an uneven, and therefore non-uniform film. Frequently, depending on the polymer, a surface will seal so tightly that the remaining water is difficult to remove, leading to very long drying times, higher temperatures, and higher energy costs.

Other factors, such as mixing techniques, also play a role in the manufacture of a pharmaceutical film suitable for commercialization and regulatory approval. Air can be trapped in the composition during the mixing process or later during the film making process, which can leave voids in the film product as the moisture evaporates during the drying stage. The film frequently collapse around the voids resulting in an uneven film surface and therefore, non-uniformity of the final film product. Uniformity is still affected even if the voids in the film caused by air bubbles do not collapse. This situation also provides a non-uniform film in that the spaces, which are not uniformly distributed, are occupying area that would otherwise be occupied by the film composition. None of the above-mentioned patents either addresses or proposes a solution to the problems caused by air that has been introduced to the film.

Moreover, films go through numerous processing steps prior to primary packaging, e.g., in canisters, and secondary packaging, e.g., in pouches or blister packs. The processing steps present significant challenges for the development of quality films that possess optimal film surface properties such as low coefficient of friction or high slip. Throughout this process, it is important to maintain the integrity of the film from initial manufacture to final packaging. It is desirable, therefore, to prevent or alleviate problems that diminish the integrity of the film, such as films that soften, get tacky, adhere, dry up, or become brittle over time.

More specifically, over-the-counter film products, such as candy and breath films, typically are packaged in canisters containing 16 film units, also referred to as strips, or higher (up to 24 or even 32 film strips per canister). The number of film strips per canister varies based on product type, active dose and packaging configuration among other considerations. When packaging multiple film strips in a canister, however, problems such as strips sticking to one another often arise.

Adherence between film strips is a common problem encountered in edible film products and may arise due to a variety of reasons. For instance, in some cases, adherence between film strips may be caused by the components used in film manufacture. Components such as flavors, plasticizers, and actives in the film can sometimes soften the film and have a detrimental effect on film quality. For example, in films having high acidulent content, the acids may exert an excessive plasticizing effect on the film. Such effect may be intensified by the hygroscopicity of some acids or other components in the film.

In some cases, adherence between film strips may be caused by changes in film properties due to temperature and/or humidity changes. Some films may become tacky over time when exposed to non-optimal temperature and/or humidity conditions. This problem may be amplified for products that have a very narrow optimal temperature and/or humidity range for storage.

Overall, films that exhibit tackiness or become tacky over time may present numerous problems. First, conversion of master rolls to daughter rolls, and further conversion to film strips becomes substantially more difficult when film is tacky. In addition, tacky film strips tend to adhere to one another when stacked in packaging, e.g., a canister. Accordingly, it becomes difficult for a user to remove a single film strip at a time from the film packaging. Overall, such adherence within the packaging decreases the aesthetics of the film strips as well as an individual consumer's ease of use.

Therefore, there is a need for compositions that enable films to slide against one another, thereby providing ease of conversion, maximum storage stability and ease of consumer use, among other benefits. Further, there is a need for methods of preparing such films, which maintain the uniform distribution of components therein, thereby preventing undesired aggregations and promoting uniformity in the final film product.

SUMMARY OF THE INVENTION

In one aspect of the present invention, there is provided an edible film for delivery of an active including: an edible, water-soluble polymer, at least one anti-tacking agent selected from the group consisting of lubricants, antiadherants, glidants and combinations thereof; and an active component selected from the group consisting of cosmetic agents, pharmaceutical agents, vitamins, bioactive agents and combinations thereof, wherein the film is self-supporting.

In another aspect of the present invention, there is provided an edible film for delivery of an active including: an edible, water-soluble polymer component which includes at least one polymer selected from hydroxypropyl cellulose, hydroxypropylmethyl cellulose, polyethylene oxide and combinations thereof; an active component selected from cosmetic agents, pharmaceutical agents, vitamins, bioactive agents and combinations thereof; and an anti-tacking agent containing Vitamin E TPGS present in amounts of about 0.01% to about 20% by weight of the film.

In another aspect of the present invention, there is provided an edible film for delivery of an active including: an edible, water-soluble polymer component which includes polyethylene oxide in combination with a polymer selected from hydroxypropyl cellulose, hydroxypropylmethyl cellulose and combinations thereof; and Vitamin E TPGS present in amounts sufficient to provide anti-tacking and therapeutic properties, wherein the film is self-supporting.

In some embodiments, there is provided an edible film for delivery of an active which includes: an edible, water-soluble polymer including polyethylene oxide and hydroxypropyl cellulose; polydextrose, wherein the polyethylene oxide, hydroxypropyl cellulose and polydextrose are present in a ratio of about 45:45:10; an active component selected from cosmetic agents, pharmaceutical agents, vitamins, bioactive agents and combinations thereof; and at least one anti-tacking agent.

In another aspect, there is provided an edible film for delivery of an active including: (a) a self-supporting film having at least one surface, the film including: (i) an edible, water-soluble polymer; and (ii) an active component selected from cosmetic agents, pharmaceutical agents, vitamins, bioactive agents and combinations thereof; and (b) a coating on the at least one surface of the self-supporting film, the coating including at least one anti-tacking agent.

Some embodiments provide a multi-layer film for delivery of an active including: (a) at least one first film layer containing: (i) an edible, water-soluble polymer; and (ii) an anti-tacking agent; and (b) a second film layer including: (i) an edible, water-soluble polymer; and (ii) an active component selected from cosmetic agents, pharmaceutical agents, vitamins, bioactive agents and combinations thereof. The first film layer is substantially in contact with the second film layer.

The present invention also provides a process for making a self-supporting film having a substantially uniform distribution of components including the steps of: combining an edible, water-soluble polymer, a solvent, an active component selected from cosmetic agents, pharmaceutical agents, vitamins, bioactive agents and combinations thereof and at least one anti-tacking agent to form a matrix with a uniform distribution of the components; forming a self-supporting film from the matrix; providing a surface having top and bottom sides; feeding the film onto the top side of the surface; and drying the film by applying heat to the bottom side of the surface.

BRIEF DESCRIPTION OF THE DRAWINGS

FIG. 1 shows a side view of a package containing a unit dosage film of the present invention.

FIG. 2 shows a top view of two adjacently coupled packages containing individual unit dosage forms of the present invention, separated by a tearable perforation.

FIG. 3 shows a side view of the adjacently coupled packages of FIG. 2 arranged in a stacked configuration.

FIG. 4 shows a perspective view of a dispenser for dispensing the packaged unit dosage forms, dispenser containing the packaged unit dosage forms in a stacked configuration.

FIG. 5 is a schematic view of a roll of coupled unit dose packages of the present invention.

DETAILED DESCRIPTION OF THE INVENTION

Figure 6:
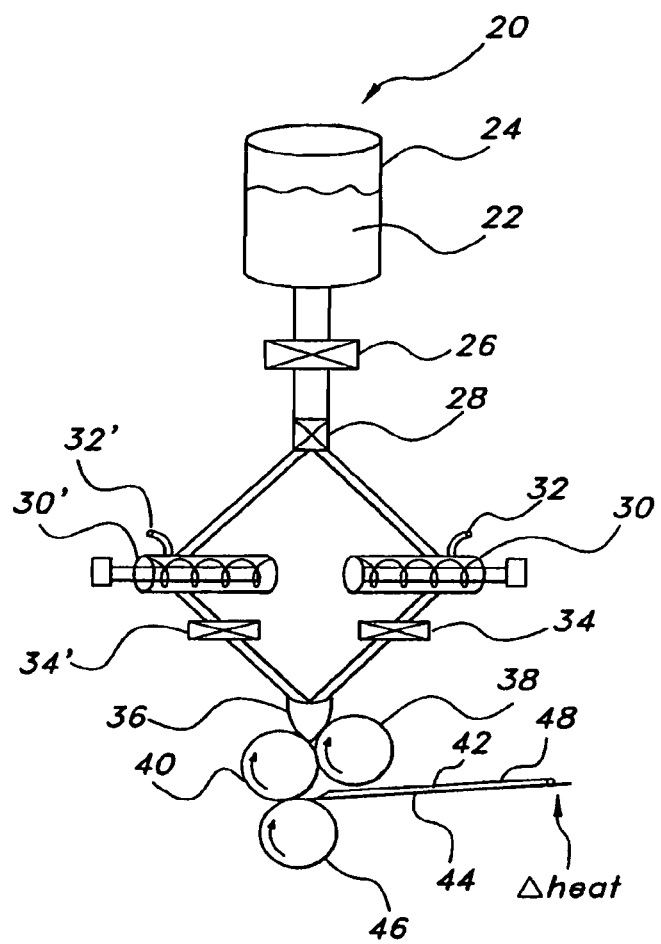
FIG. 6 is a schematic view of an apparatus suitable for preparation of a pre-mix, addition of an active, and subsequent formation of the film.

For the purposes of the present invention the term non-self-aggregating uniform heterogeneity refers to the ability of the films of the present invention, which are formed from one or more components in addition to a polar solvent, to provide a substantially reduced occurrence of, i.e. little or no, aggregation or conglomeration of components within the film as is normally experienced when films are formed by conventional drying methods such as a high-temperature air-bath using a drying oven, drying tunnel, vacuum drier, or other such drying equipment. The term heterogeneity, as used in the present invention, includes films that will incorporate a single component, such as a polymer, as well as combinations of components, such as a polymer and an active. Uniform heterogeneity includes the substantial absence of aggregates or conglomerates as is common in conventional mixing and heat drying methods used to form films.

Furthermore, the films of the present invention have a substantially uniform thickness, which is also not provided by the use of conventional drying methods used for drying water-based polymer systems. The absence of a uniform thickness detrimentally affects uniformity of component distribution throughout the area of a given film.

The film products of the present invention are produced by a combination of a properly selected polymer and a polar solvent, optionally including an active ingredient as well as other fillers known in the art. These films provide a non-self-aggregating uniform heterogeneity of the components within them by utilizing a selected casting or deposition method and a controlled drying process. Examples of controlled drying processes include, but are not limited to, the use of the apparatus disclosed in U.S. Pat. No. 4,631,837 to Magoon ("Magoon"), herein incorporated by reference, as well as hot air impingement across the bottom substrate and bottom heating plates. Another drying technique for obtaining the films of the present invention is controlled radiation drying, in the absence of uncontrolled air currents, such as infrared and radio frequency radiation (i.e. microwaves).

The objective of the drying process is to provide a method of drying the films that avoids complications, such as the noted "rippling" effect, that are associated with conventional drying methods and which initially dry the upper surface of the film, trapping moisture inside. In conventional oven drying methods, as the moisture trapped inside subsequently evaporates, the top surface is altered by being ripped open and then reformed. These complications are avoided by the present invention, and a uniform film is provided by drying the bottom surface of the film first or otherwise preventing the formation of polymer film formation (skin) on the top surface of the film prior to drying the depth of the film. This may be achieved by applying heat to the bottom surface of the film with substantially no top air flow, or alternatively by the introduction of controlled microwaves to evaporate the water or other polar solvent within the film, again with substantially no top air flow. Yet alternatively, drying may be achieved by using balanced fluid flow, such as balanced air flow, where the bottom and top air flows are controlled to provide a uniform film. In such a case, the air flow directed at the top of the film should not create a condition which would cause movement of particles present in the wet film, due to forces generated by the air currents. Additionally, air currents directed at the bottom of the film should desirably be controlled such that the film does not lift up due to forces from the air. Uncontrolled air currents, either above or below the film, can create non-uniformity in the final film products. The humidity level of the area surrounding the top surface may also be appropriately adjusted to prevent premature closure or skinning of the polymer surface.

This manner of drying the films provides several advantages. Among these are the faster drying times and a more uniform surface of the film, as well as uniform distribution of components for any given area in the film. In addition, the faster drying time allows viscosity to quickly build within the film, further encouraging a uniform distribution of components and decrease in aggregation of components in the final film product. Desirably, the drying of the film will occur within about ten minutes or fewer, or more desirably within about five minutes or fewer.

The present invention yields exceptionally uniform film products when attention is paid to reducing the aggregation of the compositional components. By avoiding the introduction of and eliminating excessive air in the mixing process, selecting polymers and solvents to provide a controllable viscosity and by drying the film in a rapid manner from the bottom up, such films result.

The products and processes of the present invention rely on the interaction among various steps of the production of the films in order to provide films that substantially reduce the self-aggregation of the components within the films. Specifically, these steps include the particular method used to form the film, making the composition mixture to prevent air bubble inclusions, controlling the viscosity of the film forming composition and the method of drying the film. More particularly, a greater viscosity of components in the mixture is particularly useful when the active is not soluble in the selected polar solvent in order to prevent the active from settling out. However, the viscosity must not be too great as to hinder or prevent the chosen method of casting, which desirably includes reverse roll coating due to its ability to provide a film of substantially consistent thickness.

In addition to the viscosity of the film or film-forming components or matrix, there are other considerations taken into account by the present invention for achieving desirable film uniformity. For example, stable suspensions are achieved which prevent solid (such as drug particles) sedimentation in non-colloidal applications. One approach provided by the present invention is to balance the density of the particulate ($\rho_p$) and the liquid phase ($\rho_1$) and increase the viscosity of the liquid phase ($\mu$). For an isolated particle, Stokes law relates the terminal settling velocity (Vo) of a rigid spherical body of radius (r) in a viscous fluid, as follows:

$$V_o = (2gr^2)(\rho_p - \rho_1)/9\mu.$$

At high particle concentrations, however, the local particle concentration will affect the local viscosity and density. The viscosity of the suspension is a strong function of solids volume fraction, and particle-particle and particle-liquid interactions will further hinder settling velocity.

Stokian analyses has shown that the incorporation of a third phase, dispersed air or nitrogen, for example, promotes suspension stability. Further, increasing the number of particles leads to a hindered settling effect based on the solids volume fraction. In dilute particle suspensions, the rate of sedimentation, v, can be expressed as:

$$v/V = 1/(1 + \kappa \varphi)$$

where $\kappa$ = a constant, and $\varphi$ is the volume fraction of the dispersed phase. More particles suspended in the liquid phase results in decreased velocity. Particle geometry is also an important factor since the particle dimensions will affect particle-particle flow interactions.

Similarly, the viscosity of the suspension is dependent on the volume fraction of dispersed solids. For dilute suspensions of non-interaction spherical particles, an expression for the suspension viscosity can be expressed as:

$$\mu/\mu_o = 1 + 2.5\phi$$

where $\mu_o$ is the viscosity of the continuous phase and $\phi$ is the solids volume fraction. At higher volume fractions, the viscosity of the dispersion can be expressed as $$\mu/\mu_o = 1 + 2.5 (+ C_1 \phi^2 + C_2 \phi^3 + \ldots$$

where C is a constant.

The viscosity of the liquid phase is critical and is desirably modified by customizing the liquid composition to a viscoelastic non-Newtonian fluid with low yield stress values. This is the equivalent of producing a high viscosity continuous phase at rest. Formation of a viscoelastic or a highly structured fluid phase provides additional resistive forces to particle sedimentation. Further, flocculation or aggregation can be controlled minimizing particle-particle interactions. The net effect would be the preservation of a homogeneous dispersed phase.

The addition of hydrocolloids to the aqueous phase of the suspension increases viscosity, may produce viscoelasticity and can impart stability depending on the type of hydrocolloid, its concentration and the particle composition, geometry, size, and volume fraction. The particle size distribution of the dispersed phase needs to be controlled by selecting the smallest realistic particle size in the high viscosity medium, i.e., <500 μm. The presence of a slight yield stress or elastic body at low shear rates may also induce permanent stability regardless of the apparent viscosity. The critical particle diameter can be calculated from the yield stress values. In the case of isolated spherical particles, the maximum shear stress developed in settling through a medium of given viscosity can be given as $$\tau_{max} = 3V\mu/2r.$$

For pseudoplastic fluids, the viscosity in this shear stress regime may well be the zero shear rate viscosity at the Newtonian plateau.

A stable suspension is an important characteristic for the manufacture of a pre-mix composition which is to be fed into the film casting machinery film, as well as the maintenance of this stability in the wet film stage until sufficient drying has occurred to lock-in the particles and matrix into a sufficiently solid form such that uniformity is maintained. For viscoelastic fluid systems, a rheology that yields stable suspensions for extended time period, such as 24 hours, must be balanced with the requirements of high-speed film casting operations. A desirable property for the films is shear thinning or pseudoplasticity, whereby the viscosity decreases with increasing shear rate. Time dependent shear effects such as thixotropy are also advantageous. Structural recovery and shear thinning behavior are important properties, as is the ability for the film to self-level as it is formed.

The rheology requirements for the inventive compositions and films are quite severe. This is due to the need to produce a stable suspension of particles, for example 30-60 wt %, in a viscoelastic fluid matrix with acceptable viscosity values throughout a broad shear rate range. During mixing, pumping, and film casting, shear rates in the range of 10-1 sec.$^{-1}$ may be experienced and pseudoplasticity is the preferred embodiment.

In film casting or coating, rheology is also a defining factor with respect to the ability to form films with the desired uniformity. Shear viscosity, extensional viscosity, viscoelasticity, structural recovery will influence the quality of the film. As an illustrative example, the leveling of shear-thinning pseudoplastic fluids has been derived as $$\alpha^{(n-1/n)} = \alpha_o^{(n-1/n)} - ((n-1)/(2n-1))(\tau/K)^{1/n} (2\pi/\lambda)^{(3+n)/n} h^{(2+n)/n} t$$

where a is the surface wave amplitude, $\alpha_o$ is the initial amplitude, $\lambda$ is the wavelength of the surface roughness, and both "n" and "K" are viscosity power law indices. In this example, leveling behavior is related to viscosity, increasing as n decreases, and decreasing with increasing K.

Desirably, the films or film-forming compositions of the present invention have a very rapid structural recovery, i.e. as the film is formed during processing, it doesn't fall apart or become discontinuous in its structure and compositional uniformity. Such very rapid structural recovery retards particle settling and sedimentation. Moreover, the films or film-forming compositions of the present invention are desirably shear-thinning pseudoplastic fluids. Such fluids with consideration of properties, such as viscosity and elasticity, promote thin film formation and uniformity.

Thus, uniformity in the mixture of components depends upon numerous variables. As described herein, viscosity of the components, the mixing techniques and the rheological properties of the resultant mixed composition and wet casted film are important aspects of the present invention. Additionally, control of particle size and particle shape are further considerations. Desirably, the size of the particulate a particle size of 150 microns or less, for example 100 microns or less. Moreover, such particles may be spherical, substantially spherical, or non-spherical, such as irregularly shaped particles or ellipsoidally shaped particles. Ellipsoidally shaped particles or ellipsoids are desirable because of their ability to maintain uniformity in the film forming matrix as they tend to settle to a lesser degree as compared to spherical particles.

A number of techniques may be employed in the mixing stage to prevent bubble inclusions in the final film. To provide a composition mixture with substantially no air bubble formation in the final product, anti-foaming or surface-tension reducing agents are employed. Additionally, the speed of the mixture is desirably controlled to prevent cavitation of the mixture in a manner which pulls air into the mix. Finally, air bubble reduction can further be achieved by allowing the mix to stand for a sufficient time for bubbles to escape prior to drying the film. Desirably, the inventive process first forms a masterbatch of film-forming components without active ingredients such as drug particles or volatile materials such as flavor oils. The actives are added to smaller mixes of the masterbatch just prior to casting. Thus, the masterbatch pre-mix can be allowed to stand for a longer time without concern for instability in drug or other ingredients.

When the matrix is formed including the film-forming polymer and polar solvent in addition to any additives and the active ingredient, this may be done in a number of steps. For example, the ingredients may all be added together or a pre-mix may be prepared. The advantage of a pre-mix is that all ingredients except for the active may be combined in advance, with the active added just prior to formation of the film. This is especially important for actives that may degrade with prolonged exposure to water, air or another polar solvent.

FIG. 6 shows an apparatus 20 suitable for the preparation of a pre-mix, addition of an active and subsequent formation of a film. The pre-mix or master batch 22, which includes the film-forming polymer, polar solvent, and any other additives except a drug active is added to the master batch feed tank 24. The components for pre-mix or master batch 22 are desirably formed in a mixer (not shown) prior to their addition into the master batch feed tank 24. Then a pre-determined amount of the master batch is controllably fed via a first metering pump 26 and control valve 28 to either or both of the first and second mixers, 30, 30'. The present invention, however, is not limited to the use of two mixers, 30, 30', and any number of mixers may suitably be used. Moreover, the present invention is not limited to any particular sequencing of the mixers 30, 30', such as parallel sequencing as depicted in FIG. 6, and other sequencing or arrangements of mixers, such as series or combination of parallel and series, may suitably be used. The required amount of the drug or other ingredient, such as a flavor, is added to the desired mixer through an opening, 32, 32', in each of the mixers, 30, 30'. Desirably, the residence time of the pre-mix or master batch 22 is minimized in the mixers 30, 30'. While complete dispersion of the drug into the pre-mix or master batch 22 is desirable, excessive residence times may result in leaching or dissolving of the drug, especially in the case for a soluble drug. Thus, the mixers 30, 30' are often smaller, i.e. lower residence times, as compared to the primary mixers (not shown) used in forming the pre-mix or master batch 22. After the drug has been blended with the master batch pre-mix for a sufficient time to provide a uniform matrix, a specific amount of the uniform matrix is then fed to the pan 36 through the second metering pumps, 34, 34'. The metering roller 38 determines the thickness of the film 42 and applies it to the application roller. The film 42 is finally formed on the substrate 44 and carried away via the support roller 46.

While the proper viscosity uniformity in mixture and stable suspension of particles, and casting method are important in the initial steps of forming the composition and film to promote uniformity, the method of drying the wet film is also important. Although these parameters and properties assist uniformity initially, a controlled rapid drying process ensures that the uniformity will be maintained until the film is dry.

The wet film is then dried using controlled bottom drying or controlled microwave drying, desirably in the absence of external air currents or heat on the top (exposed) surface of the film 48 as described herein. Controlled bottom drying or controlled microwave drying advantageously allows for vapor release from the film without the disadvantages of the prior art. Conventional convection air drying from the top is not employed because it initiates drying at the top uppermost portion of the film, thereby forming a barrier against fluid flow, such as the evaporative vapors, and thermal flow, such as the thermal energy for drying. Such dried upper portions serve as a barrier to further vapor release as the portions beneath are dried, which results in non-uniform films. As previously mentioned some top air flow can be used to aid the drying of the films of the present invention, but it must not create a condition that would cause particle movement or a rippling effect in the film, both of which would result in non-uniformity. If top air is employed, it is balanced with the bottom air drying to avoid non-uniformity and prevent film lift-up on the carrier belt. A balance top and bottom air flow may be suitable where the bottom air flow functions as the major SOURSce of drying and the top air flow is the minor SOURSce of drying. The advantage of some top air flow is to move the exiting vapors away from the film thereby aiding in the overall drying process. The use of any top air flow or top drying, however, must be balanced by a number of factors including, but not limited, to rheological properties of the composition and mechanical aspects of the processing. Any top fluid flow, such as air, also must not overcome the inherent viscosity of the film-forming composition. In other words, the top air flow cannot break, distort or otherwise physically disturb the surface of the composition. Moreover, air velocities are desirably below the yield values of the film, i.e., below any force level that can move the liquids in the film-forming compositions. For thin or low viscosity compositions, low air velocity must be used. For thick or high viscosity compositions, higher air velocities may be used. Furthermore, air velocities are desirable low so as to avoid any lifting or other movement of the film formed from the compositions.

Moreover, the films of the present invention may contain particles that are sensitive to temperature, such as flavors, which may be volatile, or drugs, which may have a low degradation temperature. In such cases, the drying temperature may be decreased while increasing the drying time to adequately dry the uniform films of the present invention. Furthermore, bottom drying also tends to result in a lower internal film temperature as compared to top drying. In bottom drying, the evaporating vapors more readily carry heat away from the film as compared to top drying which lowers the internal film temperature. Such lower internal film temperatures often result in decreased drug degradation and decreased loss of certain volatiles, such as flavors.

Furthermore, particles or particulates may be added to the film-forming composition or matrix after the composition or matrix is cast into a film. For example, particles may be added to the film 42 prior to the drying of the film 42. Particles may be controllably metered to the film and disposed onto the film through a suitable technique, such as through the use of a doctor blade (not shown) which is a device which marginally or softly touches the surface of the film and controllably disposes the particles onto the film surface. Other suitable, but non-limiting, techniques include the use of an additional roller to place the particles on the film surface, spraying the particles onto the film surface, and the like. The particles may be placed on either or both of the opposed film surfaces, i.e., the top and/or bottom film surfaces. Desirably, the particles are securably disposed onto the film, such as being embedded into the film. Moreover, such particles are desirably not fully encased or fully embedded into the film, but remain exposed to the surface of the film, such as in the case where the particles are partially embedded or partially encased.

The particles may be any useful organoleptic agent, cosmetic agent, pharmaceutical agent, or combinations thereof. Desirably, the pharmaceutical agent is a taste-masked or a controlled-release pharmaceutical agent. Useful organoleptic agents include flavors and sweeteners. Useful cosmetic agents include breath freshening or decongestant agents, such as menthol, including menthol crystals.

Figure 7:
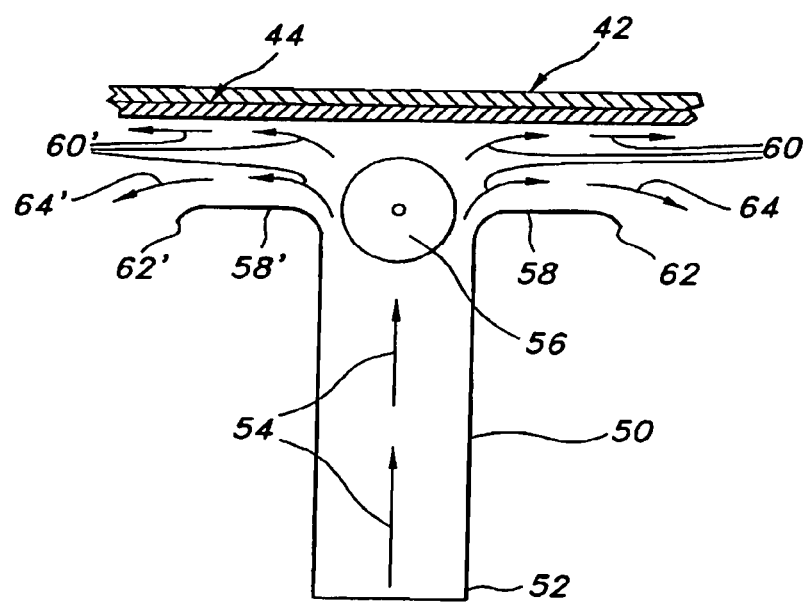
FIG. 7 is a schematic view of an apparatus suitable for drying the films of the present invention.

Although the inventive process is not limited to any particular apparatus for the above-described desirable drying, one particular useful drying apparatus 50 is depicted in FIG. 7. Drying apparatus 50 is a nozzle arrangement for directing hot fluid, such as but not limited to hot air, towards the bottom of the film 42 which is disposed on substrate 44. Hot air enters the entrance end 52 of the drying apparatus and travels vertically upward, as depicted by vectors 54, towards air deflector 56. The air deflector 56 redirects the air movement to minimize upward force on the film 42. As depicted in FIG. 7, the air is tangentially directed, as indicated by vectors 60 and 60', as the air passes by air deflector 56 and enters and travels through chamber portions 58 and 58' of the drying apparatus 50. With the hot air flow being substantially tangential to the film 42, lifting of the film as it is being dried is thereby minimized. While the air deflector 56 is depicted as a roller, other devices and geometries for deflecting air or hot fluid may suitable be used. Furthermore, the exit ends 62 and 62' of the drying apparatus 50 are flared downwardly. Such downward flaring provides a downward force or downward velocity vector, as indicated by vectors 64 and 64', which tend to provide a pulling or drag effect of the film 42 to prevent lifting of the film 42. Lifting of the film 42 may not only result in non-uniformity in the film or otherwise, but may also result in non-controlled processing of the film 42 as the film 42 and/or substrate 44 lift away from the processing equipment.

Monitoring and control of the thickness of the film also contributes to the production of a uniform film by providing a film of uniform thickness. The thickness of the film may be monitored with gauges such as Beta Gauges. A gauge may be coupled to another gauge at the end of the drying apparatus, i.e. drying oven or tunnel, to communicate through feedback loops to control and adjust the opening in the coating apparatus, resulting in control of uniform film thickness.

The film products are generally formed by combining a properly selected polymer and polar solvent, as well as any active ingredient or filler as desired. Desirably, the solvent content of the combination is at least about 30% by weight of the total combination. The matrix formed by this combination is formed into a film, desirably by roll coating, and then dried, desirably by a rapid and controlled drying process to maintain the uniformity of the film, more specifically, a non-self-aggregating uniform heterogeneity. The resulting film will desirably contain less than about 10% by weight solvent, more desirably less than about 8% by weight solvent, even more desirably less than about 6% by weight solvent and most desirably less than about 2%. The solvent may be water, a polar organic solvent including, but not limited to, ethanol, isopropanol, acetone, methylene chloride, or any combination thereof.

Consideration of the above discussed parameters, such as but not limited to rheology properties, viscosity, mixing method, casting method and drying method, also impact material selection for the different components of the present invention. Furthermore, such consideration with proper material selection provides the compositions of the present invention, including a pharmaceutical and/or cosmetic dosage form or film product having no more than a 10% variance of a pharmaceutical and/or cosmetic active per unit area. In other words, the uniformity of the present invention is determined by the presence of no more than a 10% by weight of pharmaceutical and/or cosmetic variance throughout the matrix. Desirably, the variance is less than 5% by weight, less than 2% by weight, less than 1% by weight, or less than 0.5% by weight.

Film-Forming Polymers

The polymer may be water soluble, water swellable, water insoluble, or a combination of one or more either water soluble, water swellable or water insoluble polymers. The polymer may include cellulose or a cellulose derivative. Specific examples of useful water soluble polymers include, but are not limited to, polyethylene oxide (PEO), pullulan, hydroxypropylmethyl cellulose, hydroxyethyl cellulose, hydroxypropyl cellulose, polyvinyl pyrrolidone, carboxymethyl cellulose, polyvinyl alcohol, sodium aginate, polyethylene glycol, xanthan gum, tragancanth gum, guar gum, acacia gum, arabic gum, polyacrylic acid, methylmethacrylate copolymer, carboxyvinyl copolymers, starch, gelatin, and combinations thereof. In some embodiments, combinations of PEO and a cellulosic polymer, such as hydroxypropyl cellulose, are employed. Specific examples of useful water insoluble polymers include, but are not limited to, ethyl cellulose, hydroxypropyl ethyl cellulose, cellulose acetate phthalate, hydroxypropyl methyl cellulose phthalate and combinations thereof.

As used herein the phrase "water soluble polymer" and variants thereof refer to a polymer that is at least partially soluble in water, and desirably fully or predominantly soluble in water, or absorbs water. Polymers that absorb water are often referred to as being water swellable polymers. The materials useful with the present invention may be water soluble or water swellable at room temperature and other temperatures, such as temperatures exceeding room temperature. Moreover, the materials may be water soluble or water swellable at pressures less than atmospheric pressure. Desirably, the water soluble polymers are water soluble or water swellable having at least 20 percent by weight water uptake. Water swellable polymers having a 25 or greater percent by weight water uptake are also useful. Films or dosage forms of the present invention formed from such water soluble polymers are desirably sufficiently water soluble to be dissolvable upon contact with bodily fluids.

Other polymers useful for incorporation into the films of the present invention include biodegradable polymers, copolymers, block polymers and combinations thereof. Among the known useful polymers or polymer classes which meet the above criteria are: poly(glycolic acid) (PGA), poly(lactic acid)(PLA), polydioxanoes, polyoxalates, poly($\alpha$-esters), polyanhydrides, polyacetates, polycaprolactones, poly(orthoesters), polyamino acids, polyaminocarbonates, polyurethanes, polycarbonates, polyamides, poly(alkyl cyanoacrylates), and mixtures and copolymers thereof. Additional useful polymers include, stereopolymers of L- and D-lactic acid, copolymers of bis(p-carboxyphenoxy) propane acid and sebacic acid, sebacic acid copolymers, copolymers of caprolactone, poly(lactic acid)/poly(glycolic acid)/polyethyleneglycol copolymers, copolymers of polyurethane and (poly(lactic acid), copolymers of polyurethane and poly(lactic acid), copolymers of $\alpha$-amino acids, copolymers of $\alpha$-amino acids and caproic acid, copolymers of $\alpha$-benzyl glutamate and polyethylene glycol, copolymers of succinate and poly(glycols), polyphosphazene, polyhydroxy-alkanoates and mixtures thereof. Binary and ternary systems are contemplated.

Other specific polymers useful include those marketed under the Medisorb and Biodel trademarks. The Medisorb materials are marketed by the Dupont Company of Wilmington, Del. and are generically identified as a "lactide/glycolide co-polymer" containing "propanoic acid, 2-hydroxy-polymer with hydroxyacetic acid." Four such polymers include lactide/glycolide 100 L, believed to be 100% lactide having a melting point within the range of 338°–347° F. (170°–175° C.); lactide/glycolide 100 L, believed to be 100% glycolide having a melting point within the range of 437°–455° F. (22-235° C.); lactide/glycolide 85/15, believed to be 85% lactide and 15% glycolide with a melting point within the range of 338°–347° F. (170°–175° C.); and lactide/glycolide 50/50, believed to be a copolymer of 50% lactide and 50% glycolide with a melting point within the range of 338°-347° F. (170°–175° C.).

The Biodel materials represent a family of various polyanhydrides which differ chemically.

Although a variety of different polymers may be used, it is desired to select polymers to provide a desired viscosity of the mixture prior to drying. For example, if the active or other components are not soluble in the selected solvent, a polymer that will provide a greater viscosity is desired to assist in maintaining uniformity. On the other hand, if the components are soluble in the solvent, a polymer that provides a lower viscosity may be preferred.

The polymer plays an important role in affecting the viscosity of the film. Viscosity is one property of a liquid that controls the stability of the active in an emulsion, a colloid or a suspension. Generally the viscosity of the matrix will vary from about 400 cps to about 100,000 cps, preferably from about 800 cps to about 60,000 cps, and most preferably from about 1,000 cps to about 40,000 cps. Desirably, the viscosity of the film-forming matrix will rapidly increase upon initiation of the drying process.

The viscosity may be adjusted based on the selected active depending on the other components within the matrix. For example, if the component is not soluble within the selected solvent, a proper viscosity may be selected to prevent the component from settling which would adversely affect the uniformity of the resulting film. The viscosity may be adjusted in different ways. To increase viscosity of the film matrix, the polymer may be chosen of a higher molecular weight or crosslinkers may be added, such as salts of calcium, sodium and potassium. The viscosity may also be adjusted by adjusting the temperature or by adding a viscosity increasing component. Components that will increase the viscosity or stabilize the emulsion/suspension include higher molecular weight polymers and polysaccharides and gums, which include without limitation, alginate, carrageenan, hydroxypropyl methyl cellulose, locust bean gum, guar gum, xanthan gum, dextran, gum arabic, gellan gum and combinations thereof.

It has also been observed that certain polymers which when used alone would ordinarily require a plasticizer to achieve a flexible film, can be combined without a plasticizer and yet achieve flexible films. For example, HPMC and HPC when used in combination provide a flexible, strong film with the appropriate plasticity and elasticity for manufacturing and storage. No additional plasticizer or polyalcohol is needed for flexibility.

Controlled Release Films

The term "controlled release" is intended to mean the release of active at a pre-selected or desired rate. This rate will vary depending upon the application. Desirable rates include fast or immediate release profiles as well as delayed, sustained or sequential release. Combinations of release patterns, such as initial spiked release followed by lower levels of sustained release of active are contemplated. Pulsed drug releases are also contemplated.

The polymers that are chosen for the films of the present invention may also be chosen to allow for controlled disintegration of the active. This may be achieved by providing a substantially water insoluble film that incorporates an active that will be released from the film over time. This may be accomplished by incorporating a variety of different soluble or insoluble polymers and may also include biodegradable polymers in combination. Alternatively, coated controlled release active particles may be incorporated into a readily soluble film matrix to achieve the controlled release property of the active inside the digestive system upon consumption.

Films that provide a controlled release of the active are particularly useful for buccal, gingival, sublingual and vaginal applications. The films of the present invention are particularly useful where mucosal membranes or mucosal fluid is present due to their ability to readily wet and adhere to these areas.

The convenience of administering a single dose of a medication which releases active ingredients in a controlled fashion over an extended period of time as opposed to the administration of a number of single doses at regular intervals has long been recognized in the pharmaceutical arts. The advantage to the patient and clinician in having consistent and uniform blood levels of medication over an extended period of time are likewise recognized. The advantages of a variety of sustained release dosage forms are well known. However, the preparation of a film that provides the controlled release of an active has advantages in addition to those well-known for controlled release tablets. For example, thin films are difficult to inadvertently aspirate and provide an increased patient compliance because they need not be swallowed like a tablet. Moreover, certain embodiments of the inventive films are designed to adhere to the buccal cavity and tongue, where they controllably dissolve. Furthermore, thin films may not be crushed in the manner of controlled release tablets which is a problem leading to abuse of drugs such as Oxycontin.

The actives employed in the present invention may be incorporated into the film compositions of the present invention in a controlled release form. For example, particles of drug may be coated with polymers such as ethyl cellulose or polymethacrylate, commercially available under brand names such as Aquacoat ECD and Eudragit E-100, respectively. Solutions of drug may also be absorbed on such polymer materials and incorporated into the inventive film compositions. Other components such as fats and waxes, as well as sweeteners and/or flavors may also be employed in such controlled release compositions.

The actives may be taste-masked prior to incorporation into the film composition, as set forth in co-pending PCT application titled, Uniform Films For Rapid Dissolve Dosage Form Incorporating Taste-Masking Compositions, (based on U.S. Provisional Application No. Express Mail Label No.: EU552991605 US of the same title, filed Sep. 27, 2003, the entire subject matter of which is incorporated by reference herein.

Actives

When an active is introduced to the film, the amount of active per unit area is determined by the uniform distribution of the film. For example, when the films are cut into individual dosage forms, the amount of the active in the dosage form can be known with a great deal of accuracy. This is achieved because the amount of the active in a given area is substantially identical to the amount of active in an area of the same dimensions in another part of the film. The accuracy in dosage is particularly advantageous when the active is a medicament, i.e. a drug.

The active components that may be incorporated into the films of the present invention include, without limitation pharmaceutical and cosmetic actives, drugs, medicaments, antigens or allergens such as ragweed pollen, spores, microorganisms including bacteria, seeds, mouthwash components such as chlorates or chlorites, flavors, fragrances, enzymes, preservatives, sweetening agents, colorants, spices, vitamins and combinations thereof.

A wide variety of medicaments, bioactive active substances and pharmaceutical compositions may be included in the dosage forms of the present invention. Examples of useful drugs include ace-inhibitors, antianginal drugs, anti-arrhythmias, anti-asthmatics, anti-cholesterolemics, analgesics, anesthetics, anti-convulsants, anti-depressants, anti-diabetic agents, anti-diarrhea preparations, antidotes, anti-histamines, anti-hypertensive drugs, anti-inflammatory agents, anti-lipid agents, anti-manics, anti-nauseants, anti-stroke agents, anti-thyroid preparations, anti-tumor drugs, anti-viral agents, acne drugs, alkaloids, amino acid preparations, anti-tussives, anti-uricemic drugs, anti-viral drugs, anabolic preparations, systemic and non-systemic anti-infective agents, anti-neoplastics, anti-parkinsonian agents, anti-rheumatic agents, appetite stimulants, biological response modifiers, blood modifiers, bone metabolism regulators, cardiovascular agents, central nervous system stimulates, cholinesterase inhibitors, contraceptives, decongestants, dietary supplements, dopamine receptor agonists, endometriosis management agents, enzymes, erectile dysfunction therapies, fertility agents, gastrointestinal agents, homeopathic remedies, hormones, hypercalcemia and hypocalcemia management agents, immunomodulators, immunosuppressives, migraine preparations, motion sickness treatments, muscle relaxants, obesity management agents, osteoporosis preparations, oxytocics, parasympatholytics, parasympathomimetics, prostaglandins, psychotherapeutic agents, respiratory agents, sedatives, smoking cessation aids such as bromocryptine and nicotine, sympatholytics, tremor preparations, urinary tract agents, vasodilators, laxatives, antacids, ion exchange resins, anti-pyretics, appetite suppressants, expectorants, anti-anxiety agents, anti-ulcer agents, anti-inflammatory substances, coronary dilators, cerebral dilators, peripheral vasodilators, psycho-tropics, stimulants, anti-hypertensive drugs, vasoconstrictors, migraine treatments, antibiotics, tranquilizers, anti-psychotics, anti-tumor drugs, anti-coagulants, anti-thrombotic drugs, hypnotics, anti-emetics, anti-nauseants, anti-convulsants, neuromuscular drugs, hyper- and hypo-glycemic agents, thyroid and anti-thyroid preparations, diuretics, anti-spasmodics, terine relaxants, anti-obesity drugs, erythropoietic drugs, anti-asthmatics, cough suppressants, mucolytics, DNA and genetic modifying drugs, and combinations thereof.

Examples of medicating active ingredients contemplated for use in the present invention include antacids, H$_2$-antagonists, and analgesics. For example, antacid dosages can be prepared using the ingredients calcium carbonate alone or in combination with magnesium hydroxide, and/or aluminum hydroxide. Moreover, antacids can be used in combination with H$_2$-antagonists.

Analgesics include opiates and opiate derivatives, such as oxycodone (available as Oxycontin®), ibuprofen, aspirin, acetaminophen, and combinations thereof that may optionally include caffeine.

Other preferred drugs for other preferred active ingredients for use in the present invention include anti-diarrheals such as immodium AD, anti-histamines, anti-tussives, decongestants, vitamins, and breath fresheners. Suitable vitamins contemplated for use herein include any conventionally known vitamins, such as, but not limited to, Vitamins A, B, C and E. Common drugs used alone or in combination for colds, pain, fever, cough, congestion, runny nose and allergies, such as acetaminophen, chlorpheniramine maleate, dextromethorphan, pseudoephedrine HCl and diphenhydramine may be included in the film compositions of the present invention.

Also contemplated for use herein are anxiolytics such as alprazolam (available as Xanax®); anti-psychotics such as clozopin (available as Clozaril®) and haloperidol (available as Haldol®); non-steroidal anti-inflammatories (NSAID's) such as dicyclofenacs (available as Voltaren®) and etodolac (available as Lodine®), anti-histamines such as loratadine (available as Claritin®), astemizole (available as Hismanal™), nabumetone (available as Relafen®), and Clemastine (available as Tavist®); anti-emetics such as granisetron hydrochloride (available as Kytril®) and nabilone (available as Cesamet™); bronchodilators such as Bentolin®, albuterol sulfate (available as Proventil®); anti-depressants such as fluoxetine hydrochloride (available as Prozac®), sertraline hydrochloride (available as Zoloft®), and paroxtine hydrochloride (available as Paxil®); anti-migraines such as Imigra®, ACE-inhibitors such as enalaprilat (available as Vasotec®), captopril (available as Capoten®) and lisinopril (available as Zestril®); anti-Alzheimer's agents, such as nicergoline; and Ca-antagonists such as nifedipine (available as Procardia® and Adalat®), and verapamil hydrochloride (available as Calan®).

Erectile dysfunction therapies include, but are not limited to, drugs for facilitating blood flow to the penis, and for effecting autonomic nervous activities, such as increasing parasympathetic (cholinergic) and decreasing sympathetic (adrenersic) activities. Useful non-limiting drugs include sildenafls, such as Viagra®, tadalafils, such as Cialis®, vardenafils, apomorphines, such as Uprima®, yohimbine hydrochlorides such as Aphrodyne®, and alprostadils such as Caverject®.

The popular $H_2$-antagonists which are contemplated for use in the present invention include cimetidine, ranitidine hydrochloride, famotidine, nizatidien, ebrotidine, mifentidine, roxatidine, pisatidine and aceroxatidine.

Active antacid ingredients include, but are not limited to, the following: aluminum hydroxide, dihydroxyaluminum aminoacetate, aminoacetic acid, aluminum phosphate, dihydroxyaluminum sodium carbonate, bicarbonate, bismuth aluminate, bismuth carbonate, bismuth subcarbonate, bismuth subgallate, bismuth subnitrate, bismuth subsilysilate, calcium carbonate, calcium phosphate, citrate ion (acid or salt), amino acetic acid, hydrate magnesium aluminate sulfate, magaldrate, magnesium aluminosilicate, magnesium carbonate, magnesium glycinate, magnesium hydroxide, magnesium oxide, magnesium trisilicate, milk solids, aluminum mono-ordibasic calcium phosphate, tricalcium phosphate, potassium bicarbonate, sodium tartrate, sodium bicarbonate, magnesium aluminosilicates, tartaric acids and salts.

The pharmaceutically active agents employed in the present invention may include allergens or antigens, such as, but not limited to, plant pollens from grasses, trees, or ragweed; animal danders, which are tiny scales shed from the skin and hair of cats and other furred animals; insects, such as house dust mites, bees, and wasps; and drugs, such as penicillin.

Botanicals, herbals and minerals also may be added to the film. Examples of botanicals include, without limitation: roots; barks; leaves; stems; flowers; fruits; tobacco; sunflower seeds; snuff; and combinations thereof.

An anti-oxidant may also be added to the film to prevent the degradation of an active, especially where the active is photosensitive.

The bioactive active substances employed in the present invention may include beneficial bacteria. More specifically, certain bacteria normally exist on the surface of the tongue and in the back of the throat. Such bacteria assist in the digestion of food by breaking down proteins found in the food. It may be desirable, therefore, to incorporate these bacteria into the oral film products of the present invention.

It also may be desirable to include actives for treating breath malodor and related oral care conditions, such as actives which are effective in suppressing microorganisms. Because breath malodor can be caused by the presence of anaerobic bacteria in the oral cavity, which generate volatile sulfur compounds, components that suppress such microorganisms may be desirable. Examples of such components include antimicrobials such as triclosan, chlorine dioxide, chlorates, and chlorites, among others. The use of chlorites, particularly sodium chlorite, in oral care compositions such as mouthrinses and toothpastes is taught in U.S. Pat. Nos. 6,251,372, 6,132,702, 6,077,502, and U.S. Publication No. 2003/0129144, all of which are incorporated herein by reference. Such components are incorporated in amounts effective to treat malodor and related oral conditions.

Cosmetic active agents may include breath freshening compounds like menthol, other flavors or fragrances, especially those used for oral hygiene, as well as actives used in dental and oral cleansing such as quaternary ammonium bases. The effect of flavors may be enhanced using flavor enhancers like tartaric acid, citric acid, vanillin, or the like.

Also color additives can be used in preparing the films. Such color additives include food, drug and cosmetic colors (FD&C), drug and cosmetic colors (D&C), or external drug and cosmetic colors (Ext. D&C). These colors are dyes, their corresponding lakes, and certain natural and derived colorants. Lakes are dyes absorbed on aluminum hydroxide.

Other examples of coloring agents include known azo dyes, organic or inorganic pigments, or coloring agents of natural origin. Inorganic pigments are preferred, such as the oxides or iron or titanium, these oxides, being added in concentrations ranging from about 0.001 to about 10%, and preferably about 0.5 to about 3%, based on the weight of all the components.

Flavors may be chosen from natural and synthetic flavoring liquids. An illustrative list of such agents includes volatile oils, synthetic flavor oils, flavoring aromatics, oils, liquids, oleoresins or extracts derived from plants, leaves, flowers, fruits, stems and combinations thereof. A non-limiting representative list of examples includes mint oils, cocoa, and citrus oils such as lemon, orange, grape, lime and grapefruit and fruit essences including apple, pear, peach, grape, strawberry, raspberry, cherry, plum, pineapple, apricot or other fruit flavors.

The films containing flavorings may be added to provide a hot or cold flavored drink or soup. These flavorings include, without limitation, tea and soup flavorings such as beef and chicken.

Other useful flavorings include aldehydes and esters such as benzaldehyde (cherry, almond), citral i.e., alphacitral (lemon, lime), neral, i.e., beta-citral (lemon, lime), decanal (orange, lemon), aldehyde C-8 (citrus fruits), aldehyde C-9 (citrus fruits), aldehyde C-12 (citrus fruits), tolyl aldehyde (cherry, almond), 2,6-dimethyloctanol (green fruit), and 2-dodecenal (citrus, mandarin), combinations thereof and the like.

The sweeteners may be chosen from the following non-limiting list: glucose (corn syrup), dextrose, invert sugar, fructose, and combinations thereof; saccharin and its various salts such as the sodium salt; dipeptide sweeteners such as aspartame; dihydrochalcone compounds, glycyrrhizin; *Stevia Rebaudiana* (Stevioside); chloro derivatives of sucrose such as sucralose; sugar alcohols such as sorbitol, mannitol, xylitol, and the like. Also contemplated are hydrogenated starch hydrolysates and the synthetic sweetener 3,6-dihydro-6-methyl-1-1-1,2,3-oxathiazin-4-one-2,2-dioxide, particularly the potassium salt (acesulfame-K), and sodium and calcium salts thereof, and natural intensive sweeteners, such as Lo Han Kuo. Other sweeteners may also be used.

When the active is combined with the polymer in the solvent, the type of matrix that is formed depends on the solubilities of the active and the polymer. If the active and/or polymer are soluble in the selected solvent, this may form a solution. However, if the components are not soluble, the matrix may be classified as an emulsion, a colloid, or a suspension.

Dosages

The film products of the present invention are capable of accommodating a wide range of amounts of the active ingredient. The films are capable of providing an accurate dosage amount (determined by the size of the film and concentration of the active in the original polymer/water combination) regardless of whether the required dosage is high or extremely low. Therefore, depending on the type of active or pharmaceutical composition that is incorporated into the film, the active amount may be as high as about 300 mg, desirably up to about 150 mg or as low as the microgram range, or any amount therebetween.

The film products and methods of the present invention are well suited for high potency, low dosage drugs. This is accomplished through the high degree of uniformity of the films. Therefore, low dosage drugs, particularly more potent racemic mixtures of actives are desirable.

Anti-Tacking Compositions

03) It is useful to add anti-tacking agents, such as lubricants, antiadherants and glidants to the film compositions of the present invention. Anti-tacking agents assist in the flow characteristics of the material, for example, by reducing sticking to the die in extrusion processes and reducing sticking to the roof of the mouth during administration of the dosage form.

During consumption of films, particles tend to adhere to the roof of the mouth. This is undesirable for films containing bitter drugs, such as, for example, dextromethorphan, because the adhered particles elude drug, which increases the amount of bitterness detected by the user. Addition of an anti-tacking agent to the films reduces adherence to the roof of the mouth, thereby effectively reducing the bitterness that may be detected by a user during consumption.

Anti-taking agents also may impart reduced film-to-film coefficient of friction, thereby reducing the problem of film dosage units, i.e., strips, adhering to one another. More specifically, in many types of film packaging, strips are stacked against one another. The incorporation of anti-tacking agents may permit the individual strips to slide smoothly against one another as each unit is removed from the packaging.

Examples of suitable lubricants for use as anti-tacking agents include, but are not limited to: stearates, such as magnesium stearate, calcium stearate, and sodium stearate; stearic acid; sterotex; talc; waxes; stearowet; boric acid; sodium benzoate; sodium acetate; sodium chloride; DL-Leucine; Carbowax 4000; Carbowax 6000; sodium oleate; sodium lauryl sulfate; magnesium lauryl sulfate; and combinations thereof.

Examples of suitable antiadherants include, but are not limited to: talc; cornstarch; Cab-O-Sil; syloid; DL-Leucine; sodium lauryl sulfate; metallic stearates; and combinations thereof. Examples of suitable glidants include, but are not limited to: talc; cornstarch; Cab-O-Sil; syloid; aerosol; and combinations thereof.

Some embodiments of the present invention include fats and/or waxes as anti-tacking agents.

Vitamin E is another suitable anti-tacking agent for use in some embodiments of the present invention. Vitamin E may serve as both an anti-tacking agent and an active component in the film. Desirably, Vitamin E TPGS (d-alpha tocopheryl polyethylene glycol 1000 succinate) is employed. Vitamin E TPGS is a water-soluble form of Vitamin E derived from natural sources. As compared to other forms, Vitamin E TPGS is easily absorbed. Further, Vitamin E TPGS imparts practically no taste to film. Vitamin E TPGS may be employed in solution, such as, for example 10% or 20% solution with water. Vitamin E TPGS is particularly useful in reducing the stickiness of the films and the tendency to adhere to the roof of the user's mouth. Vitamin E may be present in amounts of about 0.01% to about 20% by weight of the composition.

Anti-tacking agents generally are present in amounts of about 0.01% to about 20% by weight of the film composition. More specifically, anti-tacking agents may be present in amounts of about 0.01% to about 10% by weight of the film composition, and even more specifically, about 0.25% to about 5% by weight of the film composition.

Combinations of anti-tacking agents also may be employed. For instance, in some embodiments of the present invention, a combination of a stearate, such as magnesium stearate, and silica may be used. SIPERNAT 500LS, which is a silica product having a 4.5 μm mean particle size, is suitable for use herein (commercially available from Degussa). Combinations of magnesium stearate and silica may provide improved glidant properties, i.e., assist film strips in sliding smoothly against one another in packaging. Accordingly, in some embodiments, magnesium stearate may be present in amounts of about 0.1% to about 2.5% by weight of the film composition and silica may be present in amounts of about 0.1% to about 1.5% by weight of the film composition. Such combination of anti-tacking agents may be useful in a variety of films containing different flavors and/or actives.

In some embodiments, anti-tacking agents may be included in the film composition itself. For example, single or multi-layer films including anti-tacking agents may be formed. Multi-layer films, for example, may include two, three or more layers of film substantially in contact with one another. In some embodiments, the film layers may be laminated to one another. Anti-tacking agents may be present in one or more of the layers of the multi-layer film. For example, some embodiments may include a bi-layer film in which anti-tacking agents are present in one of the two film layers. Some embodiments may include a three-layer film in which anti-tacking agents are present in each of the outer layers but not in the inner, or middle, layer of the three-layer film. In accordance therewith, a variety of different combinations of layers may be formed.

Alternatively, in some embodiments, anti-tacking agents may be included in a composition that is used to coat the external surfaces of the film. For instance, anti-tacking agents may be applied to the film in the form of a wet or dry coating, such as, for example, a sugared or sugar-free coating. The film may be coated with the anti-tacking agents in any conventional manner, such as, but not limited to, dip coating, spray coating, dusting, or fluidized bed. One or more film surfaces may be coated. In some embodiments, the anti-tacking coating may be applied to a substrate, such as a backing for the film, rather than directly to the film itself. When the film is removed from the backing, the anti-tacking coating may adhere to the film.

Anti-Foaming and De-Foaming Compositions

Anti-foaming and/or de-foaming components may also be used with the films of the present invention. These components aid in the removal of air, such as entrapped air, from the film-forming compositions. As described above, such entrapped air may lead to non-uniform films. Simethicone is one particularly useful anti-foaming and/or de-foaming agent. The present invention, however, is not so limited and other anti-foam and/or de-foaming agents may suitable be used.

Simethicone is generally used in the medical field as a treatment for gas or colic in babies. Simethicone is a mixture of fully methylated linear siloxane polymers containing repeating units of polydimethylsiloxane which is stabilized with trimethylsiloxy end-blocking unites, and silicon dioxide. It usually contains 90.5-99% polymethylsiloxane and 4-7% silicon dioxide. The mixture is a gray, translucent, viscous fluid which is insoluble in water.

When dispersed in water, simethicone will spread across the surface, forming a thin film of low surface tension. In this way, simethicone reduces the surface tension of bubbles air located in the solution, such as foam bubbles, causing their collapse. The function of simethicone mimics the dual action of oil and alcohol in water. For example, in an oily solution any trapped air bubbles will ascend to the surface and dissipate more quickly and easily, because an oily liquid has a lighter density compared to a water solution. On the other hand, an alcohol/water mixture is known to lower water density as well as lower the water's surface tension. So, any air bubbles trapped inside this mixture solution will also be easily dissipated. Simethicone solution provides both of these advantages. It lowers the surface energy of any air bubbles that trapped inside the aqueous solution, as well as lowering the surface tension of the aqueous solution. As the result of this unique functionality, simethicone has an excellent anti-foaming property that can be used for physiological processes (anti-gas in stomach) as well as any for external processes that require the removal of air bubbles from a product.

In order to prevent the formation of air bubbles in the films of the present invention, the mixing step can be performed under vacuum. However, as soon as the mixing step is completed, and the film solution is returned to the normal atmosphere condition, air will be re-introduced into or contacted with the mixture. In many cases, tiny air bubbles will be again trapped inside this polymeric viscous solution. The incorporation of simethicone into the film-forming composition either substantially reduces or eliminates the formation of air bubbles.

Simethicone may be added to the film-forming mixture as an anti-foaming agent in an amount from about 0.01 weight percent to about 5.0 weight percent, more desirably from about 0.05 weight percent to about 2.5 weight percent, and most desirably from about 0.1 weight percent to about 1.0 weight percent.

Optional Components

A variety of other components and fillers may also be added to the films of the present invention. These may include, without limitation, surfactants; plasticizers which assist in compatibilizing the components within the mixture; polyalcohols; anti-foaming agents, such as silicone-containing compounds, which promote a smoother film surface by releasing oxygen from the film; and thermo-setting gels such as pectin, carageenan, and gelatin, which help in maintaining the dispersion of components.

The variety of additives that can be incorporated into the inventive compositions may provide a variety of different functions. Examples of classes of additives include excipients, lubricants, buffering agents, stabilizers, blowing agents, pigments, coloring agents, fillers, bulking agents, sweetening agents, flavoring agents, fragrances, release modifiers, adjuvants, plasticizers, flow accelerators, mold release agents, polyols, granulating agents, diluents, binders, buffers, absorbents, glidants, adhesives, anti-adherents, acidulants, softeners, resins, demulcents, solvents, surfactants, emulsifiers, elastomers and mixtures thereof. These additives may be added with the active ingredient(s).

Useful additives include, for example, gelatin, vegetable proteins such as sunflower protein, soybean proteins, cotton seed proteins, peanut proteins, grape seed proteins, whey proteins, whey protein isolates, blood proteins, egg proteins, acrylated proteins, water-soluble polysaccharides such as alginates, carrageenans, guar gum, agar-agar, xanthan gum, gellan gum, gum arabic and related gums (gum ghatti, gum karaya, gum tragancanth), pectin, water-soluble derivatives of cellulose: alkylcelluloses hydroxyalkylcelluloses and hydroxyalkylalkylcelluloses, such as methylcelulose, hydroxymethylcellulose, hydroxyethylcellulose, hydroxypropylcellulose, hydroxyethylmethylcellulose, hydroxypropylmethylcellulose, hydroxybutylmethylcellulose, cellulose esters and hydroxyalkylcellulose esters such as cellulose acetate phthalate (CAP), hydroxypropylmethylcellulose (HPMC); carboxyalkylcelluloses, carboxyalkylalkylcelluloses, carboxyalkylcellulose esters such as carboxymethylcellulose and their alkali metal salts; water-soluble synthetic polymers such as polyacrylic acids and polyacrylic acid esters, polymethacrylic acids and polymethacrylic acid esters, polyvinylacetates, polyvinylalcohols, polyvinylacetatephthalates (PVAP), polyvinylpyrrolidone (PVP), PVY/vinyl acetate copolymer, and polycrotonic acids; also suitable are phthalated gelatin, gelatin succinate, crosslinked gelatin, shellac, water soluble chemical derivatives of starch, cationically modified acrylates and methacrylates possessing, for example, a tertiary or quaternary amino group, such as the diethylaminoethyl group, which may be quaternized if desired; and other similar polymers.

Such extenders may optionally be added in any desired amount desirably within the range of up to about 80%, desirably about 3% to 50% and more desirably within the range of 3% to 20% based on the weight of all components.

Further additives may be inorganic fillers, such as the oxides of magnesium aluminum, silicon, titanium, etc. desirably in a concentration range of about 0.02% to about 3% by weight and desirably about 0.02% to about 1% based on the weight of all components.

Further examples of additives are plasticizers which include polyalkylene oxides, such as polyethylene glycols, polypropylene glycols, polyethylene-propylene glycols, organic plasticizers with low molecular weights, such as glycerol, glycerol monoacetate, diacetate or triacetate, triacetin, polysorbate, cetyl alcohol, propylene glycol, sorbitol, sodium diethylsulfosuccinate, triethyl citrate, tributyl citrate, and the like, added in concentrations ranging from about 0.5% to about 30%, and desirably ranging from about 0.5% to about 20% based on the weight of the polymer.

There may further be added compounds to improve the flow properties of the starch material such as animal or vegetable fats, desirably in their hydrogenated form, especially those which are solid at room temperature. These fats desirably have a melting point of 50° C. or higher. Preferred are tri-glycerides with $C_{12}$-, $C_{14}$-, $C_{16}$-, $C_{15}$-, $C_{18}$-, $C_{20}$- and $C_{22}$-fatty acids. These fats can be added alone without adding extenders or plasticizers and can be advantageously added alone or together with mono- and/or di-glycerides or phosphatides, especially lecithin. The mono- and di-glycerides are desirably derived from the types of fats described above, i.e. with $C_{12}$-, $C_{14}$-, $C_{16}$-, $C_{18}$-, $C_{20}$- and $C_{22}$-fatty acids.

The total amounts used of the fats, mono-, di-glycerides and/or lecithins are up to about 5% and preferably within the range of about 0.5% to about 2% by weight of the total composition It is further useful to add silicon dioxide, calcium silicate, or titanium dioxide in a concentration of about 0.02% to about 1% by weight of the total composition. These compounds act as texturizing agents.

These additives are to be used in amounts sufficient to achieve their intended purpose. Generally, the combination of certain of these additives will alter the overall release profile of the active ingredient and can be used to modify, i.e. impede or accelerate the release.

Lecithin is one surface active agent for use in the present invention. Lecithin can be included in the feedstock in an amount of from about 0.25% to about 2.00% by weight. Other surface active agents, i.e. surfactants, include, but are not limited to, cetyl alcohol, sodium lauryl sulfate, the Spans™ and Tweens™ which are commercially available from ICI Americas, Inc. Ethoxylated oils, including ethoxylated castor oils, such as Cremophor® EL which is commercially available from BASF, are also useful. Carbowax™ is yet another modifier which is very useful in the present invention. Tweens™ or combinations of surface active agents may be used to achieve the desired hydrophilic-lipophilic balance ("HLB"). The present invention, however, does not require the use of a surfactant and films or film-forming compositions of the present invention may be essentially free of a surfactant while still providing the desirable uniformity features of the present invention.

It may be further useful to add polydextrose to the films of the present invention. Polydextrose serves as a filler and solubility enhancer, i.e., it increases the dissolution time of the films in the oral cavity.

As additional modifiers which enhance the procedure and product of the present invention are identified, Applicants intend to include all such additional modifiers within the scope of the invention claimed herein.

Other ingredients include binders which contribute to the ease of formation and general quality of the films. Non-limiting examples of binders include starches, pregelatinize starches, gelatin, polyvinylpyrrolidone, methylcellulose, sodium carboxymethylcellulose, ethylcellulose, polyacrylamides, polyvinyloxoazolidone, and polyvinylalcohols.
Forming the Film The films of the present invention must be formed into a sheet prior to drying. After the desired components are combined to form a multi-component matrix, including the polymer, water, and an active or other components as desired, the combination is formed into a sheet or film, by any method known in the art such as extrusion, coating, spreading, casting or drawing the multi-component matrix. If a multi-layered film is desired, this may be accomplished by co-extruding more than one combination of components which may be of the same or different composition. A multi-layered film may also be achieved by coating, spreading, or casting a combination onto an already formed film layer.

Although a variety of different film-forming techniques may be used, it is desirable to select a method that will provide a flexible film, such as reverse roll coating. The flexibility of the film allows for the sheets of film to be rolled and transported for storage or prior to being cut into individual dosage forms. Desirably, the films will also be self-supporting or in other words able to maintain their integrity and structure in the absence of a separate support. Furthermore, the films of the present invention may be selected of materials that are edible or ingestible.

Coating or casting methods are particularly useful for the purpose of forming the films of the present invention. Specific examples include reverse roll coating, gravure coating, immersion or dip coating, metering rod or meyer bar coating, slot die or extrusion coating, gap or knife over roll coating, air knife coating, curtain coating, or combinations thereof, especially when a multi-layered film is desired.

Roll coating, or more specifically reverse roll coating, is particularly desired when forming films in accordance with the present invention. This procedure provides excellent control and uniformity of the resulting films, which is desired in the present invention. In this procedure, the coating material is measured onto the applicator roller by the precision setting of the gap between the upper metering roller and the application roller below it. The coating is transferred from the application roller to the substrate as it passes around the support roller adjacent to the application roller. Both three roll and four roll processes are common.

The gravure coating process relies on an engraved roller running in a coating bath, which fills the engraved dots or lines of the roller with the coating material. The excess coating on the roller is wiped off by a doctor blade and the coating is then deposited onto the substrate as it passes between the engraved roller and a pressure roller.

Offset Gravure is common, where the coating is deposited on an intermediate roller before transfer to the substrate.

In the simple process of immersion or dip coating, the substrate is dipped into a bath of the coating, which is normally of a low viscosity to enable the coating to run back into the bath as the substrate emerges.

In the metering rod coating process, an excess of the coating is deposited onto the substrate as it passes over the bath roller. The wire-wound metering rod, sometimes known as a Meyer Bar, allows the desired quantity of the coating to remain on the substrate. The quantity is determined by the diameter of the wire used on the rod.

In the slot die process, the coating is squeezed out by gravity or under pressure through a slot and onto the substrate. If the coating is 100% solids, the process is termed "Extrusion" and in this case, the line speed is frequently much faster than the speed of the extrusion. This enables coatings to be considerably thinner than the width of the slot.

The gap or knife over roll process relies on a coating being applied to the substrate which then passes through a "gap" between a "knife" and a support roller. As the coating and substrate pass through, the excess is scraped off.

Air knife coating is where the coating is applied to the substrate and the excess is "blown off" by a powerful jet from the air knife. This procedure is useful for aqueous coatings.

In the curtain coating process, a bath with a slot in the base allows a continuous curtain of the coating to fall into the gap between two conveyors. The object to be coated is passed along the conveyor at a controlled speed and so receives the coating on its upper face.

Drying the Film

The drying step is also a contributing factor with regard to maintaining the uniformity of the film composition. A controlled drying process is particularly important when, in the absence of a viscosity increasing composition or a composition in which the viscosity is controlled, for example by the selection of the polymer, the components within the film may have an increased tendency to aggregate or conglomerate. An alternative method of forming a film with an accurate dosage, that would not necessitate the controlled drying process, would be to cast the films on a predetermined well. With this method, although the components may aggregate, this will not result in the migration of the active to an adjacent dosage form, since each well may define the dosage unit per se.

When a controlled or rapid drying process is desired, this may be through a variety of methods. A variety of methods may be used including those that require the application of heat. The liquid carriers are removed from the film in a manner such that the uniformity, or more specifically, the non-self-aggregating uniform heterogeneity, that is obtained in the wet film is maintained.

Desirably, the film is dried from the bottom of the film to the top of the film. Desirably, substantially no air flow is present across the top of the film during its initial setting period, during which a solid, visco-elastic structure is formed. This can take place within the first few minutes, e.g. about the first 0.5 to about 4.0 minutes of the drying process. Controlling the drying in this manner, prevents the destruction and reformation of the film's top surface, which results from conventional drying methods. This is accomplished by forming the film and placing it on the top side of a surface having top and bottom sides. Then, heat is initially applied to the bottom side of the film to provide the necessary energy to evaporate or otherwise remove the liquid carrier. The films dried in this manner dry more quickly and evenly as compared to air-dried films, or those dried by conventional drying means. In contrast to an air-dried film that dries first at the top and edges, the films dried by applying heat to the bottom dry simultaneously at the center as well as at the edges. This also prevents settling of ingredients that occurs with films dried by conventional means.

The temperature at which the films are dried is about 100° C. or less, desirably about 90° C. or less, and most desirably about 80° C. or less.

Another method of controlling the drying process, which may be used alone or in combination with other controlled methods as disclosed above includes controlling and modifying the humidity within the drying apparatus where the film is being dried. In this manner, the premature drying of the top surface of the film is avoided.

Additionally, it has also been discovered that the length of drying time can be properly controlled, i.e. balanced with the heat sensitivity and volatility of the components, and particularly the flavor oils and drugs. The amount of energy, temperature and length and speed of the conveyor can be balanced to accommodate such actives and to minimize loss, degradation or ineffectiveness in the final film.

A specific example of an appropriate drying method is that disclosed by Magoon. Magoon is specifically directed toward a method of drying fruit pulp. However, the present inventors have adapted this process toward the preparation of thin films.

The method and apparatus of Magoon are based on an interesting property of water. Although water transmits energy by conduction and convection both within and to its surroundings, water only radiates energy within and to water. Therefore, the apparatus of Magoon includes a surface onto which the fruit pulp is placed that is transparent to infrared radiation. The underside of the surface is in contact with a temperature controlled water bath. The water bath temperature is desirably controlled at a temperature slightly below the boiling temperature of water. When the wet fruit pulp is placed on the surface of the apparatus, this creates a "refractance window." This means that infrared energy is permitted to radiate through the surface only to the area on the surface occupied by the fruit pulp, and only until the fruit pulp is dry. The apparatus of Magoon provides the films of the present invention with an efficient drying time reducing the instance of aggregation of the components of the film.

The films may initially have a thickness of about 500 µm to about 1,500 µm, or about 20 mils to about 60 mils, and when dried have a thickness from about 3 µm to about 250 µm, or about 0.1 mils to about 10 mils. Desirably, the dried films will have a thickness of about 2 mils to about 8 mils, and more desirably, from about 3 mils to about 6 mils.

Uses of Thin Films

The thin films of the present invention are well suited for many uses. The high degree of uniformity of the components of the film makes them particularly well suited for incorporating pharmaceuticals. Furthermore, the polymers used in construction of the films may be chosen to allow for a range of disintegration times for the films. A variation or extension in the time over which a film will disintegrate may achieve control over the rate that the active is released, which may allow for a sustained release delivery system. In addition, the films may be used for the administration of an active to any of several body surfaces, especially those including mucous membranes, such as oral, anal, vaginal, ophthalmological, the surface of a wound, either on a skin surface or within a body such as during surgery, and similar surfaces.

The films may be used to orally administer an active. This is accomplished by preparing the films as described above and introducing them to the oral cavity of a mammal. This film may be prepared and adhered to a second or support layer from which it is removed prior to use, i.e. introduction to the oral cavity. An adhesive may be used to attach the film to the support or backing material which may be any of those known in the art, and is preferably not water soluble. If an adhesive is used, it will desirably be a food grade adhesive that is ingestible and does not alter the properties of the active. Mucoadhesive compositions are particularly useful. The film compositions in many cases serve as mucoadhesives themselves.

The films may be applied under or to the tongue of the mammal. When this is desired, a specific film shape, corresponding to the shape of the tongue may be preferred. Therefore the film may be cut to a shape where the side of the film corresponding to the back of the tongue will be longer than the side corresponding to the front of the tongue. Specifically, the desired shape may be that of a triangle or trapezoid. Desirably, the film will adhere to the oral cavity preventing it from being ejected from the oral cavity and permitting more of the active to be introduced to the oral cavity as the film dissolves.

Another use for the films of the present invention takes advantage of the films' tendency to dissolve quickly when introduce to a liquid. An active may be introduced to a liquid by preparing a film in accordance with the present invention, introducing it to a liquid, and allowing it to dissolve. This may be used either to prepare a liquid dosage form of an active, or to flavor a beverage.

The films of the present invention are desirably packaged in sealed, air and moisture resistant packages to protect the active from exposure oxidation, hydrolysis, volatilization and interaction with the environment. Referring to FIG. 1, a packaged pharmaceutical dosage unit 10, includes each film 12 individually wrapped in a pouch or between foil and/or plastic laminate sheets 14. As depicted in FIG. 2, the pouches 10, 10' can be linked together with tearable or perforated joints 16. The pouches 10, 10' may be packaged in a roll as depicted in FIG. 5 or stacked as shown in FIG. 3 and sold in a dispenser 18 as shown in FIG. 4. The dispenser may contain a full supply of the medication typically prescribed for the intended therapy, but due to the thinness of the film and package, is smaller and more convenient than traditional bottles used for tablets, capsules and liquids. Moreover, the films of the present invention dissolve instantly upon contact with saliva or mucosal membrane areas, eliminating the need to wash the dose down with water.

Desirably, a series of such unit doses are packaged together in accordance with the prescribed regimen or treatment, e.g., a 10-90 day supply, depending on the particular therapy. The individual films can be packaged on a backing and peeled off for use.

The features and advantages of the present invention are more fully shown by the following examples which are provided for purposes of illustration, and are not to be construed as limiting the invention in any way.

EXAMPLES

Examples 1-2

Water-soluble thin film compositions were prepared using the amounts described in Table 1. In particular, composition 1 incorporated Vitamin E as an anti-tacking agent along with various other components. Composition 2 contained similar components to composition 1, but absent Vitamin E.

TABLE 1

| Component | Weight (g unless otherwise indicated) | |
| --- | --- | --- |
| | 1 | 2 |
| Polyethylene oxide | 2.8 | 3.5 |
| Hydroxypropyl cellulose | 2.8 | 3.5 |
| Polydextrose | 0.69 | 0.79 |
| Sucralose | 0.35 | 0.75 |
| Taste-Masking flavor[1] | 0.07 | 0 |
| Titanium dioxide | 0.07 | 0.18 |
| Coated dextromethorphan (45% w/w) | 5.56 | 6.94 |
| Mint flavor | 1.26 | 1.71 |
| Vitamin E[2] | 3.9 | 0 |
| WS-3[3] | 0.035 | 0.044 |
| Simethicone emulsion[4] | 0.035 | 0.09 |
| Water | 19.49 | 32.5 |
| Blue food color | 4 drops | 5 drops |

[1]Magna Sweet, available from Mafco Worldwide Corp.
[2]10% solution containing 0.39 g Vitamin E and 3.51 g water
[3]N-Ethyl-p-menthane-3-carboxamide cooling agent, available from Millennium Chemicals
[4]Available from Sentry The above components for each composition were combined by mixing until a uniform mixture was achieved, and then cast into films. In particular, the solutions were cast onto release paper (available from Griff Paper & Film) using a K Control Coater with a 350 micron smooth bar. The films were then dried at about 80° C. for about 10 minutes. Composition 1 was dried to a moisture level of about 2.68%, and composition 2 was dried to a moisture level of about 3.35%.

The dried films were tested for various properties, including dissolution testing to determine how long it will take the film to dissolve in the mouth and bend testing to determine flexibility of the film. In addition, a panel observed the tendency of the films to exhibit stickiness in the mouth and the tendency to adhere to the roof of the user's mouth.

To test dissolution rate, an approximately 20 mm by 100 mm piece of film, having a 2.85 g weight attached, was lowered into a 32.5° C. water bath to a depth of about 50 mm. The time required for the film to dissolve and separate into two pieces was determined (in seconds).

The films also were subject to bend testing, i.e., 1800 bend test. The dried films were placed in a moisture analyzer (HR73 Moisture Analyzer from Mettler Toledo) to obtain percent moisture and to remove any solvent (e.g. water) remaining in the films after drying at 80° C. in accordance with the present invention. The films then were creased to about 180° and observed for break. Films that broke during creasing were considered a failure. If the film did not break during creasing, a 200 g weight was dropped onto the creased film from a height of about 8.5 mm. Films that broke were considered a failure, and those that did not break were considered a pass. It should be noted, however, that this flexibility test is an extreme test. Films that failed this test are still considered operable within the scope of the present invention. More specifically, there may be certain applications that do not require such extreme flexibility properties.

Both films of compositions 1 and 2 exhibited adequate strength, good tear resistance, passed the 180° bend test both prior and subsequent to placement in the moisture analyzer and dissolved on the tongue at a moderate to fast rate. Composition 1, which contained Vitamin E, exhibited no stickiness in the mouth and did not exhibit a tendency to adhere to the roof of the user's mouth. Composition 2, in contrast, did not contain Vitamin E. Composition 2 exhibited stickiness and tendency to adhere to the roof of the mouth.

Examples 3-243

Water-soluble thin films were prepared incorporating silica and magnesium stearate as anti-tacking agents in the amounts described in Table 2. More specifically, various combinations of silica and magnesium stearate were incorporated into a variety of different film compositions as shown in the table below.

TABLE 2

| Example | Film description | Silica[1] (weight %) | Magnesium stearate (weight %) |
| --- | --- | --- | --- |
| 3 | SOURS | 1.5 | 2.0 |
| 4 | SOURS | 1.5 | 2.0 |
| 5 | SOURS | 1.5 | 2.0 |
| 6 | SOURS | 1.5 | 2.0 |
| 7 | SOURS | 1.5 | 2.0 |
| 8 | SOURS | 1.5 | 2.0 |
| 9 | SOURS | 1.5 | 2.0 |
| 10 | SOURS | 1.5 | 2.0 |
| 11 | SOURS | 1.5 | 2.0 |
| 12 | SOURS | 1.5 | 2.0 |
| 13 | SOURS | 1.5 | 2.0 |
| 14 | SOURS | 1.5 | 2.0 |
| 15 | BENZOCAINE/MENTHOL | 1.5 | 1.5 |
| 16 | BENZOCAINE/MENTHOL | 1.5 | 1.5 |
| 17 | BENZOCAINE/MENTHOL | 1.5 | 1.5 |
| 18 | BENZOCAINE/MENTHOL | 1.5 | 1.5 |
| 19 | BENZOCAINE/MENTHOL | 1.5 | 1.5 |
| 20 | SOURS | 2 | 2.5 |

TABLE 2-continued

| Example | Film description | Silica[1] (weight %) | Magnesium stearate (weight %) |
|---|---|---|---|
| 21 | SOURS | 1.5 | 2 |
| 22 | SOURS | 1.5 | 2 |
| 23 | SOURS | 1.5 | 2 |
| 24 | SOURS | 1.5 | 2 |
| 25 | SOURS | 1.5 | 2 |
| 26 | SOURS | 1.5 | 2 |
| 27 | SOURS | 1.5 | 2.5 |
| 28 | SOURS | 1.5 | 2.5 |
| 29 | SOURS | 1.5 | 2.5 |
| 30 | SOURS | 1.5 | 2.5 |
| 31 | SOURS | 1.5 | 2 |
| 32 | SOURS | 1.5 | 2 |
| 33 | SOURS | 1.5 | 2.5 |
| 34 | SOURS | 1.5 | 2.5 |
| 35 | SOURS | 1.5 | 2.5 |
| 36 | SOURS | 1.5 | 2.5 |
| 37 | SOURS | 1.5 | 2.5 |
| 38 | SOURS | 1.5 | 2.5 |
| 39 | SOURS | 1.5 | 2.5 |
| 40 | SOURS | 1.5 | 2.5 |
| 41 | ENERGY/WELLNESS SUPPLEMENT[2] | 1 | 2 |
| 42 | ENERGY/WELLNESS SUPPLEMENT[2] | 1 | 2 |
| 43 | ENERGY/WELLNESS SUPPLEMENT[2] | 0.9 | 1 |
| 44 | ENERGY/WELLNESS SUPPLEMENT[2] | 1.15 | 1 |
| 45 | ENERGY/WELLNESS SUPPLEMENT[2] | 1 | 1 |
| 46 | ENERGY/WELLNESS SUPPLEMENT[2] | 0.75 | 1 |
| 47 | ENERGY/WELLNESS SUPPLEMENT[2] | 1 | 1.5 |
| 48 | ENERGY/WELLNESS SUPPLEMENT[2] | 1 | 1 |
| 49 | ENERGY/WELLNESS SUPPLEMENT[2] | 0.75 | 1 |
| 50 | ENERGY/WELLNESS SUPPLEMENT[2] | 1 | 1 |
| 51 | ENERGY/WELLNESS SUPPLEMENT[2] | 1 | 1 |
| 52 | ENERGY/WELLNESS SUPPLEMENT[2] | 1 | 1 |
| 53 | ENERGY/WELLNESS SUPPLEMENT[2] | 1 | 1 |
| 54 | ENERGY/WELLNESS SUPPLEMENT[2] | 1 | 1 |
| 55 | ENERGY/WELLNESS SUPPLEMENT[2] | 1 | 1 |
| 56 | ENERGY/WELLNESS SUPPLEMENT[2] | 1 | 1 |
| 57 | ENERGY/WELLNESS SUPPLEMENT[2] | 1 | 1 |
| 58 | ENERGY/WELLNESS SUPPLEMENT[2] | 1 | 1 |
| 59 | ENERGY/WELLNESS SUPPLEMENT[2] | 1 | 1 |
| 60 | ENERGY/WELLNESS SUPPLEMENT[2] | 1 | 1 |
| 61 | ENERGY/WELLNESS SUPPLEMENT[2] | 1 | 1.5 |
| 62 | ENERGY/WELLNESS SUPPLEMENT[2] | 0.5 | 1.5 |
| 63 | ORAL ANALGESIC | 0.54 | 0.5 |
| 64 | ORAL ANALGESIC | 1.54 | 1 |
| 65 | ORAL ANALGESIC | 0.5 | 0.54 |
| 66 | ORAL ANALGESIC | 1.54 | 1 |
| 67 | ORAL ANALGESIC | 1.04 | 1 |
| 68 | ORAL ANALGESIC | 1.24 | 1.5 |
| 69 | ORAL ANALGESIC | 1.24 | 1.5 |
| 70 | ORAL ANALGESIC | 1.24 | 1.5 |
| 71 | ORAL ANALGESIC | 1.24 | 1.5 |
| 72 | ORAL ANALGESIC | 1.24 | 1.5 |
| 73 | ORAL ANALGESIC | 1.24 | 1.5 |
| 74 | ENERGY/WELLNESS SUPPLEMENT[2] | 0.5 | 1.5 |
| 75 | MELATONIN | 1 | 2 |
| 76 | MELATONIN | 1 | 2 |
| 77 | MELATONIN | 1 | 2 |
| 78 | MELATONIN | 1 | 1.5 |
| 79 | MELATONIN | 1.1 | 1.3 |
| 80 | MELATONIN | 1.2 | 1.3 |
| 81 | CHLORINE DIOXIDE | 1.5 | 1.5 |
| 82 | MULTIVITAMIN | 1 | 1 |
| 83 | MULTIVITAMIN | 1 | 1 |
| 84 | ZINC/ELDERBERRY | 0.5 | 1 |
| 85 | ENERGY/WELLNESS SUPPLEMENT[2] | 0.75 | 1 |
| 86 | ENERGY/WELLNESS SUPPLEMENT[2] | 0.75 | 1 |
| 87 | ENERGY/WELLNESS SUPPLEMENT[2] | 0.75 | 1 |
| 88 | MELATONIN | 1.1 | 1.3 |
| 89 | MULTIVITAMIN | 1 | 1 |
| 90 | B-COMPLEX VITAMIN | 1 | 1 |
| 91 | MULTIVITAMIN | 1 | 1 |
| 92 | B-COMPLEX VITAMIN | 1 | 1 |
| 93 | MULTIVITAMIN | 1 | 1 |
| 94 | MULTIVITAMIN | 1 | 1 |
| 95 | ENERGY/WELLNESS SUPPLEMENT[2] | 0.75 | 1 |
| 96 | MULTIVITAMIN | 1 | 1 |
| 97 | MELATONIN | 1 | 1 |
| 98 | ENERGY/WELLNESS SUPPLEMENT[2] | 0.75 | 1 |
| 99 | ENERGY/WELLNESS SUPPLEMENT[3] | 0.75 | 1 |
| 100 | ENERGY/WELLNESS SUPPLEMENT[2] | 0.75 | 1 |
| 101 | ENERGY/WELLNESS SUPPLEMENT[2] | 1 | 1.5 |
| 102 | ENERGY/WELLNESS SUPPLEMENT[2] | 1 | 1.5 |
| 103 | ENERGY/WELLNESS SUPPLEMENT[2] | 1 | 2 |
| 104 | ENERGY/WELLNESS SUPPLEMENT[2] | 1.5 | 1 |
| 105 | ENERGY/WELLNESS SUPPLEMENT[2] | 1 | 2 |
| 106 | ENERGY/WELLNESS SUPPLEMENT[2] | 1 | 2 |
| 107 | ENERGY/WELLNESS SUPPLEMENT[2] | 1 | 1.5 |
| 108 | ENERGY/WELLNESS SUPPLEMENT[2] | 1 | 2 |
| 109 | ENERGY/WELLNESS SUPPLEMENT[2] | 1 | 1.5 |
| 110 | ENERGY/WELLNESS SUPPLEMENT[2] | 1 | 1.5 |
| 111 | ENERGY/WELLNESS SUPPLEMENT[2] | 1 | 1.5 |
| 112 | ENERGY/WELLNESS SUPPLEMENT[2] | 1 | 1.5 |
| 113 | ENERGY/WELLNESS SUPPLEMENT[2] | 1 | 1.5 |
| 114 | ENERGY/WELLNESS SUPPLEMENT[2] | 1 | 1.5 |
| 115 | MULTIVITAMIN | 1 | 1.5 |
| 116 | MULTIVITAMIN | 1 | 1.5 |
| 117 | IMMUNE BOOSTER | 1 | 1 |
| 118 | MELATONIN | 1.1 | 1.3 |
| 119 | MELATONIN | 1.1 | 1.3 |
| 120 | MELATONIN | 1.1 | 1.3 |
| 121 | MELATONIN | 1.1 | 1.3 |
| 122 | MELATONIN | 0.5 | 0.75 |
| 123 | COLD & COUGH | 1 | 1 |
| 124 | COLD & COUGH | 1 | 1 |
| 125 | MULTIVITAMIN | 1 | 1 |
| 126 | MULTIVITAMIN | 1 | 1 |
| 127 | MULTIVITAMIN | 1 | 1.5 |

TABLE 2-continued

| Example | Film description | Silica[1] (weight %) | Magnesium stearate (weight %) |
|---|---|---|---|
| 128 | MULTIVITAMIN | 1 | 1 |
| 129 | MULTIVITAMIN | 1 | 1 |
| 130 | MULTIVITAMIN | 1 | 1.5 |
| 131 | MULTIVITAMIN | 1 | 1 |
| 132 | MULTIVITAMIN | 1 | 1 |
| 133 | B-COMPLEX VITAMIN | 1 | 1 |
| 134 | B-COMPLEX VITAMIN | 1 | 1 |
| 135 | B-COMPLEX VITAMIN | 1 | 1 |
| 136 | B-COMPLEX VITAMIN | 1 | 1 |
| 137 | ENERGY/WELLNESS SUPPLEMENT[2] | 1.5 | 1.5 |
| 138 | ENERGY/WELLNESS SUPPLEMENT[2] | 1.5 | 1.5 |
| 139 | ENERGY/WELLNESS SUPPLEMENT[2] | 1.5 | 1.5 |
| 140 | MULTIVITAMIN | 1 | 1 |
| 141 | B-COMPLEX VITAMIN | 1 | 1 |
| 142 | B-COMPLEX VITAMIN | 1 | 1 |
| 143 | MULTIVITAMIN | 1 | 1 |
| 144 | B-COMPLEX VITAMIN | 1 | 1 |
| 145 | MULTIVITAMIN | 1 | 1 |
| 146 | MULTIVITAMIN | 1 | 1 |
| 147 | MULTIVITAMIN | 1 | 1 |
| 148 | MULTIVITAMIN | 1 | 1 |
| 149 | B-COMPLEX VITAMIN | 1 | 1 |
| 150 | B-COMPLEX VITAMIN | 1 | 1 |
| 151 | MULTIVITAMIN | 1 | 1 |
| 152 | MULTIVITAMIN | 1 | 1 |
| 153 | MULTIVITAMIN | 1 | 1 |
| 154 | MULTIVITAMIN | 1.5 | 0.3 |
| 155 | ENERGY/WELLNESS SUPPLEMENT[2] | 1.5 | 1 |
| 156 | ENERGY/WELLNESS SUPPLEMENT[2] | 1 | 1 |
| 157 | ENERGY/WELLNESS SUPPLEMENT[2] | 1 | 1 |
| 158 | MULTIVITAMIN | 1 | 1 |
| 159 | MULTIVITAMIN | 1 | 1 |
| 160 | MULTIVITAMIN | 1.5 | 0.3 |
| 161 | MULTIVITAMIN | 1 | 1 |
| 162 | B-COMPLEX VITAMIN | 1 | 1 |
| 163 | B-COMPLEX VITAMIN | 1 | 1 |
| 164 | ENERGY/WELLNESS SUPPLEMENT[2] | 0.5 | 0.5 |
| 165 | ENERGY/WELLNESS SUPPLEMENT[2] | 0.5 | 0.5 |
| 166 | ENERGY/WELLNESS SUPPLEMENT[2] | 0.5 | 0.5 |
| 167 | ENERGY/WELLNESS SUPPLEMENT[2] | 0.5 | 0.5 |
| 168 | ENERGY/WELLNESS SUPPLEMENT[2] | 0.5 | 0.5 |
| 169 | ENERGY/WELLNESS SUPPLEMENT[2] | 0.5 | 0.5 |
| 170 | ENERGY/WELLNESS SUPPLEMENT[2] | 0.5 | 0.5 |
| 171 | ENERGY/WELLNESS SUPPLEMENT[2] | 1 | 0.5 |
| 172 | ENERGY/WELLNESS SUPPLEMENT[2] | 1 | 0.5 |
| 173 | MULTIVITAMIN | 1 | 1 |
| 174 | MULTIVITAMIN | 1 | 1 |
| 175 | ENERGY/WELLNESS SUPPLEMENT[2] | 0.5 | 0.5 |
| 176 | MULTIVITAMIN | 1 | 1 |
| 177 | ENERGY/WELLNESS SUPPLEMENT[2] | 0.5 | 0.5 |
| 178 | ENERGY/WELLNESS SUPPLEMENT[2] | 0.5 | 0.5 |
| 179 | MULTIVITAMIN | 1 | 1 |
| 180 | MULTIVITAMIN | 1 | 1 |
| 181 | ENERGY/WELLNESS SUPPLEMENT[2] | 1 | 0.5 |
| 182 | ENERGY/WELLNESS SUPPLEMENT[2] | 1 | 0.5 |
| 183 | MULTIVITAMIN | 1 | 1 |
| 184 | MULTIVITAMIN | 1 | 1 |
| 185 | MULTIVITAMIN | 1 | 1 |
| 186 | MULTIVITAMIN | 1 | 1 |
| 187 | MULTIVITAMIN | 1 | 1 |
| 188 | ENERGY/WELLNESS SUPPLEMENT[2] | 1 | 0.5 |
| 189 | MULTIVITAMIN | 1 | 1 |
| 190 | MULTIVITAMIN | 1 | 1 |
| 191 | MULTIVITAMIN | 1 | 1 |
| 192 | MULTIVITAMIN | 1 | 1 |
| 193 | MULTIVITAMIN | 1.37 | 2.05 |
| 194 | MULTIVITAMIN | 1 | 1 |
| 195 | MULTIVITAMIN | 1 | 1 |
| 196 | MULTIVITAMIN | 1 | 1 |
| 197 | B-COMPLEX VITAMIN | 1 | 1 |
| 198 | ENERGY/WELLNESS SUPPLEMENT[2] | 1 | 0.5 |
| 199 | ENERGY/WELLNESS SUPPLEMENT[2] | 1 | 0.5 |
| 200 | ENERGY/WELLNESS SUPPLEMENT[2] | 1 | 0.5 |
| 201 | B-COMPLEX VITAMIN | 1 | 1 |
| 202 | MULTIVITAMIN | 1 | 1 |
| 203 | MULTIVITAMIN | 1 | 1 |
| 204 | MELATONIN | 1.1 | 1.3 |
| 205 | MULTIVITAMIN | 1.5 | 0.3 |
| 206 | MULTIVITAMIN | 1 | 1 |
| 207 | STRESS RELIEF | 1 | 0.3 |
| 208 | MULTIVITAMIN | 1 | 1 |
| 209 | MULTIVITAMIN | 1 | 1 |
| 210 | MULTIVITAMIN | 1 | 1 |
| 211 | ENERGY/WELLNESS SUPPLEMENT[2] | 1 | 0.5 |
| 212 | ENERGY/WELLNESS SUPPLEMENT[2] | 1 | 0.5 |
| 213 | ENERGY/WELLNESS SUPPLEMENT[2] | 1 | 0.5 |
| 214 | ENERGY/WELLNESS SUPPLEMENT[2] | 1 | 0.5 |
| 215 | ENERGY/WELLNESS SUPPLEMENT[2] | 1 | 0.5 |
| 216 | MULTIVITAMIN | 1.5 | 0.3 |
| 217 | MELATONIN | 1 | 0.5 |
| 218 | MELATONIN | 1 | 0.5 |
| 219 | STRESS RELIEF | 1 | 0.3 |
| 220 | MULTIVITAMIN | 1 | 1 |
| 221 | MELATONIN | 1 | 0.5 |
| 222 | MULTIVITAMIN | 1.5 | 0.3 |
| 223 | MULTIVITAMIN | 1 | 1 |
| 224 | MULTIVITAMIN | 1 | 1 |
| 225 | CINNAMINT | 1 | 1 |
| 226 | MELATONIN | 1 | 0.5 |
| 227 | MELATONIN | 1 | 0.5 |
| 228 | B-COMPLEX VITAMIN | 1 | 1 |
| 229 | MULTIVITAMIN | 1 | 1 |
| 230 | MULTIVITAMIN | 1 | 1 |
| 231 | MULTIVITAMIN | 1 | 1 |
| 232 | MULTIVITAMIN | 1 | 1 |
| 233 | MULTIVITAMIN | 1 | 1 |
| 234 | MULTIVITAMIN | 1 | 1 |
| 235 | MULTIVITAMIN | 1 | 1 |
| 236 | MULTIVITAMIN | 1 | 1 |
| 237 | MULTIVITAMIN | 1 | 1 |
| 238 | MULTIVITAMIN | 1 | 1 |
| 239 | MULTIVITAMIN | 1 | 1 |
| 240 | MULTIVITAMIN | 1 | 1 |
| 241 | BENZOCAINE/MENTHOL | 1.5 | 1.5 |
| 242 | MULTIVITAMIN | 1 | 1 |
| 243 | DEXTROMETHORPHAN HYDROBROMIDE | 0.5 | 1.82 |

[1]Sipernat 500LS, available from Degussa
[2]Energy/Wellness Supplement may contain any/all of the following actives or combinations thereof: Green Tea, Guarana, Chromium Picolinate, Caffeine, Yohimbie HCl, Taurine, Vitamin B3, Vitamin B6, Vitamin B12

In addition to silica and magnesium stearate, each of the films listed above contains a variety of components, such as polymers and flavors, among others. The remainder of the components are provided below for each film description used in Table 2.

Films identified in Table 2 above as "SOURS" contain the following components listed in Table 3:

TABLE 3

| Component | Weight % |
|---|---|
| HYDROXYPROPYL METHYLCELLULOSE | 0.01%-60% |
| CITRIC ACID | 0.01%-40% |
| NATURAL &ARTIFICIAL FLAVORS | 0.01%-25% |
| GUM ARABIC | 0.01%-10% |
| MAGNESIUM STEARATE | 0.01%-10% |
| SODIUM HEXAMETAPHOSPHATE | 0.01%-5% |
| SILICA | 0.01%-2% |
| POLYSORBATE 80 | 0%-5% |
| MALIC ACID | 0.01%-10% |
| ASPARTAME | 0.01%-3.5% |
| POTASSIUM ACESULFAME | 0.01%-0.5% |
| DYE | 0.01%-1% |
| POTASSIUM SORBATE | 0.01%-0.1% |
| SODIUM BENZOATE | 0.01%-0.1% |

Films identified in Table 2 above as "Benzocaine/Menthol" contain the following components listed in Table 4:

TABLE 4

| Component | Weight % |
|---|---|
| HYDROXYPROPYL METHYLCELLULOSE | 0.01%-70% |
| NATURAL &ARTIFICIAL FLAVORS | 0.01%-25% |
| POLYETHYLENE OXIDE | 0.01%-50% |
| MENTHOL CRYSTALS | 0.01%-30% |
| CORN STARCH | 0.01%-30% |
| BENZOCAINE | 0.01%-10% |
| SUCRALOSE | 0.01%-5% |
| MALIC ACID | 0.01%-5% |
| MAGNESIUM STEARATE | 0.01%-10% |
| SILICA | 0.01%-2% |
| TITANIUM DIOXIDE | 0.01%-5% |
| BUTYLATED HYDROXYTOLUENE | 0.01%-1% |
| DYE | 0.01%-1% |

Films identified in Table 2 above as "Energy/Wellness Supplement" contain the following components listed in Table 5:

TABLE 5

| Component | Weight % |
|---|---|
| HYDROXYPROPYL METHYLCELLULOSE | 0%-70% |
| HYDROXYPROPYL CELLULOSE | 0%-40% |
| PECTIN | 0%-40% |
| NATURAL &ARTIFICIAL FLAVORS/ FLAVOR ADJUVANTS | 0%-30% |
| POLYDEXTROSE | 0.01%-30% |
| SODIUM CARBOXYMETHYLCELLULOSE | 0%-10% |
| ENERGY/WELLNESS ACTIVES[2] | 0.01%-50% |
| ERYTHRITOL | 0%-20% |
| SUCRALOSE | 0.01%-5% |
| CITRIC ACID | 0%-10% |
| MAGNESIUM STEARATE | 0.01%-10% |
| GLYCERYL MONOOLEATE | 0%-1% |
| SILICA | 0.01%-2% |
| POLYSORBATE 80 | 0%-1% |
| SORBITAN MONOOLEATE | 0%-1% |
| POTASSIUM SORBATE | 0%-0.1% |
| SODIUM BENZOATE | 0%-0.1% |
| SODIUM HEXAMETAPHOSPHATE | 0%-10% |
| PROPYLENE GLYCOL | 0%-25% |
| GUM ARABIC | 0%-10% |
| DYE | 0.01%-1% |

Films identified in Table 2 above as "ORAL ANALGESIC" contain the following components listed in Table 6:

TABLE 6

| Component | Weight % |
|---|---|
| HYDROXYPROPYL METHYLCELLULOSE | 0.01%-70% |
| CHOLINE SALICYLATE | 0.01%-60% |
| NATURAL &ARTIFICIAL FLAVORS | 0.01%-10% |
| MAGNESIUM STEARATE | 0.01-5% |
| SILICA | 0.01-2% |
| CETALKONIUM CHLORIDE | 0.01%-5% |
| METHYL PARABEN | 0.01%-0.1% |
| DIMETHYLPOLYSILOXANE | 0.01%-0.05% |

Films identified in Table 2 above as "Melatonin" contain the following components listed in Table 7:

TABLE 7

| Component | Weight % |
|---|---|
| HYDROXYPROPYL METHYLCELLULOSE | 0.01%-70% |
| NATURAL &ARTIFICIAL FLAVORS/ FLAVOR ADJUVANTS | 0.01%-20% |
| POLYETHYLENE OXIDE | 0.01%-30% |
| MELATONIN | 0.01%-20% |
| PECTIN | 0.01%-10% |
| POLYDEXTROSE | 0.01%-20% |
| SUCRALOSE | 0.01%-5% |
| MAGNESIUM STEARATE | 0.01%-10% |
| SILICA | 0.01%-2% |
| GLYCERYL MONOOLEATE | 0.01%-1% |
| TITANIUM DIOXIDE | 0.01%-5% |
| MONOAMMONIUM GLYCYRRHIZINATE | 0.01%-2% |
| BUTYLATED HYDROXYTOLUENE | 0.01%-1% |
| DYE | 0.01%-1% |

Films identified in Table 2 above as "Chlorine Dioxide" contain the following components listed in Table 8:

TABLE 8

| Component | Weight % |
|---|---|
| HYDROXYPROPYL METHYLCELLULOSE | 0.01%-70% |
| POLYETHYLENE OXIDE | 0.01%-50% |
| POLYDEXTROSE | 0.01%-20% |
| NATURAL & ARTIFICIAL FLAVORS/ FLAVOR ADJUVANTS | 0.01%-30% |
| MAGNESIUM STEARATE | 0.01%-5% |
| SILICA | 0.01%-2% |
| SUCRALOSE | 0.01%-5% |
| ZINC GLUCONATE DIHYDRATE | 0.01%-5% |
| CITRIC ACID | 0.01%-2% |
| GLYCERYL MONOOLEATE | 0.01%-1% |
| SODIUM HYDROXIDE | 0.01%-5% |
| SODIUM BICARBONATE | 0.01%-5% |
| CHLORINE DIOXIDE 2% SOLUTION | 0.01%-10% |
| BUTYLATED HYDROXYTOLUENE | 0.01%-1% |
| DYE | 0.01%-1% |
| SODIUM BENZOATE | 0.01%-0.1% |

Films identified in Table 2 above as "Multivitamin" contain the following components listed in Table 9:

TABLE 9

| Component | Weight % |
|---|---|
| HYDROXYPROPYL METHYLCELLULOSE | 0.01%-50% |
| NATURAL &ARTIFICIAL FLAVORS | 0.01%-20% |
| NIACINAMIDE -100% (Vitamin B3) | 0.01%-30% |
| POLYETHYLENE OXIDE | 0.01%-30% |
| POLYDEXTROSE | 0.01%-20% |

TABLE 9-continued

| Component | Weight % |
|---|---|
| ASCORBIC ACID -100% (Vitamin C) | 0.01%-20% |
| 50% VITAMIN E ACETATE -91.2% | 0.01%-10% |
| CALCIUM d-PANTOTHENATE -92% (Vitamin B5) | 0.01%-10% |
| SUCRALOSE | 0.01%-5% |
| VITAMIN A PALMITATE-15% | 0.01%-10% |
| PYRIDOXINE HYDROCHLORIDE -82.3% (VITAMIN B6) | 0.01%-10% |
| RIBOFLAVIN -100% (Vitamin B2) | 0.01%-10% |
| THIAMINE HYDROCHLORIDE -89.2% (Vitamin B1) | 0.01%-10% |
| MAGNESIUM STEARATE | 0.01%-2% |
| SILICA | 0.01%-2% |
| GLYCERYL MONOOLEATE | 0.01%-1% |
| 5% VITAMIN K- 100% | 0.01%-5% |
| 2.5% VITAMIN D3 LIQUID -100% | 0.01%-5% |
| BUTYLATED HYDROXYTOLUENE | 0.01%-1% |
| CYANOCOBALAMIN -100% (Vitamin B12) | 0.001%-1% |

Films identified in Table 2 above as "Zinc/Elderberry" contain the following components listed in Table 10:

TABLE 10

| Component | Weight % |
|---|---|
| HYDROXYPROPYL METHYLCELLULOSE | 0.01%-60% |
| ZINC GLUCONATE | 0.01%-20% |
| ELDERBERRY EXTRACT | 0.01%-20% |
| FRUCTOSE | 0.01%-20% |
| NATURAL &ARTIFICIAL FLAVORS | 0.01%-30% |
| POLYETHYLENE OXIDE | 0.01%-20% |
| POLYDEXTROSE | 0.01%-20% |
| ASCORBIC ACID -100% (Vitamin C) | 0.01%-20% |
| SUCRALOSE | 0.01%-5% |
| GLYCERYL MONOOLEATE | 0.01%-1% |
| MAGNESIUM STEARATE | 0.01%-5% |
| TITANIUM DIOXIDE | 0.01%-2% |
| SILICA | 0.01%-2% |
| BUTYLATED HYDROXYTOLUENE | 0.01%-1% |

Films identified in Table 2 above as "B-Complex Vitamin" contain the following component listed in Table 11:

TABLE 11

| Component | Weight % |
|---|---|
| HYDROXYPROPYL METHYLCELLULOSE | 0.01%-60% |
| POLYETHYLENE OXIDE | 0.01%-50% |
| CALCIUM d-PANTOTHENATE -92% (Vitamin B5) | 0.01%-20% |
| POLYDEXTROSE | 0.01%-30% |
| NATURAL &ARTIFICIAL FLAVORS/FLAVOR ADJUVANTS | 0.01%-25% |
| PYRIDOXINE HYDROCHLORIDE -82.3% (VITAMIN B6) | 0.01%-20% |
| RIBOFLAVIN -100% (Vitamin B2) | 0.01%-20% |
| THIAMINE HYDROCHLORIDE -89.2% (Vitamin B1) | 0.01%-20% |
| SUCRALOSE | 0.01%-5% |
| PROPYLENE GLYCOL | 0.01%-5% |
| MAGNESIUM STEARATE | 0.01%-10% |
| SILICA | 0.01%-2% |
| GLYCERYL MONOOLEATE | 0.01%-1% |
| BUTYLATED HYDROXYTOLUENE | 0.01%-1% |
| DYE | 0.01%-1% |
| CYANOCOBALAMIN -100% (Vitamin B12) | 0.001%-1% |

Films identified in Table 2 above as "Immune Booster" contain the following components listed in Table 12:

TABLE 12

| Component | Weight % |
|---|---|
| HYDROXYPROPYL METHYLCELLULOSE | 0.01%-70% |
| POLYDEXTROSE | 0.01%-50% |
| POLYETHYLENE OXIDE | 0.01%-50% |
| ZINC CITRATE TRIHYDRATE | 0.01%-40% |
| SUCRALOSE | 0.01%-5% |
| NATURAL FLAVORS | 0.01%-20% |
| CITRIC ACID | 0.01%-20% |
| MAGNESIUM STEARATE | 0.01%-10% |
| SILICA | 0.01%-2% |
| SODIUM CITRATE | 0.01%-5% |
| GLYCERYL MONOOLEATE | 0.01%-1% |
| BUTYLATED HYDROXYTOLUENE | 0.01%-2% |
| MONOAMMONIUM GLYCYRRHIZINATE | 0.01%-1% |
| DYE | 0.01%-1% |

Films identified in Table 2 above as "Cold & Cough" contain the following components listed in Table 13:

TABLE 13

| Component | Weight % |
|---|---|
| HYDROXYPROPYL METHYLCELLULOSE | 0.01%-60% |
| POLYDEXTROSE | 0.01%-30% |
| NATURAL &ARTIFICIAL FLAVORS | 0.01%-25% |
| POLYETHYLENE OXIDE | 0.01%-50% |
| ASCORBIC ACID -100% (Vitamin C) | 0.01%-30% |
| ZINC CITRATE DIHYDRATE | 0.01%-20% |
| ECHINACEA PURPUREA | 0.01%-20% |
| SUCRALOSE | 0.01%-10% |
| PECTIN | 0.01%-20% |
| CITRIC ACID | 0.01%-10% |
| SODIUM CITRATE | 0.01%-5% |
| MAGNESIUM STEARATE | 0.01%-10% |
| SILICA | 0.01%-2% |
| GLYCERYL MONOOLEATE | 0.01%-1% |
| DYE | 0.01%-1% |
| BUTYLATED HYDROXYTOLUENE | 0.01%-1% |
| MONOAMMONIUM GLYCYRRHIZINATE | 0.01%-1% |

Films identified in Table 2 above as "Stress Relief" contain the following components listed in Table 14:

TABLE 14

| Component | Weight % |
|---|---|
| HYDROXYPROPYL METHYLCELLULOSE | 0.01%-60% |
| CHAMOMILE | 0.01%-40% |
| PASSION FLOWER | 0.01%-40% |
| PECTIN | 0.01%-20% |
| NATURAL &ARTIFICIAL FLAVORS | 0.01%-25% |
| GLYCERIN | 0.01%-10% |
| POLYSORBATE 80 | 0%-2% |
| SUCRALOSE | 0.01%-5% |
| POLYDIMETHYLSILOXANE EMULSION | 0.01%-2% |
| ASPARTAME | 0.01%-5% |
| POTASIUM ACESULFAME | 0.01%-3% |
| POTASSIUM SORBATE | 0.01%-1% |

Films identified in Table 2 above as "Cinnamint" contain the following components listed in Table 15:

TABLE 15

| Component | Weight % |
|---|---|
| HYDROXYPROPYL METHYLCELLULOSE | 0.01%-70% |
| POLYETHYLENE OXIDE | 0.01%-50% |
| POLYDEXTROSE | 0.01%-30% |
| BUTYLATED HYDROXYTOLUENE | 0.01%-1% |
| GLYCERYL MONOOLEATE | 0.01%-1% |
| MAGNESIUM STEARATE | 0.01%-10% |

TABLE 15-continued

| Component | Weight % |
| --- | --- |
| SILICA | 0.01%-2% |
| POTASSIUM SORBATE | 0.01%-0.1% |
| SODIUM BENZOATE | 0.01%-0.1% |
| NATURAL &ARTIFICIAL FLAVORS | 0.01%-30% |
| SUCRALOSE | 0.01%-5% |
| XYLITOL | 0.01%-10% |
| DYE | 0.01%-1% |

Films identified in Table 2 above as "Dextromethorphan Hydrobromide" contain the following components listed in Table 16:

TABLE 16

| Component | Weight % |
| --- | --- |
| Dextromethorphan Hydrobromide 60% | 0.01%-60% |
| POLYETHYLENE OXIDE | 0.01%-70% |
| POLYDEXTROSE | 0.01%-30% |
| HYDROXYPROPYL METHYLCELLULOSE | 0.01%-70% |
| NATURAL &ARTIFICIAL FLAVORS | 0.01%-30% |
| SUCRALOSE | 0.01%-5% |
| MAGNESIUM STEARATE | 0.01%-10% |
| SILICA | 0%-2% |
| SODIUM BICARBONATE | 0.01%-5% |
| XANTHAN GUM | 0.01%-10% |
| TITANIUM DIOXIDE | 0.01%-5% |
| BUTYLATED HYDROXYTOLUENE | 0.01%-1% |
| DYE | 0.01%-1% |

The films prepared in these Examples exhibited improved glidant properties, particularly the ability to slide against one another without sticking together.

Examples 244-300

Water-soluble thin films were prepared incorporating silica and magnesium stearae as anti-tacking agents in the amounts described in Table 17. More specifically, various combinations of silica and magnesium stearate were incorporated into a variety of different film compositions as shown in the table below.

TABLE 17

| Example | Film description | Silica[1] (weight %) | Magnesium stearate (weight %) |
| --- | --- | --- | --- |
| 244 | SOURS | 1.5 | 2.5 |
| 245 | ENERGY/WELLNESS SUPPLEMENT[2] | 0.75 | 1 |
| 246 | ENERGY/WELLNESS SUPPLEMENT[2] | 0.75 | 1 |
| 247 | MELATONIN | 1 | 2 |
| 248 | MELATONIN | 1.5 | 1.5 |
| 249 | CHLORINE DIOXIDE | 1.5 | 1.5 |
| 250 | MELATONIN | 1.5 | 1.5 |
| 251 | MELATONIN | 1.5 | 1.5 |
| 252 | MELATONIN | 1.5 | 1.5 |
| 253 | MELATONIN | 1.5 | 1.5 |
| 254 | CHLORINE DIOXIDE | 1.5 | 1.5 |
| 255 | MELATONIN | 1.1 | 1.3 |
| 256 | MULTIVITAMIN | 1 | 1 |
| 257 | MULTIVITAMIN | 1 | 1 |
| 258 | B COMPLEX VITAMIN | 1 | 1 |
| 259 | MULTIVITAMIN | 1 | 1 |
| 260 | B COMPLEX VITAMIN | 1 | 1 |
| 261 | COLD & COUGH | 1 | 1 |
| 262 | MULTIVITAMIN | 1 | 1 |
| 263 | MULTIVITAMIN | 1 | 1 |
| 264 | MULTIVITAMIN | 1 | 1 |
| 265 | MULTIVITAMIN | | |
| 266 | MULTIVITAMIN | | |
| 267 | MULTIVITAMIN | | |
| 268 | MULTIVITAMIN | 1 | 1.5 |
| 269 | IMMUNE BOOSTER | 1.16 | 1.16 |
| 270 | MULTIVITAMIN | 1 | 1 |
| 271 | ENERGY/WELLNESS SUPPLEMENT[2] | 1 | 1.5 |
| 272 | MULTIVITAMIN | 1 | 1.5 |
| 273 | MULTIVITAMIN | 1 | 1.5 |
| 274 | MELATONIN | 1.1 | 1.3 |
| 275 | MULTIVITAMIN | 1 | 1 |
| 276 | MULTIVITAMIN | 1 | 1 |
| 277 | MULTIVITAMIN | 1 | 1 |
| 278 | MULTIVITAMIN | 1 | 1 |
| 279 | MULTIVITAMIN | 1 | 1 |
| 280 | ENERGY/WELLNESS SUPPLEMENT[2] | 1.5 | 1.5 |
| 281 | MULTIVITAMIN | 1 | 1.5 |
| 282 | MULTIVITAMIN | 1 | 1.5 |
| 283 | MULTIVITAMIN | 1.5 | 0.3 |
| 284 | MULTIVITAMIN | 1 | 1 |
| 285 | B-COMPLEX VITAMIN | 1 | 1 |
| 286 | ENERGY/WELLNESS SUPPLEMENT[2] | 1 | 0.5 |
| 287 | MULTIVITAMIN | 1 | 1 |
| 288 | MELATONIN | 1.1 | 1.3 |
| 289 | B-COMPLEX VITAMIN | 1 | 1 |
| 290 | B-COMPLEX VITAMIN | 1 | 1 |
| 291 | ENERGY/WELLNESS SUPPLEMENT[2] | 1 | 0.5 |
| 292 | ENERGY/WELLNESS SUPPLEMENT[2] | 1 | 0.5 |
| 293 | B-COMPLEX VITAMIN | 1 | 1 |
| 294 | MULTIVITAMIN | 1 | 1 |
| 295 | CHLORINE DIOXIDE | 1.5 | 1.5 |
| 296 | MULTIVITAMIN | 1 | 1.5 |
| 297 | MULTIVITAMIN | 1 | 1 |
| 298 | MULTIVITAMIN | 1 | 1 |
| 299 | MULTIVITAMIN | 1 | 1 |
| 300 | BENZOCAINE/MENTHOL | 1.5 | 1.5 |

[1]Sipernat 500LS, available from Degussa
[2]Energy/Wellness Supplement may contain any/all of the following actives or combinations thereof: Green Tea, Guarana, Chromium Picolinate, Caffeine, Yohimbie HCl, Taurine, Vitamin B3, Vitamin B6, Vitamin B12

Besides silica and magnesium stearate, the remainder of the components contained in the films listed in Table 17 are provided in connection with Table 2 above. The film descriptions used in Tables 2 and 17 are the same.

The films prepared in these Examples exhibited improved glidant properties, particularly the ability to slide against one another without sticking together.

While there have been described what are presently believed to be the preferred embodiments of the invention, those skilled in the art will realize that changes and modifications may be made thereto without departing from the spirit of the invention, and it is intended to include all such changes and modifications as fall within the true scope of the invention.

What is claimed is:

1. An oral film for delivery of a desired amount of an active component comprising:
    an ingestible, water-soluble, polymer matrix;
    at least one anti-tacking agent selected from the group consisting of stearates; stearic acid; waxes; a blend of magnesium stearate and sodium lauryl sulfate; boric acid; surfactants; sodium benzoate; sodium acetate; sodium chloride; DL-Leucine; polyethylene glycol; sodium oleate; sodium lauryl sulfate; magnesium lauryl sulfate; talc; corn starch; amorphous silicon dioxide;

syloid; metallic stearates, Vitamin E, Vitamin E TPGS, silica and combinations thereof; and a substantially uniform distribution of said desired amount of said active component within said polymer matrix, wherein said active component is selected from the group consisting of cosmetic agents, pharmaceutical agents, vitamins, bioactive agents and combinations thereof, said film being formed by a controlled drying process which rapidly forms a viscoelastic matrix to lock-in said active in place within said matrix and maintain said substantially uniform distribution;

wherein said film is self-supporting and the active component is substantially uniformly distributed, whereby said substantially uniform distribution is measured by substantially equally sized individual unit doses which do not vary by more than 10% of said desired amount of said active component.

2. The film of claim 1, wherein said anti-tacking agent comprises magnesium stearate.

3. The film of claim 2, wherein said anti-tacking agent further comprises silica.

4. The film of claim 1, wherein said anti-tacking agent is present in amounts of about 0.01% to about 20% by weight of said delivery system.

5. The film of claim 1, wherein said anti-tacking agent comprises:
   magnesium stearate present in amounts of about 0.1% to about 2.5% by weight of said delivery system; and
   silica present in amounts of about 0.1% to about 1.5% by weight of said delivery system.

6. The film of claim 1, wherein said water-soluble polymer matrix comprises polyethylene oxide and a cellulosic polymer.

7. The film of claim 6, wherein said cellulosic polymer comprises hydroxypropyl cellulose.

8. The film of claim 6, wherein said cellulosic polymer comprises hydroxypropylmethyl cellulose.

9. The film of claim 1, wherein said active component comprises dextromethorphan.

10. The film of claim 1, further comprising polydextrose.

11. The film of claim 1, wherein said film is applied to an oral cavity of a mammal.

12. The film of claim 11, wherein said film adheres to the tongue or the buccal cavity of the mammal.

13. The film of claim 1, wherein the anti-tacking agent is present in an amount sufficient to impart reduced film-to-film coefficient of friction.

14. The film of claim 1, wherein said film has a coefficient of friction which is low enough to reduce adhesion of said film to the roof of a mouth of a user of said film upon placement into the user's mouth.

15. The film of claim 1 further comprising a flavoring agent.

16. The film of claim 1 further comprising a coloring agent.

17. The film of claim 1 wherein the anti-tacking agent comprises sodium benzoate.

18. The film of claim 1, wherein the active component comprises an opiate, opiate derivative, an analgesic and combinations thereof.

19. The film of claim 1, further comprising a preservative.

20. The film of claim 1, wherein the film is sufficient to impart reduced film-to-film coefficient of friction.

* * * * *